United States Patent

Sugino et al.

[11] Patent Number: 4,550,118
[45] Date of Patent: Oct. 29, 1985

[54] HETEROCYCLIC COMPOUNDS

[75] Inventors: Toshiya Sugino; Fujio Nohara; Tomoaki Fujinawa; Kazuo Ogawa; Teruo Mizukami; Shunichi Shirai, all of Toyama, Japan

[73] Assignees: Ikeda Mohando Co., Ltd., Toyama; Otsuka Pharmaceutical Co., Ltd., Tokyo, both of Japan

[21] Appl. No.: 544,591

[22] Filed: Oct. 24, 1983

[30] Foreign Application Priority Data

Oct. 26, 1982 [JP] Japan .................................. 57-188876

[51] Int. Cl.⁴ .................. C07D 401/14; C07D 403/12; C07D 413/14; A61K 31/41; A61K 31/415; A61K 31/44; A61K 31/54; A61K 31/535
[52] U.S. Cl. ..................... 514/383; 514/222; 514/227; 514/237; 514/239; 514/231; 514/232; 514/253; 514/254; 514/316; 514/318; 514/322; 514/333; 514/339; 544/139; 544/129; 544/124; 544/121; 544/62; 544/82; 544/357; 544/364; 544/370; 546/187; 546/193; 546/199; 546/271; 548/267

[58] Field of Search ............... 548/267; 544/139, 129, 544/124, 121, 62, 82, 357, 364, 370; 546/187, 193, 199, 271; 424/246, 248.4, 248.51, 248.52, 248.56, 248.57, 248.58, 250, 263, 267, 269, 273 B

[56] References Cited

FOREIGN PATENT DOCUMENTS 40696 12/1981 European Pat. Off. .

Primary Examiner—John M. Ford
Attorney, Agent, or Firm—Bucknam and Archer

[57] ABSTRACT

Compounds of Formula I are described

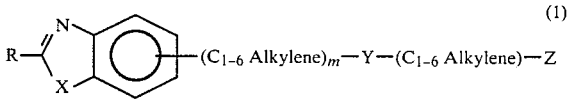
(1)

in which X and Y are independently —NH—, —O— or —S—; Z may be a pyrimidine, triazine, triazole, thiazole, thiadiazole ring. The methods of preparation are described. The compounds are useful as antipeptic ulcer agents.

37 Claims, No Drawings

HETEROCYCLIC COMPOUNDS

This invention relates to new heterocyclic compounds having the general formula shown below, and medically allowable salts, hydrates and solvates thereof:

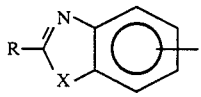
(1)

in which

R represents a hydrogen atom, or a $C_{1-6}$ alkyl, a substituted or unsubstituted amidino, a substituted or unsubstituted guanidino, or a

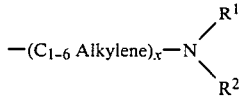

group (where x is 0 or 1, $R^1$ and $R^2$ are independently a hydrogen atom or a $C_{1-6}$ alkyl group, or

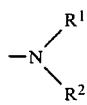

is a 5- or 6- membered heterocyclic group which may contain a —NH—, an —O— or a —S— bonding in addition to the N atom); X and Y represent independently a —NH—, an —O— or a —S— bonding;
  m is 0 or 1; and
  Z represents a

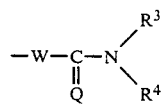

group (where W is a —NH— or a —CH$_2$— bonding, Q is a =NH, a =N—CN, a =CH—NO$_2$, a =N—SO$_2$NH$_2$, a =N—CONH$_2$, a =NSO$_2$ (aryl), a =NSO$_2$(C$_{1-6}$ alkyl) or a =N—(C$_{1-6}$ alkyl) group, $R^3$ and $R^4$ are independently a hydrogen atom, or a C$_{1-6}$ alkyl, a C$_{2-6}$ alkenyl or a C$_{2-6}$ alkynyl group, or

is a 5- or 6-membered heterocyclic group which may contain a —NH—, an —O— or a —S— bonding in addition to the N atom),
  a

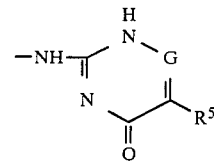

group (where G is a =CH— or a =N— bonding, $R^5$ is a hydrogen atom or a C$_{1-6}$ alkyl,
  a

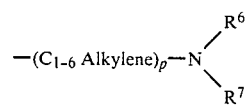

group (where p is 0 or 1, $R^6$ and $R^7$ are independently a hydrogen atom or a $C_{1-6}$ alkyl group, or

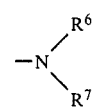

is a 5- or 6-membered heterocyclic group which may contain a —NH—, an —O— or a —S— bonding in addition to the N atom), a —(C$_{1-6}$ Alkylene)$_q$—A group (where q is 0 or 1, A is a substituted or unsubstituted aryl group) or a

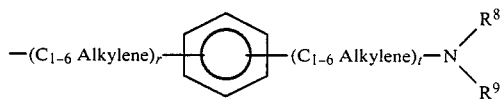

group (where r and t are independently 0 or 1, $R^8$ and $R^9$ are independently a hydrogen atom or a C$_{1-6}$ alkyl group, or

is a 5- or 6-membered heterocyclic group which may contain a —NH—, an —O— or a —S— bonding in addition to the N atom)
  a

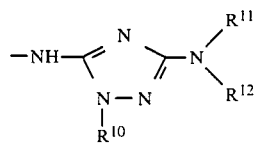

group (where $R^{10}$ is a hydrogen atom, or a C$_{1-6}$ alkyl, a substituted or unsubstituted phenyl, or a mono- or di-C$_{1-6}$ alkylamino or C$_{1-6}$ alkyl group, $R^{11}$ and $R^{12}$ are independently a hydrogen atom or a C$_{1-6}$ alkyl group,

is a 5- or 6-membered heterocyclic group which may contain a —NH—, an —O— or a —S— bonding in addition to the N atom), or a

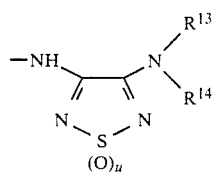

group (where u is 1 or 2, $R^{13}$ and $R^{14}$ are independently a hydrogen atom, or a $C_{1-6}$ alkyl, a $C_{2-6}$ alkenyl, a $C_{2-6}$ alkynyl, an amino, an amino $C_{1-6}$ alkyl or a mono- or di-$C_{1-6}$ alkylamino $C_{1-6}$ alkyl group, or

is a 5- or 6-membered heterocyclic group which may contain a —NH—, an —O— or a —S— bonding in addition to the N atom).

The compounds of general formula (I) of the invention antagonize against histamine $H_2$ activity, and are effective as antagonists against histamine $H_2$ receptors, i.e., gastric acid secretion inhibitors. Also, the compounds of the invention have gastric mucus secretion-accelerating activities, and are useful as agents for protecting and reinforcing the gastric mucosal surface. Therefore, the compounds of the invention are extremely useful as therapeutic agents for peptic ulcer such as gastric and duodenal ulcers. Also, the compounds of the invention have low toxicity, and the duration time of the above activities are characteristically long.

In the present specification, $C_{1-6}$ alkyl groups indicate the alkyl groups having 1–6 carbon atoms such as, for example, methyl, ethyl, isopropyl, propyl, butyl, tert-butyl, pentyl and hexyl groups. $C_{2-6}$ alkenyl groups indicate alkenyl groups having 2–6 carbon atoms such as, for example, vinyl, 2-propenyl, 2-butenyl, 3-butenyl, 2-pentenyl, 2-hexenyl and 1-methylallyl groups. $C_{2-6}$ alkynyl groups indicate alkynyl groups having 2–6 carbon atoms such as, for example, ethynyl, 2-propynyl, 2-butynyl, 3-butynyl, 2-pentynyl, 2-hexynyl and 1-methyl-2-propynyl. $C_{1-6}$ alkylene groups indicate alkylene groups having 1–6 carbon atoms such as, for example, methylene, ethylene, trimethylene, tetramethylene, pentamethylene, hexamethylene, methylmethylene, 2-methyltrimethylene, 2,2-dimethyltrimethylene and dimethylmethylene groups.

In the specification, 5- or 6-membered heterocyclic groups represented by

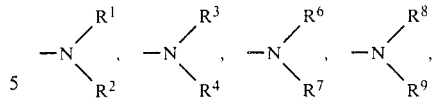

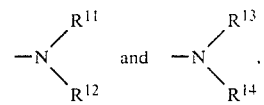

which may contain —NH—, —O— or —S— in addition to the N atoms are, for example, morpholino, piperidino, pyrrolidino, piperazino and thiomorpholino groups, and the said heterocyclic groups may also be substituted by $C_{1-6}$ alkyl groups. The $C_{1-6}$ alkyl-substituted heterocyclic groups include, for example, 4-methylpiperazino, 4-methylpiperidino, 3-methylpyrrolidino, 4-ethylpiperazino, 4-isopropylpiperazino, 4-butylpiperazino, 4-pentylpiperazino, 4-hexylpiperazino groups.

Also, substituents for substituted amidino and substituted guanidino groups include alkyl groups of 1–6 carbon atoms, for example, methyl, ethyl, propyl, isopropyl, butyl, tert-butyl, pentyl, hexyl groups, etc.

Substituted or unsubstituted aryl groups expressed by 'A' include, for example, phenyl group and phenyl groups substituted by alkylenedioxy group having 1–4 carbon atoms such as methylenedioxyl and ethylenedioxy substituents. $C_{1-6}$ alkoxy groups include, for example, methoxy, ethoxy, propoxy, isopropoxy, butoxy, tert-butoxy, pentyloxy, hexyloxy and other alkoxy groups having 1–6 carbon atoms. Halogens include fluorine, chlorine, bromine and iodine atoms.

Mono- or di-$C_{1-6}$ alkylamino-$C_{1-6}$ alkyl groups include, for example, methylaminomethyl, 2-methylaminoethyl, 2-ethylaminomethyl, 2-ethylaminoethyl, isopropylaminomethyl, butylaminomethyl, pentylaminomethyl, hexylaminomethyl, 4-butylaminobutyl, dimethylaminomethyl, 2-dimethylaminoethyl, 3-dimethylaminopropyl, 4-dimethylaminobutyl, 5-dimethylaminopentyl, 6-dimethylaminohexyl, diethylaminomethyl, dipropylaminomethyl, dibutylaminomethyl, dihexylaminomethyl, 2-diethylaminoethyl, methylethylaminomethyl, 4-dibutylaminobutyl and other aminoalkyl groups having 1–6 carbon atoms substituted by one or two alkyl groups having 1–6 carbon atoms.

Amino-$C_{1-6}$ alkyl groups include, for example, aminomethyl, 2-aminoethyl, 3-aminopropyl, 4-aminobutyl, 5-aminopentyl, 6-aminohexyl, 2-aminopropyl and other aminoalkyl groups having 1–6 carbon atoms.

Substituent R in the compounds of general formula (I) above includes, for example, a hydrogen atom, and methyl, ethyl, propyl, isopropyl, nonsubstituted amidino, $C_{1-6}$ alkyl-substituted amidino, guanidino, $C_{1-6}$ alkyl substituted guanidino, amino, dimethylamino, dimethylaminomethyl, pyrrolidino, 1-pyrrolidinomethyl, piperidino, 1-piperidinomethyl, morpholino, 4-morpholinomethyl, thiomorpholino, piperazino, 1-piperazinomethyl and 1-(4-methyl)-piperazinomethyl groups.

X should be —NH—, —O— or —S— and preferably —NH—.

Y should be —NH—, —O— or —S— and preferably —O— or —S—.

In —($C_{1-6}$ alkylene)$_m$— groups m should preferably be 0 or m should preferably be 1 and $C_{1-6}$ alkylene should preferably be methylene.

In —Y—($C_{1-6}$ alkylene)—z group, $C_{1-6}$ alkylene should be alkylene group having 1–6 carbon atoms, and preferably straight alkylene having 2–5 carbon atoms if Y is —O— and m is 0; and straight alkylene having 2–3 carbon atoms if Y is —S— and m is 1.

In case of Z being

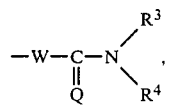

Q should preferably be =N—CN or =CH—NO$_2$ if W is —NH—; and =N—SO$_2$NH$_2$, =NCONH$_2$ or =NCN if W is —CH$_2$—. Also, it is preferable that both of $R^3$ and $R^4$ are hydrogen atoms; $R^3$ is a hydrogen atom and $R^4$ is a methyl, an ethyl, a propyl, a 2-propenyl or a 2-propynyl group; or

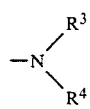

is a pyrrolidino or a piperidino group.

If Z is

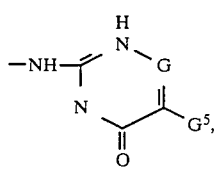

$R^5$ should particularly preferably be a hydrogen atom, or a dimethylaminomethyl, a diethylaminomethyl, a 1-pyrrolidinomethyl, a 1-piperidinomethyl, a 3-dimethylaminomethylbenzyl, a 3-(1-pyrrolidinomethyl)benzyl, a 3-(1-piperidinomethyl)benzyl, a 3-pyridinomethylbenzyl or a (3,4-methylenedioxy)benzyl group.

If Z is

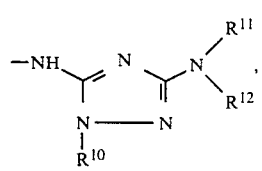

$R^{10}$ should preferably be a hydrogen atom, or a methyl, an ethyl, a propyl, a dimethylaminomethyl, a 2-dimethylaminoethyl or a 3-dimethylaminopropyl group. If $R^{10}$ is a substituted phenyl group, the substituent should be a $C_{1-6}$ alkyl, an amino, a mono- or di-$C_{1-6}$ alkylamino or $C_{1-6}$ alkyl or a $C_{1-6}$ alkoxy group, or a halogen atom. It is also preferable that both of $R^{11}$ and $R^{12}$ are hydrogen atoms, or that $R^{11}$ is a hydrogen atom and $R^{12}$ is a methyl, an ethyl or a propyl group, or that

is a pyrrolidino, piperidino or a morpholino group.

If Z is

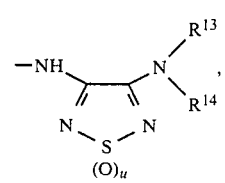

it is preferable that both of $R^{13}$ and $R^{14}$ are hydrogen atoms; or $R^{13}$ is a hydrogen atom and $R^{14}$ is a methyl, an ethyl, a propyl, an isopropyl, a 2-propenyl, a 2-propynyl or a dimethylamino methyl group; or

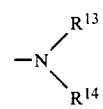

is a pyrrolidino or a piperidino group.

The compounds of general formula (I) of the invention may be prepared, for example, by the following processes.

(A) If Z is

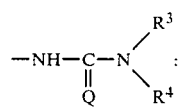

The first process is

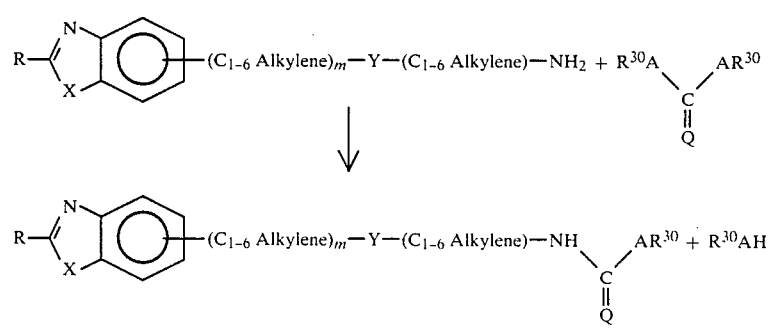

and the second process is

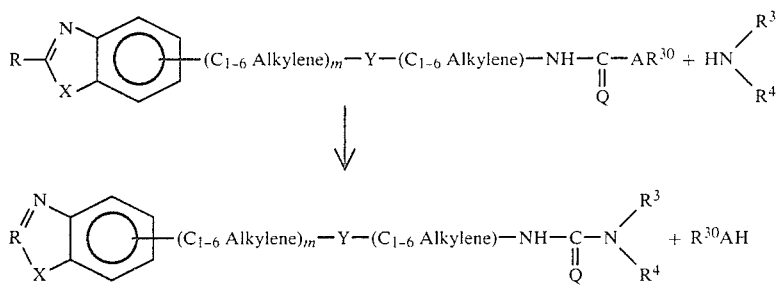

(where R, X, Y, m, Q, $R^3$ and $R^4$ are the same as above, $R^{30}$ is a $C_{1-6}$ alkyl and preferably a methyl group, and A is —S— or —O— and preferably —S—).

The above processes may be carried out separately, however, it is preferable that the processes are carried out continuously. In the first process, both of the materials should preferably be used in equimolar quantities. In the second process, the amines

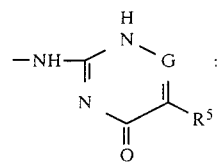

should preferably be used in excess quantities, i.e., 2–5 times greater quantities.

Both processes may be carried out in solvent-free conditions. However, inactive organic solvents such as methanol, ethanol, propanol, acetnitrile, chloroform, etc. may be used if solvents are required.

The reactions may be carried out at 0° C. to a temperature below the boiling point of each solvent (generally 50°–150° C.), and preferably at a temperature from room temperature to 80° C. The reaction time depends on the temperature; however, both processes are completed in 30 min to 24 hrs in total.

(B) If Z is $$-NH-\overset{H}{\underset{N}{C}}\!\!=\!\!\overset{N}{\underset{}{}}\overset{}{\underset{}{G}}$$

The process is

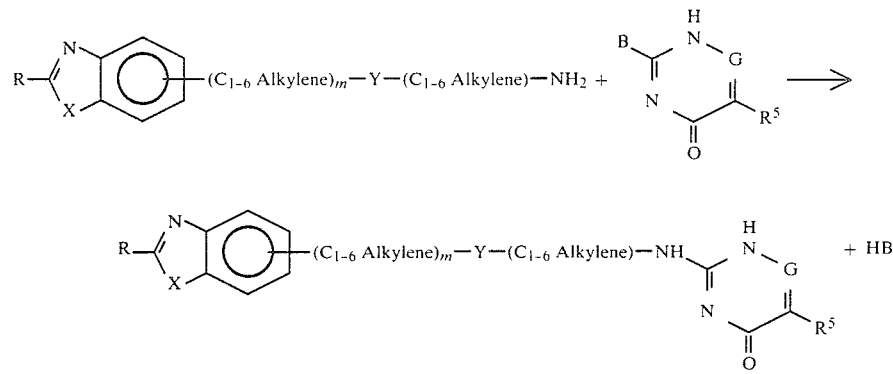

(where R, X, Y, G, $R^5$ and m are the same as mentioned above, and B is a $R^{40}$S— ($R^{40}$ is a $C_{1-6}$ alkyl and preferably a methyl group) or a nitroamino (—NH—NO$_2$) group).

If B is a methylthio group, the above reaction may be carried out at around 150° C. in solvent-free conditions or in reflux pyridine. If B is a nitroamino group, the reaction is carried out in inactive solvents such as ethanol and refluxing pyridine. The above pyrimidones (G is —CH=) and triazinones (G is —N=) are known substances, and may be prepared by, for example, Japanese Patent Public Disclosure No. 53-116392, Japanese Patent Public Disclosure No. 55-11583 and modifications of these which are manifest to those versed in the art.

(C) If Z is

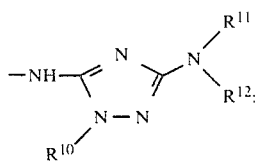

The first step is

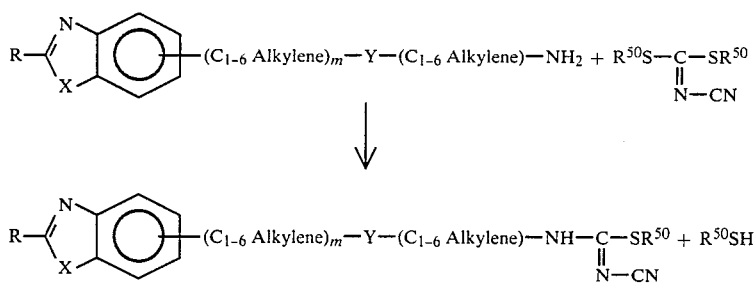

and the second step is

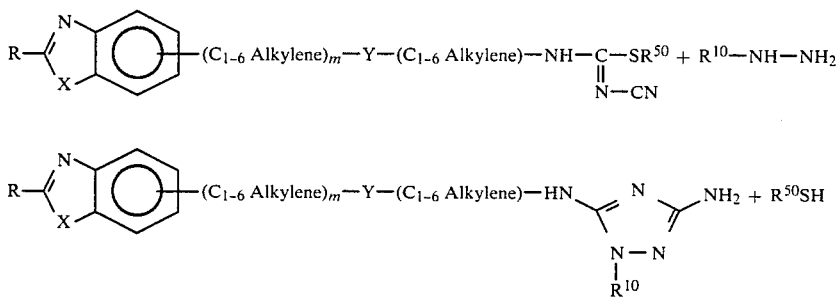

(where R, X, Y, $R^{10}$ and m are the same as mentioned above, and $R^{50}$ is a $C_{1-6}$ alkyl and preferably a methyl group).

The first step is carried out in inactive solvents such as alcohols, acetonitrile, etc. for 20 min to 48 hrs, with heating, if desired, using equimolar quantities of the raw materials. The reaction should preferably be carried out at room temperature for 2–6 hrs.

In the second process, the reaction product of the first step are caused to react with equimolar quantities to 10 times greater moles (preferably 1.5–3 times greater moles) of hydrazine derivatives in organic solvents such as methanol, ethanol, propanol, etc. The reaction proceeds at room temperature to 150° C. for 30 min to 24 hrs however, the reaction should preferably be carried out for 5 to 10 hrs at a temperature below the boiling point of lower alcohols such as methanol, ethanol, etc. It is simple for both processes to be carried out continuously. However, the intermediate products obtained by the first process are isolated for purification after completion of the first process, and the purified products are subjected to the second process so as to eliminate the formation of by-products. Both of $R^{11}$ and $R^{12}$ in the target compounds thus prepared are hydrogen atoms. Derivatives having $R^{11}$ and $R^{12}$ other than hydrogen atoms may be prepared by causing to react the compounds with those compounds having active elimination group such as halogenated alkyl group, etc. desired in an activated form. N-cyanodialkyldithioimidocarbonate used in the first process is a known substance, and may be prepared according to the process in Japanese Patent Publication 46-26482.

(D) If Z is

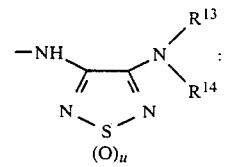

The first process is

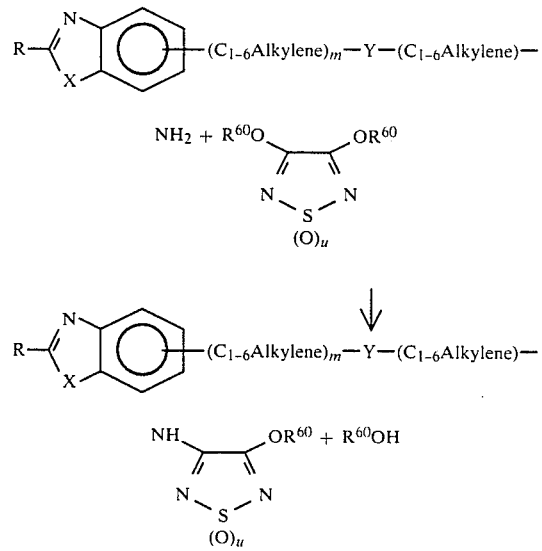

and the second process is

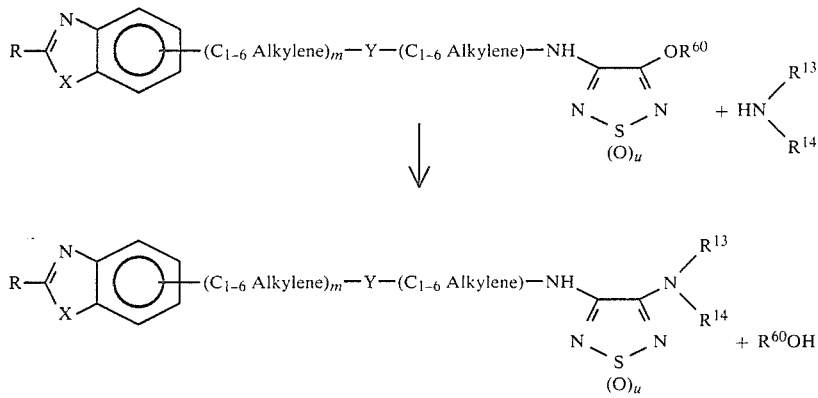

(where R, X, Y, $R^{13}$, $R^{14}$, m and u are the same as mentioned above, and $R^{60}$ is a $C_{1-6}$ alkyl group).

In the above reactions, 1,2,5-thiadiazol-1-oxide or a 1,1-dioxide derivative thereof used for the first process is a known substance, and may be prepared according to, for example, a method described in J. Org. Chem. 1975. vol. 40, pp 2749. In the first process, both materials are used in equimolar ratios, and the mixture is agitated in inactive solvents such as methanol, ethanol, acetonitrile, etc. at 0° to 80° C. for 5 min to 24 hrs. After completion of the first process, the intermediate products may be isolated for purification. However, if the first and the second processes are carried out continuously, amines in excess amounts to the intermediate products are caused to react in cold conditions in the second process. The amount of amines added should be twice to 20 times and preferably 5 to 10 times the amount of the intermediate products. The reaction should be carried out at 0°–80° C. for 5 min to 48 hrs, and preferably at room temperature for 20 min to 5 hrs.

(E) If Z is

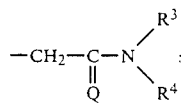

The first process is

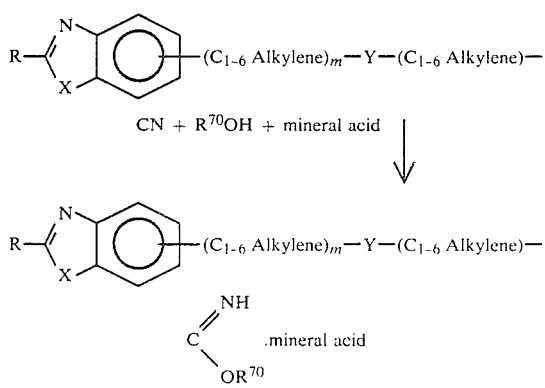

and the second process is

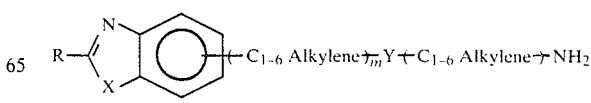

(where R, X, Y, Q, $R^3$, $R^4$ and m are the same as above, $R^{70}$ is a $C_{1-6}$ alkyl group and D is $H_2Q$ or $$HN\begin{matrix}R^3\\ \\R^4\end{matrix}).$$

In the above reactions, lower alcohols used for the first process should preferably be free from water. Mineral acids include hydrochloric acid, sulfuric acid, nitric acid, etc., and should preferably be dried hydrochloric acid gas. The reaction should be carried out at −20° C. to 25° C. and preferably at −5° C. to 5° C. for 30 min to 24 hrs in the first process. The second process should preferably be carried out continuously following the first process. In the second process, the reaction temperature is not particularly be restricted. However, the reaction should preferably be carried out at room temperature to elevated temperatures (50°–80° C.) for 30 min to 24 hrs.

The starting materials used in preparation methods (A) to (E) described above, i.e., and

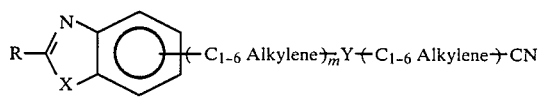
are new compounds. These compounds may be prepared according to the processes outlined below with reference to the equations of reaction, or similar processes thereto.
(F) 5-aminoalkyloxy-2-substituted aminomethylbenzimidazole
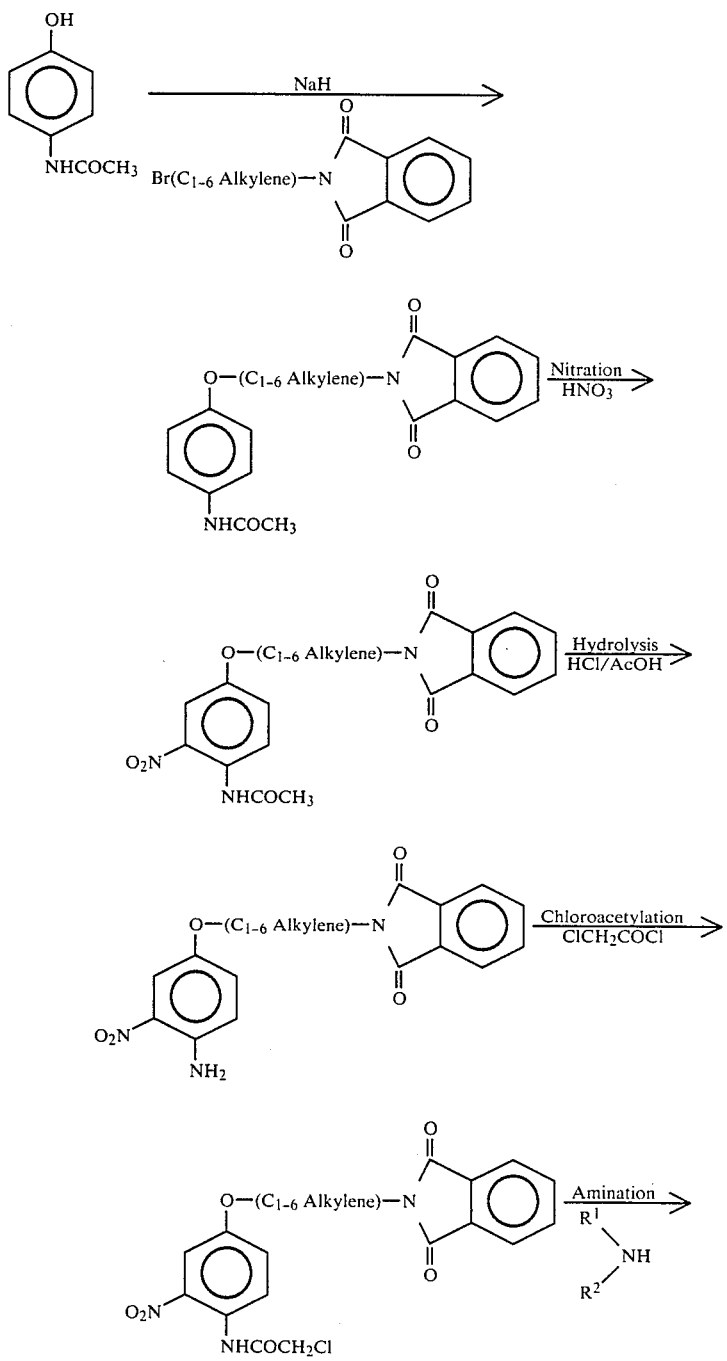

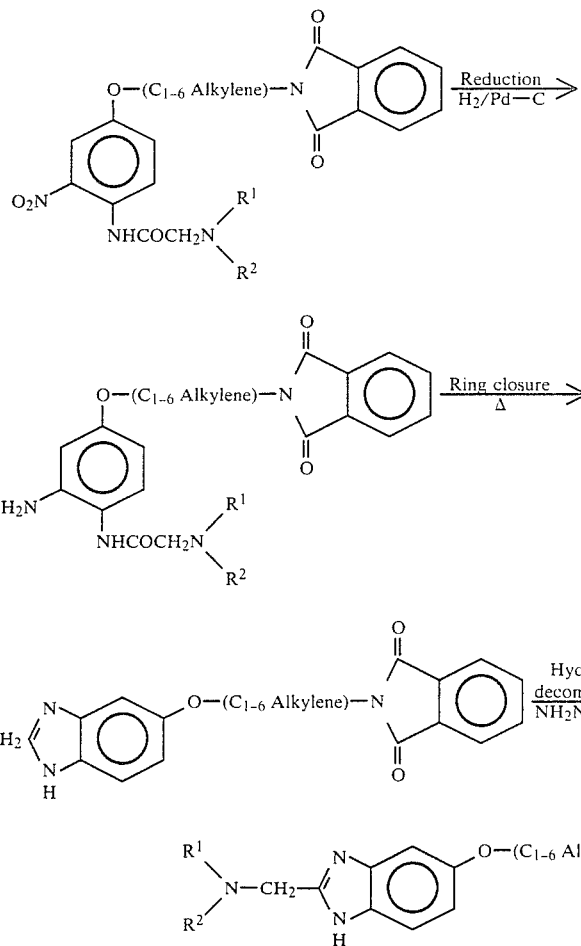
(G) 6-aminoalkyloxy-2-substituted aminomethylbenzothiazole
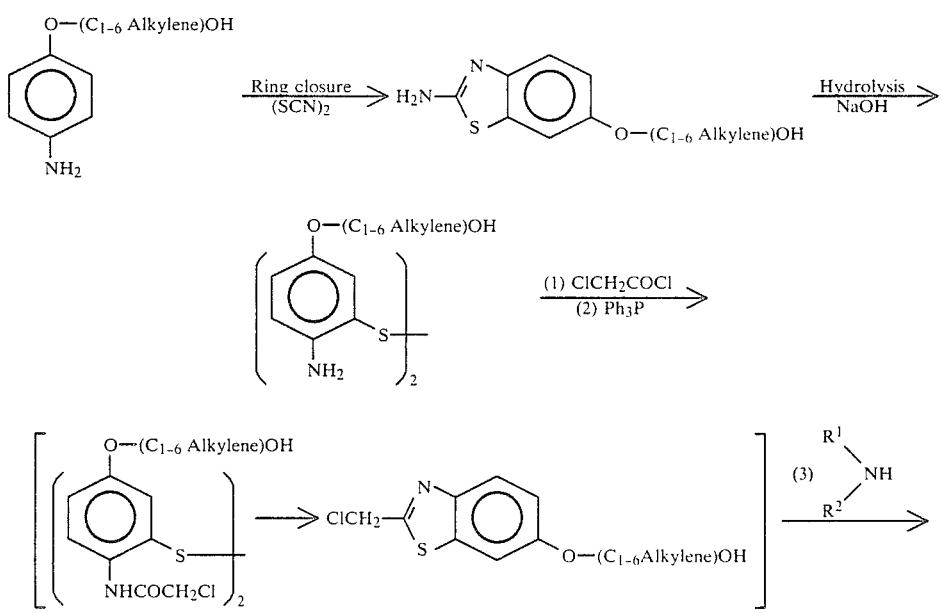

-continued
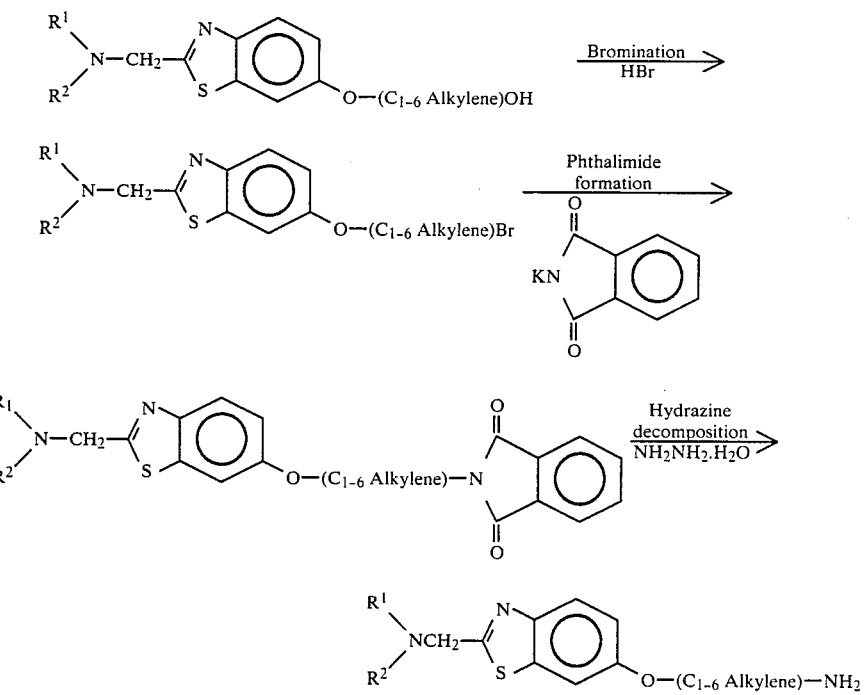
(H) 5-aminoalkyloxy-2-substituted aminomethylbenzoxazole
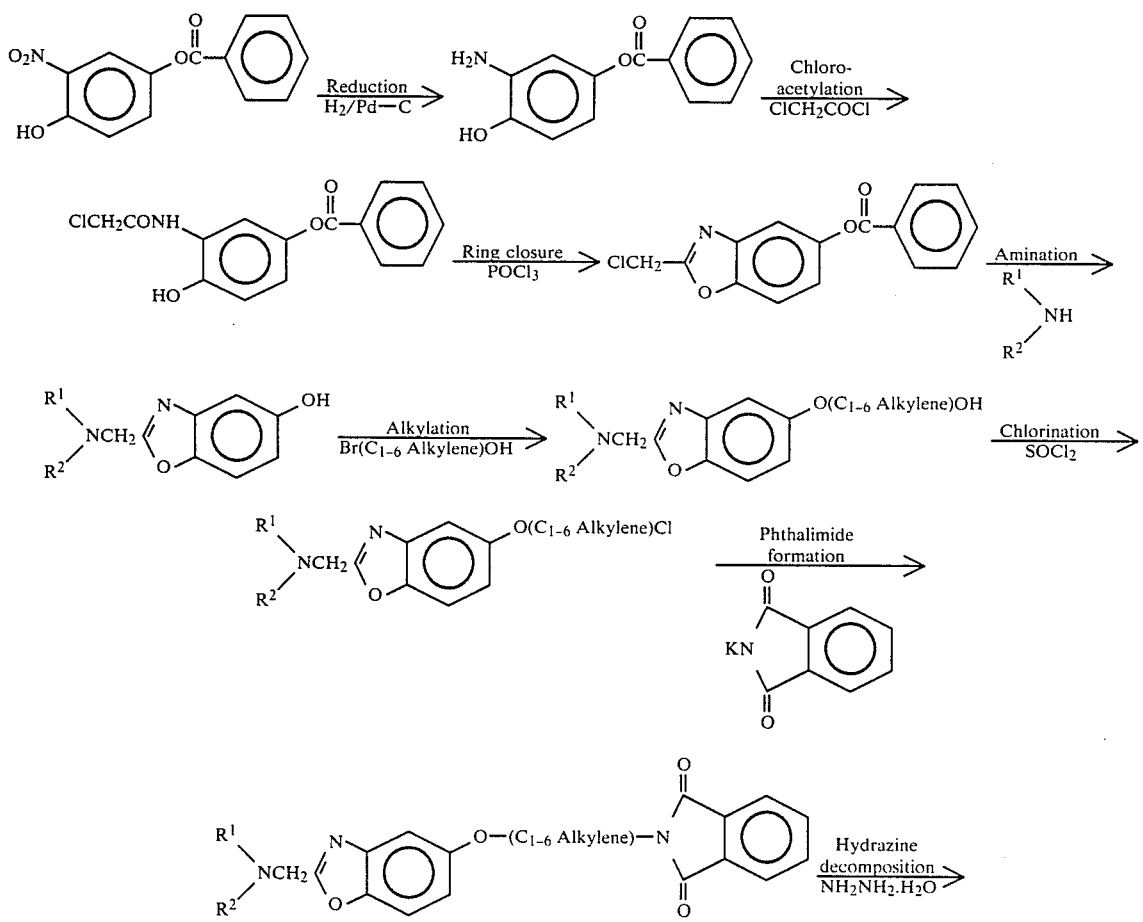

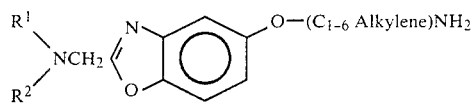
-continued
(I) 5-aminoalkylthio-2-substituted aminomethylbenzimidazole
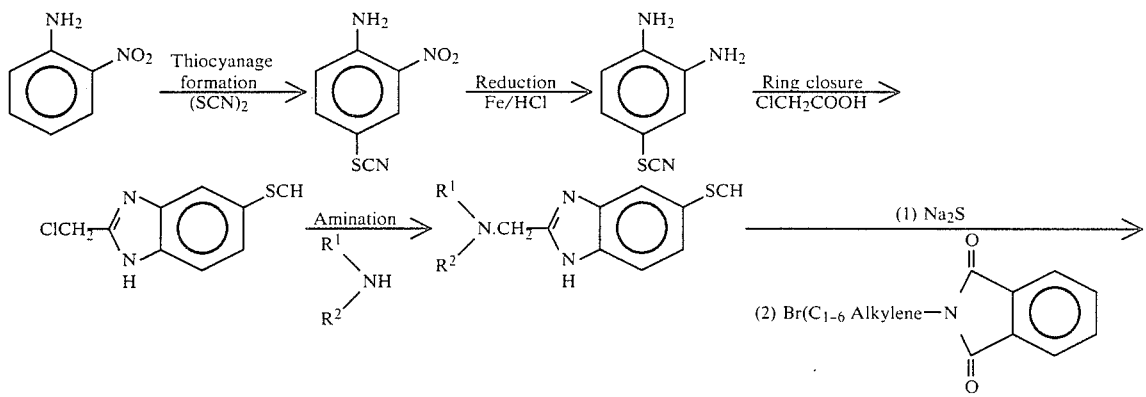
(J) 6-aminoalkylthio-2-substituted aminomethylbenzothiazole
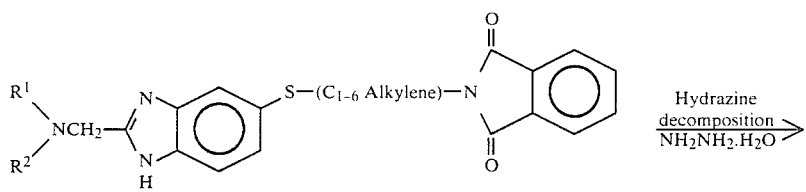
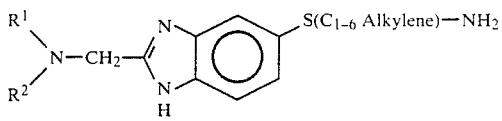
-continued
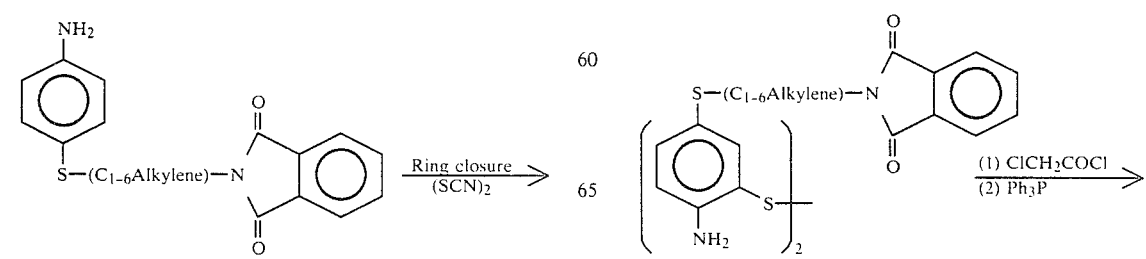

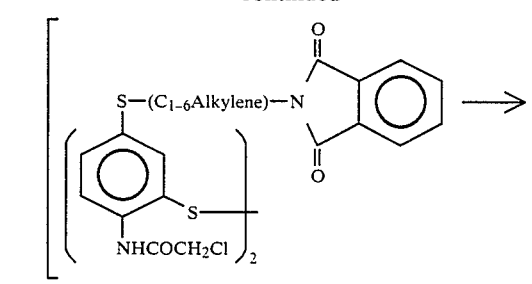
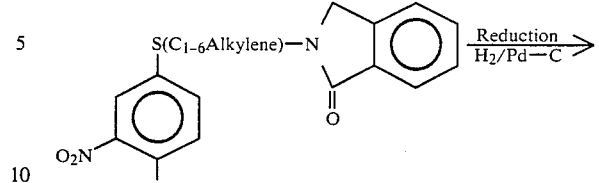
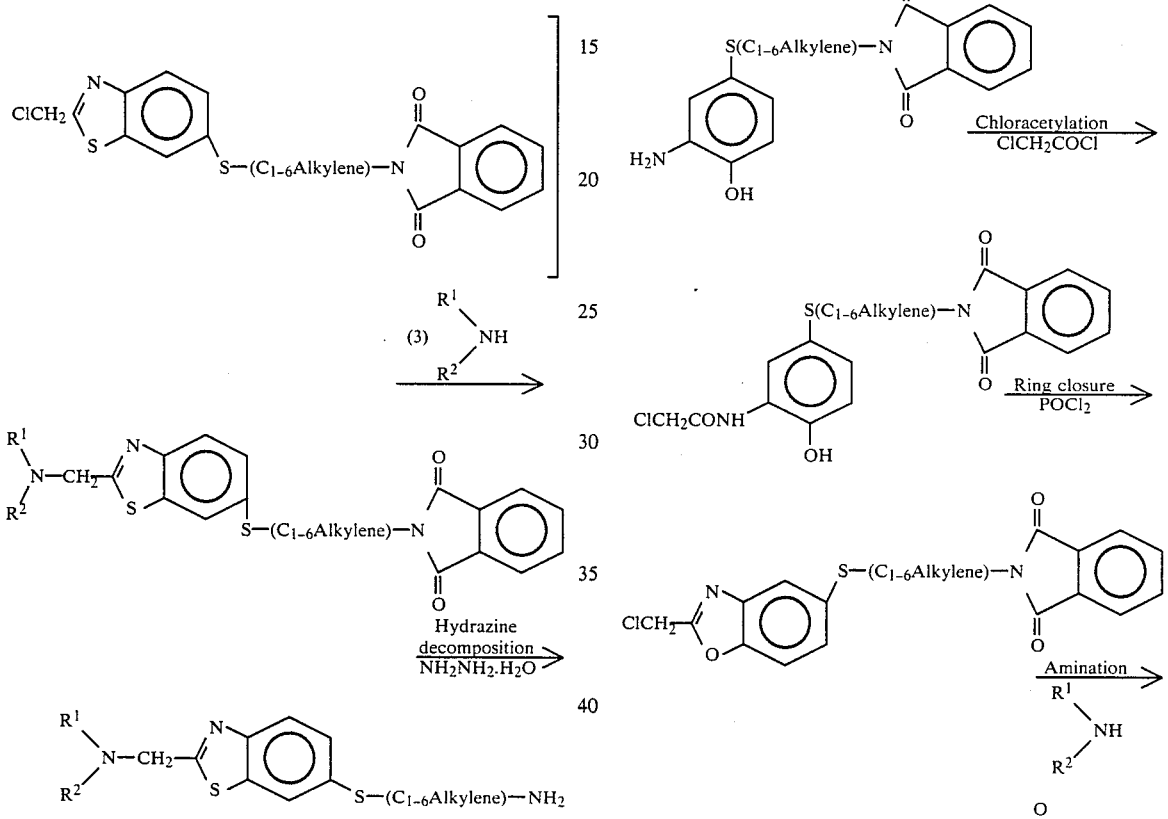
(K) 5-aminoalkylthio-2-substituted aminomethylbenzoxazole
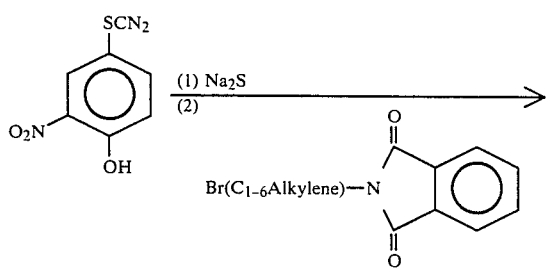
(L) 2-amino-5-aminoalkylthiobenzimidazole
(M) 2-amino-5-aminoalkylthiobenzoxazole
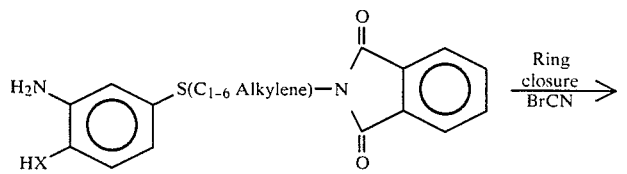

-continued
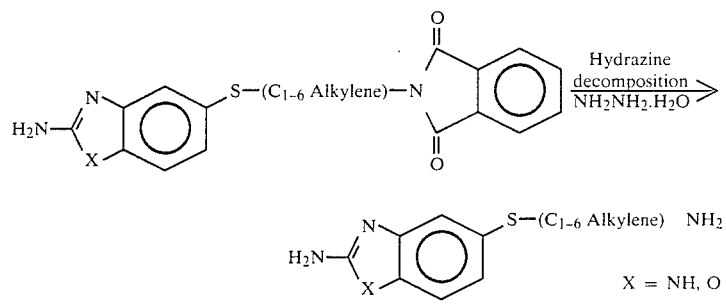
(N) 2-amino-6-aminoalkylthiobenzothiazole
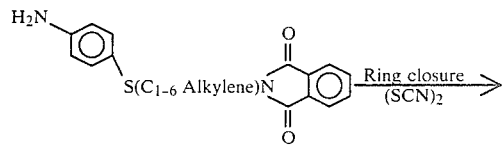
-continued
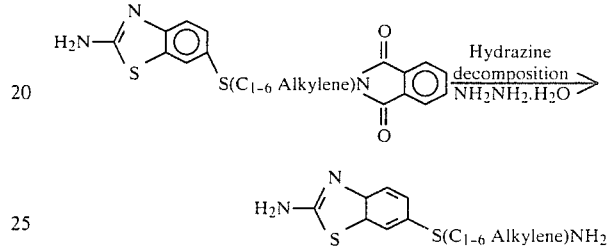
(O) 5-aminoalkyloxy-2-guanidinobenzimidazole and 5-aminoalkyloxy-2-guanidinobenzoxazole
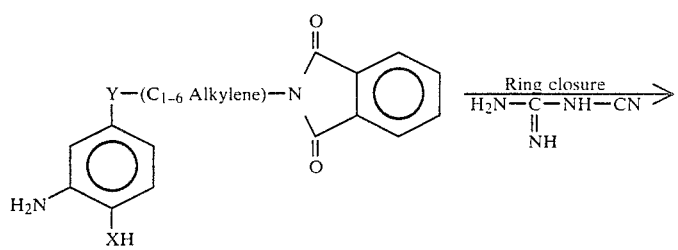
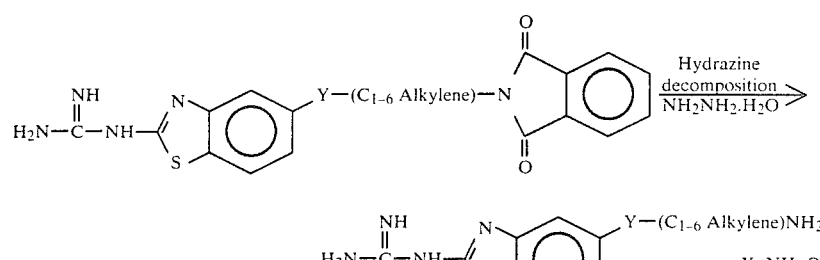
X: NH, O
Y: O, S
(P) 6-aminoalkyloxy-2-guanidinobenzothiazole
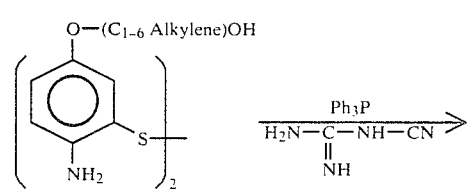
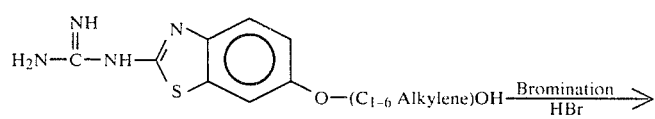

-continued

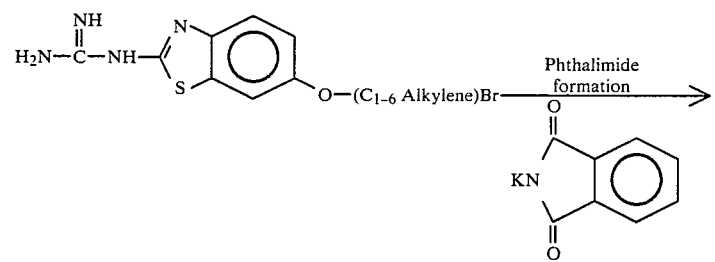
Phthalimide formation →

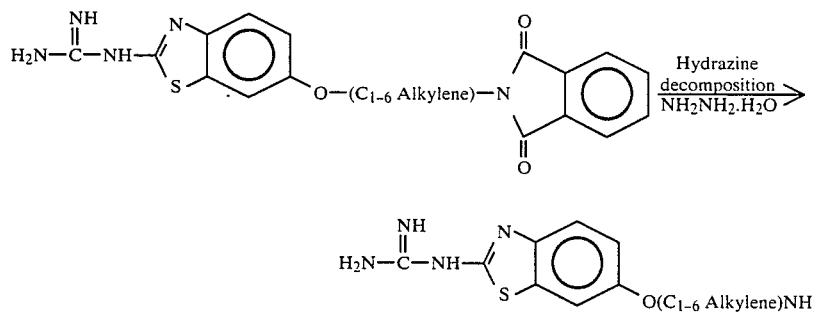
Hydrazine decomposition $\overrightarrow{NH_2NH_2 \cdot H_2O}$

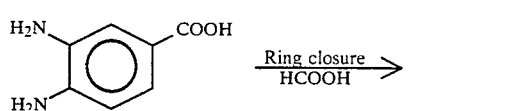

(Q) 5-aminoethylthiomethylbenzimidazole.2 hydrobromide

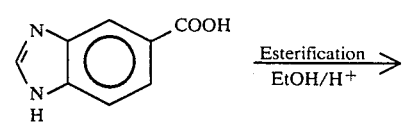
Ring closure / HCOOH →

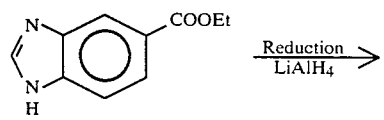
Esterification / EtOH/H⁺ →

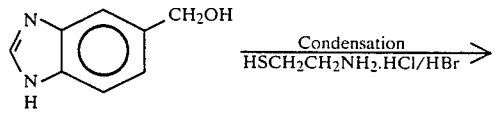
Reduction / LiAlH₄ →

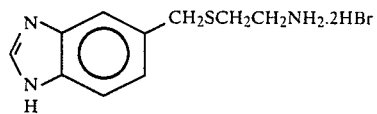
Condensation / HSCH₂CH₂NH₂·HCl/HBr →

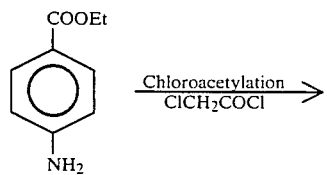

(R) 5-aminoalkylthiomethyl-2-substituted aminomethylbenzimidazole.3hydrobromide

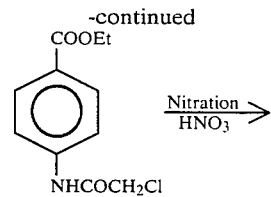
Chloroacetylation / ClCH₂COCl →

-continued

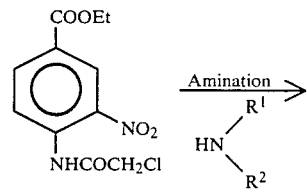
Nitration / HNO₃ →

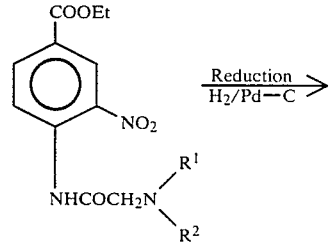
Amination / HN(R¹)(R²) →

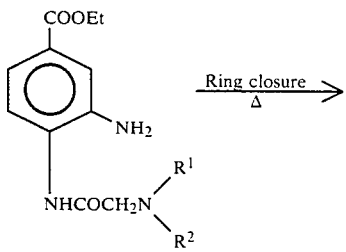
Reduction / H₂/Pd—C →

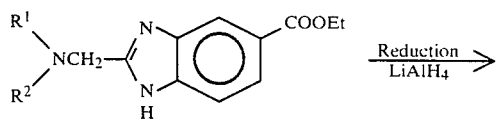
Ring closure / Δ →

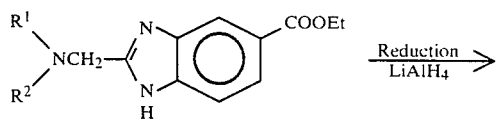
Reduction / LiAlH₄ →

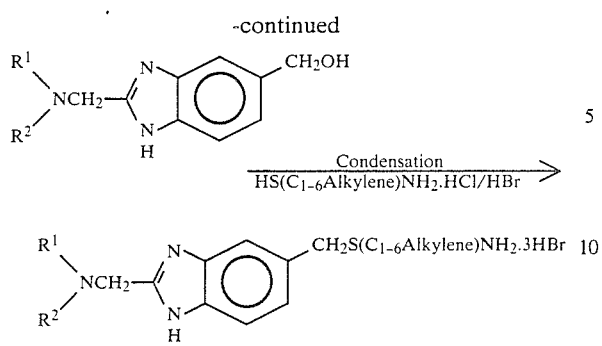
(S) 5-aminoethylthiomethyl-2-substituted aminomethylbenzothiazole.2hydrobromide
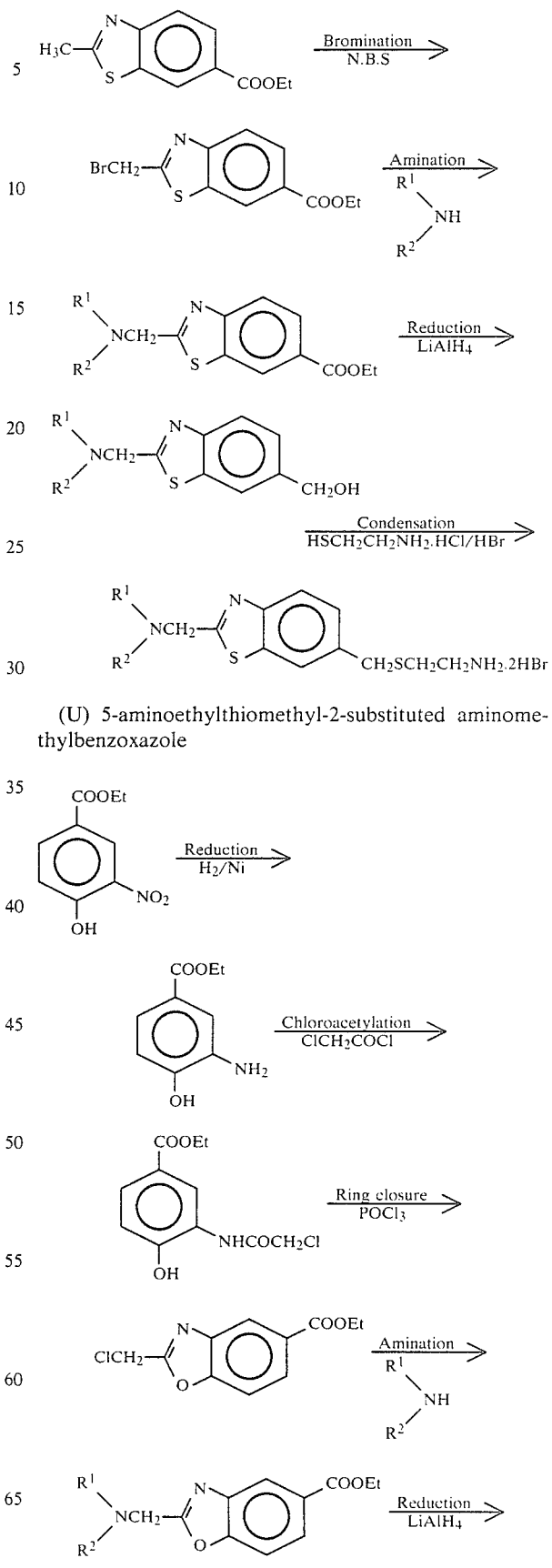
(T) 6-aminoethylthiomethyl-2-substituted aminomethylbenzothiazole.2 hydrobromide
(U) 5-aminoethylthiomethyl-2-substituted aminomethylbenzoxazole

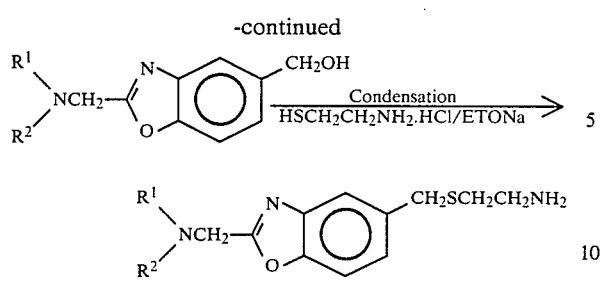
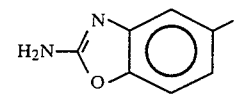
(V) 2-amino-5-aminoethylthiomethylbenzimidazole.3hydrobromide
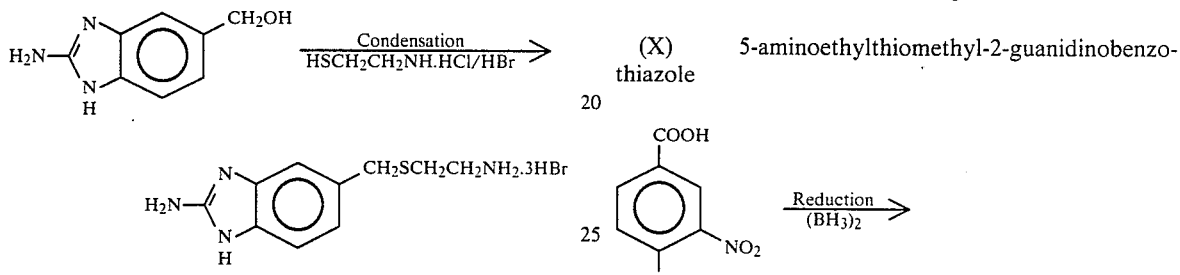
(W) 2-amino-5-aminoethylthiomethylbenzoxazole
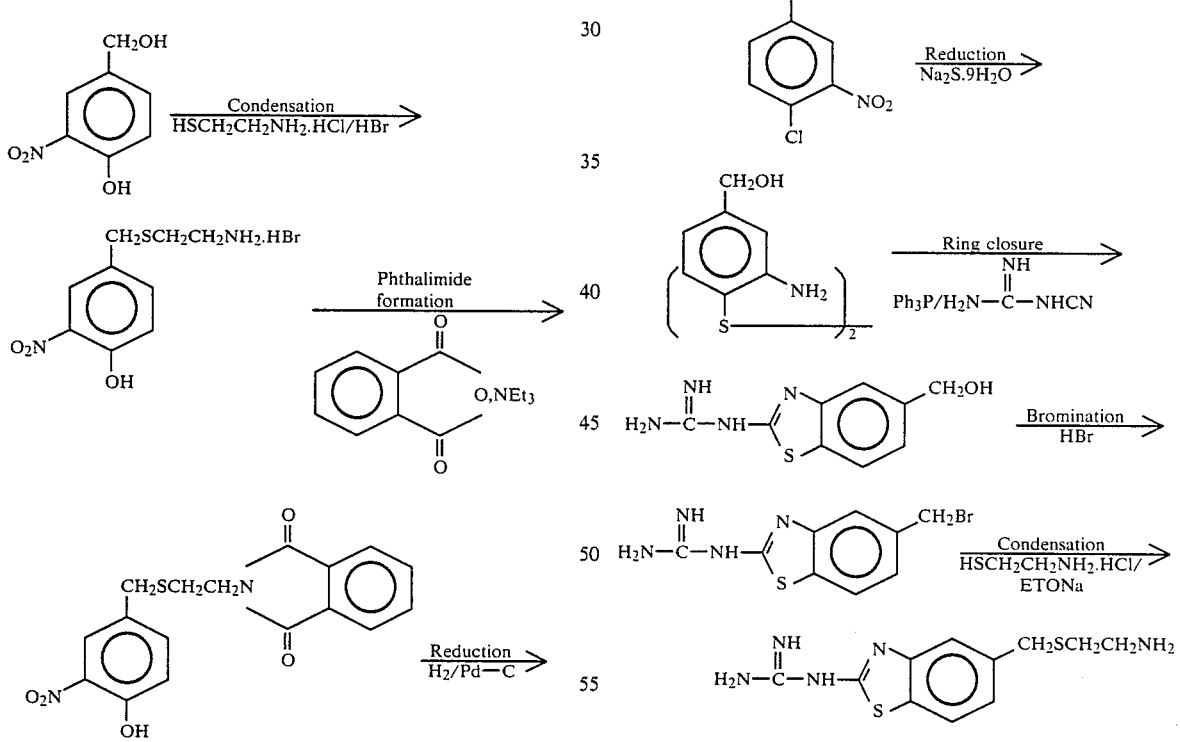
(X) 5-aminoethylthiomethyl-2-guanidinobenzothiazole
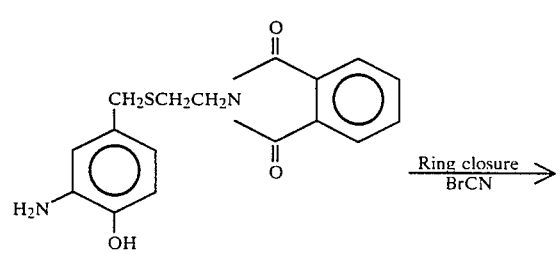
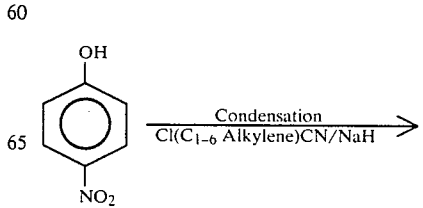
(Y) 5-cyanoalkyloxy-2-substituted aminomethylbenzimidazole

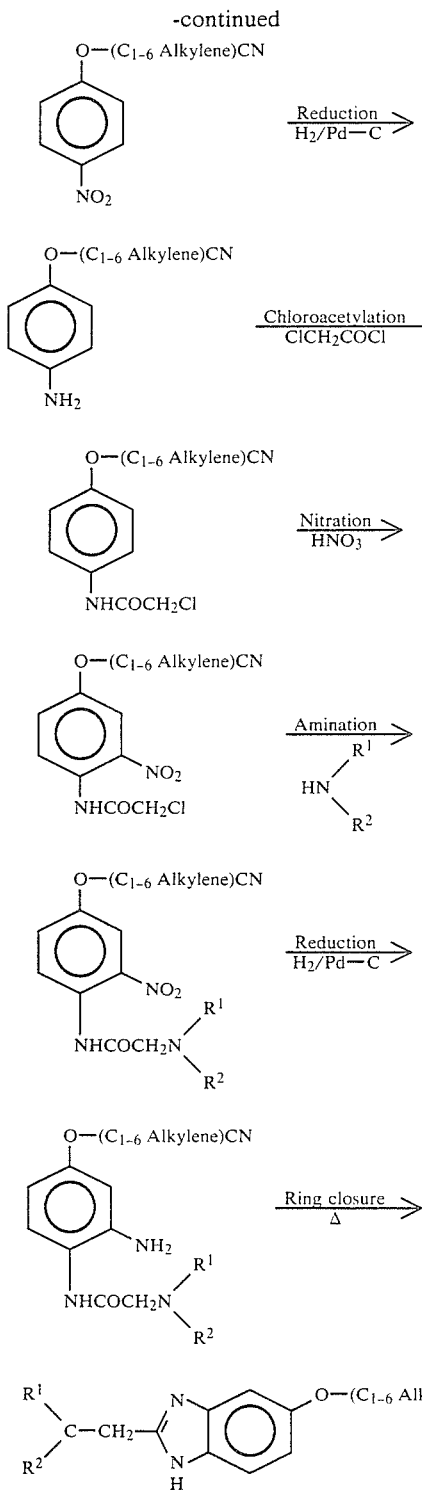

(Z) 5-cyanoalkylthiomethyl-2-substituted aminomethylbenzimidazole

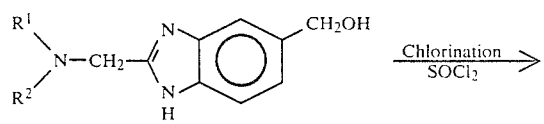

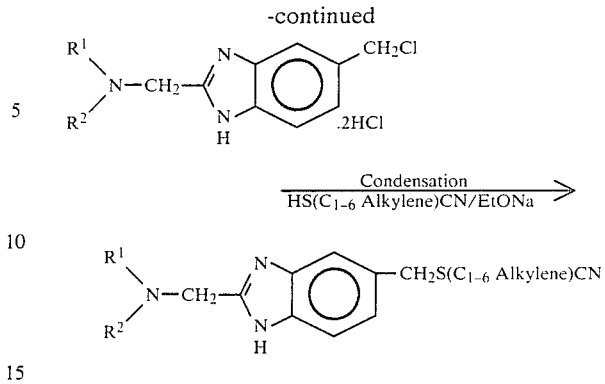

The medically allowable salts of the compounds of general formula (I) of the invention comprise acid addition salts. Suitable acids for the preparation of acid addition salts are for instance inorganic acids, such as hydrochloric acid, sulphuric acid, nitric acid or phosphoric acid and organic acids such as acetic acid, maleic acid, fumaric acid, tartaric acid, citric acid, succinic acid, or methanesulphonic acid. It will be understood that the acid used should be pharmaceutically acceptable.

The compounds of the invention are easily isolated and refined by conventional separating methods, such as precipitation, extraction, recrystallization, collumn chromatography and preparative thin-layer chromatography.

The compounds of the invention are useful as antipeptic ulcer agents, and they can be used as in the form of general preparations of pharmaceutical compositions together with usual pharmaceutically acceptable carriers. Examples of the pharmaceutically acceptable carriers which are used depending on the desired form of pharmaceutical compositions including diluents or excipients such as fillers, diluents, binders, wettable agents, disintegrators, surface-active agents and lubricants.

No particular restriction is made to the administration unit forms and the compositions can be selected from any desired unit form including tablets, pills, powders, liquors, suspensions, emulsions, granules, capsules, suppositories and injections (solutions, suspensions and the like).

For the purpose of shaping into the form of tablets, carriers which are widely used in the field can also be used, for example excipients such as lactose, sucrose, sodium chloride, glucose, urea, starch, calcium carbonate, caolin, crystalline cellulose, silicic acid and the like, binding agents such as water, ethanol, propanol, simple syrus, glucose solution, starch solution, gelatin solution, carboxymethyl cellulose, shelac, methyl cellulose, calcium phosphate and polyvinylpyrrolidone; desintegrators such as dried starch, sodium alginate, agar-agar powder, laminalia powder, sodium hydrogencarbonate, calcium carbonate, esters of polyoxyethylene sorbitan fatty acids, sodium laurylsulfate, monoglyceride of stearic acid, starch and lactose; desintegration inhibitors such as sucrose, stearin, coconut butter and hydrogenated oils; adsorption accelerators such as quaternary ammonium bases and sodium laurylsulfate; wetting agents such as glycerin and starch; adsorbing agents such as starch, lactose kaolin, bentonite and colloidal silicic acid; and lubricants such as purified talc, stearic acid salts, boric acid powder and polyethylene glycols.

In case of preparing tablets, they can be further coated with usual coating materials to make them into tablets coated with sugar, tablets coated with gelatin film, tablets coated with enteric coatings, tablets coated with films or double layer tablets as well as multiple layer tablets.

For the purpose of shaping into the form of pills, any carrier which is known and used widely in this field can be used, for example, excipients such as glucose, lactose, starch, coconut butter, hydrogenated vegetable oils, kaolin and talc; binders such as powdered gum arabi, powdered tragacanth gum, gelatin and ethanol; desintegrators such as laminaria and agar-agar are included.

For the purpose of shaping into the form suppositories, carriers which are known and widely used in this field can also be used, for example, polyethylene glycols, coconut butter, higher alcohols, esters of higher alcohols, gelatin semi-synthesized glycerides are included.

For the purpose of forming into injection preparations, colutions and suspensions are sterilized and are preferably made isotonic to the blood. In making injection preparations in the form of solutions, emulsions and suspensions, any carrier which is known and is widely used in this field can also be used, for example water, ethyl alcohol, propylene glycol, ethoxylated isostearyl alcohol, polyoxylated isostearyl alcohol and polyoxyethylene sorbitan fatty acid esters are included. In these instances, adequate amounts of sodium chloride, glucose or glycerin can be added to the desired injection preparations to make them isotonic. Furthermore, usual dissolving agents, buffers, analgesic agents can be added. Further, coloring materials, preservitives, perfumes, seasoning agents, sweetening agents and other medicines can also be added into the desired prepration, if necessary.

The amount of the compounds of the invention to be contained in the anti-peptic ulcer composition is not specifically restricted and it can suitably be selected from wide range, and is generally 1 to 70%, preferably 5 to 50% by weight of the whole composition.

The anti-peptic ulcer agent can be used in various forms of preparations depending on the age, sec, symptoms and other conditions without any restrictions. For example, tablets, pills, solutions, suspensions, emulsions, granules and capsules are administered orally; injection preparations are administered intravenously singly or mixed with usual injection transfusions such as glucose solutions and amino acid solutions; if necessary, the injection preparations are administered singly intramuscularly, intracutaneously, subcutaneously or intraperitoneally; suppositories are administered into the rectum.

The dosage of the present anti-peptic ulcer agent can be selected suitably according to the purpose of use, the age and sex of the patient, and other conditions, as well as the symptoms. There are generally administered pharmaceutical compositions containing 0.2 to 16 mg/kg of body weight/day of the compound of the general formula (1) or its salt. Further the active ingredient may be contained 5 to 500 mg in the administrative unit form.

EXAMPLE 1

(A)

5-[(3-aminopropyl)oxy]-2-dimethylaminomethylbenzimidazole

Sodium hydride (a 50% oil solution, 4.8 g) was added to p-hydroxyacetanilide (15.1 g) in N,N-dimethylformamide (45 ml) to prepare a sodium salt of p-hydroxyacetanilide.

Then, the product was caused to react with N-(3-bromopropyl)phthalimide (26.8 g) at room temperature for 2 hrs to yield N-[2-(p-acetamidephenoxy)propyl]phthalimide (mp 143.1° C., 20 g). The phthalimide derivative (20 g) was nitrated with nitric acid (specific gravity 1.42, 5.6 ml) in acetic acid (203 ml), and the nitrated product was hydrolyzed to yield N-[3-(4-amino-3-nitrophenoxy)propyl]phthalimide (mp 164° C, 16.2 g).

The nitro compound (13.6 g) was caused to react with chloroacetyl chloride (5 g) in tetrahydrofuran (500 ml) to yield N-[3-(4-chloroacetamide-3-nitrophenoxy)propyl]phthalimide (mp 177.3° C., 15.8 g). The chloroacetamide compound (10 g) was caused to react with excess dimethylamine to yield N-[3-(4-dimethylaminoacetamide-3-nitrophenoxy)propyl]phthalimide (mp 165° C., 8 g). The product (8 g) was subjected to reduction under increased pressure (70 atm) in tetrahydrofuran (56 ml) in the presence of a 5% palladium carbon catalyst, and subsequently to ring closure with heating in xylene (160 ml) to yield 2-dimethylaminomethyl-5-[3-<2-(1,3-(2H)-dioxo-1H-isoindolyl)>propyloxy]benzimidazole (light brown, oily product, 5.8 g). The benzimidazole derivative (3.78 g) was heated with hydrazine hydrate to yield a crude oily product, which was subjected to column chromatography by use of silica gel. From a ethyl acetate:methanol:aqueous ammonia (40:10:1) flow, 5-[(3-aminopropyl)oxy]-2-dimethylaminomethylbenzimidazole (2.2 g) was obtained as a light yellow oily product.

NMR(DMSO-$d_6$, ppm): 1.8–2.05 (2H, m), 2.2 (6H, s), 2.8–3.05 (2H, m), 3.57 (2H, s), 3.83–4.08 (2H, m), 5.5–5.8 (2H, b), 6.57–7.35 (3H, m).

(B)

N-cyano-N'-methyl-N''-[3-<5-(2-dimethylaminomethylbenzimidazolyl)oxy>propyl]guanidine To a methanol (20 ml) solution of dimethyldithiocyanoimidocarbonate (0.21 g) prepared according to the method described in Japanese Patent Publication No. 46-26482, was added 5-(3-aminopropoxy)-2-dimethylaminomethylbenzimidazole (0.36 g) prepared in (A) above. The mixture was agitated for 16 hrs at room temperature, and the solvent was evaporated to dryness to yield an oily product. Then, 40% methyl amine in methanol (5 ml) was added to the oily product, and the mixture was further agitated for 5 hrs at room temperature, and the solvent was distilled off under reduced pressure. The oily residue was subjected to column chromatography using a silica gel/ethyl acetate:ethanol:aqueous ammonia (200:40:1) mixture as a developer, and N-cyano-N'-methyl-N''-[3-<5-(2-dimethylaminomethylbenzimidazolyl)oxy>propyl]guanidine (0.38 g, 80% yield) was obtained as a light yellow, oily product.

IR (liq. $cm^{-1}$): 3300, 2960, 2170, 1600

NMR (CDCl$_3$, ppm): 1.80–2.0 (2H, m), 2.3 (6H, s), 2.75 (3H, d), 3.3–3.5 (2H, m), 3.65 (2H, s), 3.95 (2H, t), 5.8 (2H, b, disappeared by D$_2$O treatment), 6.6–7.4 (3H, m).

EXAMPLE 2

(A)
5-[(4aminobutyl)oxy]-2-dimethylaminomethylbenzimidazole

According to the method described in Example 1(A), the target compound was obtained by use of the necessary reaction reagents.
IR (liq. cm$^{-1}$): 1720
NMR (CDCl$_3$, ppm): 1.6–2.1 (4H, m), 2.30 (6H, s), 3.5–4.2 (4H, m), 3,69 (2H, s), 6.6–7.4 (3H, m), 7.4–7.9 (4H, m).

(B)
N-cyano-N'-methyl-N''-[4-<5-(2-dimethylaminomethylbenzimidazolyl)oxy>butyl]guanidine According to the method described in Example 1(B), the target compound was obtained by use of the compound of item (A) above and the necessary reaction reagents.
mp: 60°–64° C.
IR (KBr, cm$^{-1}$): 2150
NMR (DMSO-d$_6$, ppm): 1.49 (4H, b), 2.21 (6H, s), 3.20 (2H, b), 3.58 (2H, s), 3.91 (2H, b), 6.5–7.4 (5H, m).

EXAMPLE 3

(A)
5-(3-aminopropoxy)2-(1-pyrrolidinomethyl)benzimidazole

According to the method described in Example 1(A), the target compound was obtained by use of the necessary reaction reagents.
Oily product.
IR (liq. cm$^{-1}$): 3300–3000, 2980, 1635.
NMR (CDCl$_3$-CD$_3$OD, ppm): 1.7–2.0 (4H, m), 1.95–2.25 (2H, m), 2.3–2.7 (4H, m), 3.3–3.5 (2H, m), 3.8 (2H, s), 3.75–4.05 (2H, m), 6.6–7.4 (3H, m).

(B)
N-cyano-N'-methyl-N''-{3-[5-<]-(1-pyrrolidinomethyl)benzimidazolyl>oxy]propyl}guanidine According to the method described in Example 1(B), the target compound was obtained by use of the compound of item (A) and the necessary reaction reagents.
Oily product.
IR (liq. cm$^{-1}$): 3300, 2960, 2160, 1600
NMR (CDCl$_3$, ppm): 1.6–1.8 (4H, m), 1.9–2.1 (2H, m), 2.4–2.6 (4H, m), 2.70 (2H, d), 3.2–3.4 (2H, m), 3.8 (2H, s), 3.85–4.05 (2H, m), 5.70 (2H, b, disappeared by D$_2$O treatment), 6.5–7.4 (3H, m).

EXAMPLE 4

According to the method described in Example 1(A), 5-[(2-aminoethyl)oxy]-2-(1-piperidinomethyl)benzimidazole was obtained by use of the necessary reaction reagents. According to the method described in Example 1(B), N-cyano-N'-methyl-N''-{2-[5-<2-(1-piperidinomethyl)benzimidazolyl>oxy]ethyl}guanidine was obtained by use of the above product and the necessary reaction reagents.
IR (KBr, cm$^{-1}$): 3300, 2950, 2170, 1580, 1160, 1040, 960, 805.
NMR (DMSO-d$_6$-CDCl$_3$, ppm): 1.2–1.8 (6H, b), 2.2–2.6 (4H, b), 2.7 (3H, d), 3.3–3.8 (2H, b), 3.6 (2H, s), 3.8–4.2 (2H, t), 6.6–7.5 (3H, m), 6.8–7.0 (1H, b, disappeared by D$_2$O treatment), 8.2–8.7 (1H, b, disappeared by D$_2$O treatment).

EXAMPLE 5

(A)
5-(3-aminopropoxy)-2-(1-piperidinomethyl)benzimidazole

According to the method described in Example 1(A), the target compound was obtained by use of the reaction reagents required.
Oily product.
IR (liq. cm$^{-1}$): 3200, 2950, 1635, 1600.
NMR (DMSO-d$_6$, ppm): 1.4–1.7 (6H, m), 1.84–2.1 (2H, m), 2.4–2.7 (4H, m), 2.78–3.3 (2H, m), 3.7 (2H, s), 3.9–4.15 (2H, m), 6.65–7.42 (3H, m).

(B)
N-cyano-N'-methyl-N''-{3-[5-<2-(1-piperidinomethyl)benzimidazolyl>oxy]propyl}guanidine According to the method described in Example 1(B), the target compound was obtained by use of the compound of item (A) above and the necessary reaction reagents.
Oily product.
IR (liq. cm$^{-1}$): 3300, 2950, 2170, 1560.
NMR (CDCl$_3$, ppm): 1.3–1.7 (6H, m), 1.8–2.1 (2H, m), 2.2–2.5 (4H, m), 2.7 (3H, d), 3.2–3.4 (2H, m), 3.65 (2H, s), 3.8–4.0 (2H, m), 5.9 (2H, b, disappeared by D$_2$O treatment), 6.5–7.4 (3H, m), 8.4 (1H, b, disappeared by D$_2$O treatment).

EXAMPLE 6

(A)
5-[(4-aminobutyl)oxy]-2-(1-piperidinomethyl)benzimidazole

According to the method described in Example 1(A), 5-[4-<2-(1,3 (2H)-dioxo-1H-isoindolyl)>butyloxy]-2-(1-piperidinomethyl)benzimidazole was obtained by use of the necessary reaction reagents.
Oily product.
NMR (CDCl$_3$, ppm): 1.3–1.7 (6H, m), 1.6–2.1 (4H, m), 2.2–2.7 (4H, m), 3.5–4.3 (4H, m), 3.66 (2H, s), 6.1–7.4 (3H, m), 7.4–8.0 (4H, m).

The benzimidazole derivative was caused to react with hydrazine hydrate to yield the target compound.

(B)
N-cyano-N'-methyl-N''-{4-[5-<2-(1-piperidinomethyl)benzimidazolyl>oxy]butyl}guanidine According to the method described in Example 1(B), the target compound was obtained by use of the compound of item (A) above and the necessary reaction reagents.
mp: 57°–60° C.
IR (KBr, cm$^{-1}$): 3300, 2170.
NMR (DMSO-d$_6$, ppm): 1.2–1.7 (6H, m), 2.2–2.6 (4H, m), 2.41 (4H, m), 2.66 (3H, d), 3.14 (2H, m), 3.92 (2H, m), 6.5–7.4 (6H, m).

EXAMPLE 7

According to the method described in Example 1(A), 5-[(2-aminoethyl)oxy]-2-(4-morpholinomethyl)benzimidazole was obtained by use of the necessary reaction reagents. According to the method described in Example 1(B), N-cyano-N'-methyl-N''-{2-[5-<2-(4-morpholinomethyl)benzimidazolyl>oxy]ethyl}guanidine was obtained by use of the compound and the necessary reaction reagents.

IR (KBr, cm$^{-1}$): 3300, 2170, 1590, 1455, 1162, 1109, 860.

NMR (DMSO-d$_6$-CDCl$_3$, ppm): 2.3–2.6 (4H, m), 2.7 (3H, b), 3.30–3.70 (6H, b), 3.8–4.2 (2H, t), 6.55–7.4 (3H, m).

EXAMPLE 8

(A) 5-(3-aminopropoxy)-2-guanidinobenzimidazole

N-[3-(4-amino-3-nitrophenoxy)propyl]phthalamide (18 g) obtained as an intermediate product in the method of Example 1(A) was subjected to reduction under increased pressure at 70 atm in tetrahydrofuran (180 ml) in the presence of a 5% palladium carbon catalyst. Then, the reaction product was refluxed with heating for 2 hrs in a mixture of 1-cyanoguanidine (8.7 g) and 2% hydrochloric acid (187.6 ml). After adjustment of the pH of the solution to 8 with an aqueous 5% sodium bicarbonate solution, the precipitate was collected to obtain 5-[3-<2-(1,3-(2H)-dioxo-1H-isoindolyl)>-propoxy]-2-guanidinobenzimidazole (mp. 206.3° C., 11 g). The benzimidazole derivative (4 g) was heated with hydrazine hydrate to yield a crude crystalline product. The crude product was purified by silica gel column chromatography. From an ethyl acetate:methanol:ammonia (40:10:1) flow, 5-(3-aminopropoxy)-2-guanidinobenzimidazole (2.1 g) was obtained as a light yellow oily product.

NMR (DMSO-d$_6$, ppm): 1.65–1.9 (2H, m), 2.6–2.9 (2H, m), 3.75–4.05 (2H, m), 3.5–4.5 (6H, b, disappeared by D$_2$O treatment), 6.3–7.0 (3H, m).

(B) N-cyano-N'-methyl-N''-[3-<5-(2-guanidinobenzimidazolyl)oxy propyl] guanidine According to the method described in Example 1(B), the target compound was obtained by use of the above compound and the necessary reaction reagents.

IR (KBr, cm$^{-1}$): 3380, 2160, 1640.

NMR (CD$_3$OD-CDCl$_3$, ppm): 1.8–2.1 (2H, m), 2.75 (3H, s), 3.2–3.4 (2H, m), 3.8–4.1 (2H, m), 4.4–4.8 (6H, m, disappeared by D$_2$O treatment), 6.2 (1H, b, disappeared by D$_2$O treatment), 6.6–7.6 (3H, m).

EXAMPLE 9

According to Reaction formula diagram (P) described above, 6-[2-<2-(1,3-(2H)-dioxo-1H-isoindolyl)->ethyloxy]2-guanidinobenzothiazole was obtained by use of the necessary reaction reagents.

IR (KBr, cm$^{-1}$): 1740.

NMR (DMSO-d$_6$, ppm): 3.7–4.4 (4H, m), 6.6–7.4 (7H, m, 4H disappeared by D$_2$O treatment), 7.74 (4H, s).

The benzothiazole derivative was heated with hydrazine hydrate to yield 6-[(2-aminoethyl)oxy]-2-guanidinobenzothiazole.

According to the method described in Example 1(B), N-cyano-N'-methyl-N''-[2-<6-(2-guanidinobenzothiazolyl)oxy>ethyl] guanidine was obtained by use of the above compound and the necessary reaction reagents.

mp: 72°–75° C.

IR (KBr, cm$^{-1}$): 2150.

NMR (DMSO-d$_6$, ppm): 2.65 (2H, d), 3.1–3.8 (2H, m), 3.6–4.4 (2H, m), 6.5–7.4 (9H, m).

EXAMPLE 10

According to Reaction formula diagram (G) described above, 2-dimethylaminomethyl-6-[2-<2-(1,3-(2H)-dioxo-1H-isoindolyl)>ethyloxy]benzothiazole was obtained by use of the necessary reaction reagents.

mp: 150°–153° C.

IR (KBr, cm$^{-1}$): 1720.

NMR (CDCl$_3$, ppm): 2.35 (6H, s), 3.79 (2H, s), 4.15 (2H, t), 4.19 (2H, t), 6.8–7.9 (7H, m).

The benzothiazole derivative was heated with hydrazine hydrate to yield 6-[(2-aminoethyl)oxy]-2-dimethylaminomethylbenzothiazole.

According to the method described in Example 1(B), N-cyano-N'-methyl-N''-[2-<6-(2-dimethylaminomethylbenzothiazolyl)oxy>ethyl]guanidine was obtained by use of the above compound and the necessary reaction reagents.

mp: 46°–52° C.

IR (KBr, cm$^{-1}$): 2160.

NMR (CDCl$_3$, ppm): 2.34 (6H, s), 2.81 (3H, d), 3.4–3.9 (2H, m), 3.79 (2H, s), 4.06 (2H, t), 5.87 (1H, b, disappeared by D$_2$O treatment), 6.15 (1H, b, disappeared by D$_2$O treatment), 6.8–7.8 (3H, m).

EXAMPLE 11

According to reaction formula diagram (H) described above, 5-[(2-aminoethyl)oxy]-2-dimethylaminomethylbenzoxazole was obtained by use of the necessary reaction reagents.

Oily product.

IR (liq. cm$^{-1}$): 2950, 1615, 1575.

NMR (CD$_3$OD, ppm): 2.35 (6H, s), 2.81–3.20 (2H, m), 3.75 (2H, s), 4.03 (2H, t), 6.75–7.6 (3H, m).

According to the method described in Example 1(B), N-cyano-N'-methyl-N''-[2-<5-(2-dimethylaminomethylbenzoxazolyl)oxy>ethyl]guanidine was obtained by use of the above compound and the necessary reaction reagents.

mp: 37°–42° C.

IR (KBr, cm$^{-1}$): 2160.

NMR (CDCl$_3$, ppm): 2.36 (6H, s), 2.82 (3H, d), 3.44–3.87 (2H, m), 3.71 (2H, s), 3.87–4.27 (2H, t), 5.67–6.36 (2H, m, disappeared by D$_2$O treatment), 6.67–7.46 (3H, m).

EXAMPLES 12–14

According to reaction formula diagram (I), 3 types of compounds described below were obtained by use of the necessary reaction reagents:

5-[(2-aminoethyl)thio]-2-dimethylaminomethylbenzimidazole, 5-[(2-aminoethyl)thio]-2-(1-piperidinomethyl)benzimidazole, and 5-[(2-aminoethyl)thio]-2-(4-morpholinomethyl)benzimidazole.

According to the method described in Example 1(B), three types of compounds described below were obtained by use of the respective compounds mentioned above and the necessary reaction reagents.

N-cyano-N'-methyl-N''-[2-<5-(2-dimethylaminomethylbenzimidazolyl)thio>ethyl]guanidine.

IR (KBr, cm$^{-1}$): 3270, 2170, 1580, 1350, 1040, 840, 800

NMR (DMSO-d$_6$-CDCl$_3$, ppm): 2.28 (6H, s), 2.7 (3H, d), 2.8–3.5 (4H, m), 3.6 (2H, s), 6.5–7.0 (1H, b, disappeared by D$_2$O treatment), 7.0 –7.6 (3H, m).

N-cyano-N'-methyl-N''-{2-[5-<2-(1-piperidinomethyl)benzimidazolyl>thio]ethyl}guanidine.

IR (KBr, cm$^{-1}$): 3280, 2950, 2170, 1580, 1420, 1180, 1110, 1010, 920, 850, 800, 605.

NMR (DMSO-d$_6$-CDCl$_3$, ppm): 1.0–1.8 (6H, b), 2.2–2.6 (4H, b), 2.7 (3H, d), 2.7–3.6 (4H, m), 3.65 (2H, s), 5.1–6.5 (2H, b, disappeared by D$_2$O treatment), 6.6–7.0 (1H, b, disappeared by D$_2$O treatment), 7.0–7.6 (3H, m).

N-cyano-N'-methyl-N''-{2-[5-<2-(4-morpholinomethyl)benzimidazolyl>thio]ethyl}guanidine.

IR (KBr, cm$^{-1}$): 3280, 2170, 1570, 1420, 1290, 1180, 1000, 860, 800, 705, 605.

NMR (CDCl$_3$-DMSO-d$_6$, ppm): 2.3–2.6 (4H, b), 2.7 (3H, d), 2.7–3.5 (4H, b), 3.4–3.7 (4H, b), 3.7 (2H, s), 6.6–7.0 (1H, b, disappeared by D$_2$O treatment), 7.0–7.6 (3H, m).

EXAMPLE 15

According to reaction formula diagram (L) described above, 2-amino-5-[(2-aminoethyl)thio]benzimidazole was obtained by use of the necessary reaction reagents. According to the method described in Example 1(B), N-cyano-N'-methyl-N''-[2-<5-(2-aminobenzimidazolyl)thio>ethyl]guanidine was obtained by use of the above compound and the necessary reaction regents.

IR (KBr, cm$^{-1}$): 3350, 2160, 1580, 1460, 1370, 1270, 810.

NMR (CDCl$_3$-DMSO-d$_6$, ppm): 2.69 (3H, d), 2.75–3.50 (4H, m), 6.60–6.90 (2H, b, disappeared by D$_2$O treatment), 6.80–7.30 (3H, d).

EXAMPLE 16

(A) According to reaction formula diagram (O) described above, 5-[(2-aminoethyl)thio]-2-guanidinobenzimidazole was obtained by use of the necessary reaction reagents.

IR (liq. cm$^{-1}$): 3500–3100 (broad), 1630, 1460, 1280, 1030.

NMR (DMS)-d$_6$+CDCl$_3$, ppm): 2.7–3.0 (4H, b), 5.6–6.2 (6H, b, disappeared by D$_2$O treatment), 6.9–7.3 (3H, m, aromatic).

(B) According to the method described in Example 1(B), N-cyano-N'-methyl-N''-[2-<5-(2-quanidinobenzimidazoly)thio>ethyl]quanidine was obtained by use of the compound obtained in item (A) above and the necessary reaction reagents.

IR (KBr, cm$^{-1}$): 3350, 2180, 1590, 1520, 1450, 1270, 810, 560.

NMR (CDCl$_3$-DMSO-d$_6$, ppm): 2.70 (3H, d), 2.80–3.65 (4H, m), 6.4–7.05 (4–6H, b, disappeared by D$_2$O treatment), 7.0–7.4 (3H, m).

EXAMPLE 17

(A) According to reaction formula diagram (O) described above, 5-[(3-aminopropyl)thio]-2-guanidinobenzimidazole was obtained by use of the necessary reaction reagents.

IR (liq. cm$^{-1}$): 3400–3300 (broad), 1660, 1280, 1030.

NMR (DMSO-d$_6$+CDCl$_3$, ppm): 1.5–1.9 (2H, t), 2.55–2.9 (4H, q), 4.5–3.8 (6H, b, disappeared by D$_2$O treatment), 6.9–7.2 (3H, m, aromatic).

(B) According to the method described in Example 1(B), N-cyano-N'-methyl-N''-[3-<5-(2-guanidinobenzimidazolyl)thio>propyl]guanidine was obtained by use of the compound obtained in item (A) above and the necessary reaction reagents.

IR (liq. cm$^{-1}$): 3350, 2170, 1600.

NMR (CDCl$_3$-DMSO-d$_6$, ppm): 1.8–2.0 (2H, m), 2.75 (3H, d), 2.7–2.9 (2H, m), 3.0–3.3 (2H, m), 6.2–6.8 (6H, b, disappeared by D$_2$O treatment), 6.9–7.6 (3H, m).

EXAMPLES 18–20

According to reaction formula diagram (J), the following three types of compounds were obtained by use of the necessary reaction reagents.

2-dimethylaminomethyl-6-[2-<2-(1,3-(2H)-dioxo-1H-isoindolyl)>etylthio]benzothiazole.

mp: 98°–100° C.

IR (KBr, cm$^{-1}$): 1770, 1710, 1395.

NMR (CDCl$_3$, ppm): 2.35 (6H, s), 3.25 (2H, t), b 3.80 (2H, s), 3.90 (2H, t), 7.25–7.9 (7H, m).

6-[2-<2-(1,3-(2H)-dioxo-1H-isoindolyl)>ethylthio]-2-(1-piperidinomethyl)benzothiazole.

Yellow oily product.

IR (liq. cm$^{-1}$): 2950, 1775, 1720.

NMR (CDCl$_3$, ppm): 1.4–1.7 (6H, m), 2.4–2.65 (4H, m), 3.2 (2H, t), 3.75 (2H, s), 3.85 (2H, t), 7.1–7.8 (7H, m).

6-[(2-<2-(1,3-(2H)-dioxo-1H-isoindolyl)>ethylthio]-2-(4-morpholinomethyl)benzothiazole.

Light brown, oily product.

IR (liq. cm$^{-1}$): 1775, 1720.

NMR (CDCl$_3$, ppm): 2.5–2.7 (4H, m), 3.2 (2H, t), 3.6–3.8 (2H, m), 3.75 (2H, s), 3.9 (2H, s), 7.2–7.9 (7H, m).

According to the method described in Example 1(B), the following three types of compounds were obtained by use of unprotective derivatives of the respective compounds mentioned above and the necessary reaction reagents.

N-cyano-N'-methyl-N''-[2-<6-(2-dimethylaminomethylbenzothiazolyl)thio>ethyl]guanidine.

Oily product.

IR (liq. cm$^{-1}$): 3300, 2150, 1590.

NMR (CDCl$_3$, ppm): 2.30 (6H, s), 2.75 (3H, d), 3.0–3.25 (2H, m), 3.25–3.6 (2H, m), 3.75 (2H, s), 6.25 (2H, b, disappeared by D$_2$O treatment), 7.2–7.8 (3H, m).

N-cyano-N'-methyl-N''-{2-[6-<2-(1-piperidinomethyl)benzothiazolyl>thio]ethyl}guanidine.

Oily product.

IR (liq. cm$^{-1}$): 3300, 2150, 1590.

NMR (CDCl$_3$, ppm): 1.3–1.8 (6H, m), 2.3–2.7 (4H, m), 2.75 (3H, d), 3.0–3.55 (4H, m), 3.8 (2H, s), 6.0 (2H, b, disappeared by D$_2$O treatment), 7.2–7.8 (3H, m).

N-cyano-N'-methyl-N''-{2-[6-<2-(1-morpholinomethyl)benzothiazolyl>thio]ethyl}guanidine.

Oily product.

IR (liq. cm$^{-1}$): 3400, 2170, 1600.

NMR (CDCl$_3$, ppm): 2.5–2.7 (4H, m), 2.75 (3H, d), 3.15 (2H, t), 3.40 (2H, t), 3.6–3.8 (4H, m), 3.85 (2H, s), 5.9 (2H, b, disappeared by D$_2$O treatment), 7.2–7.8 (3H, m).

EXAMPLE 21

According to reaction formula diagram (N) above, 2-amino-6-[2-<2-(1,3-(2H)-dioxo-1H-isoindolyl)>ethylthio]benzothiazole was obtained by use of the necessary reaction reagents.

IR (KBr, cm$^{-1}$): 3430, 3210, 1770, 1710, 1630.

NMR (CDCl$_3$-DMSO-d$_6$, ppm): 3.15 (2H, t), 3.85 (2H, t), 6.95 (2H, s, disappeared by D$_2$O treatment), 7.2–7.8 (7H, m).

The benzothiazole derivative was heated with hydrazine hydrate to give 2-amino-6-[2-aminoethyl)thio]benzothiazole. According to the method described in Example 1(B), N-cyano-N'-methyl-N''-[2-<6-(2-aminobenzothiazolyl)thio>ethyl]guanidine was obtained by use of the above compound and the necessary reaction reagents.

Oily product.

IR (liq. cm$^{-1}$): 3300, 2150, 1590.

NMR (CDCl$_3$-DMSO-d$_6$, ppm): 2.65 (3H, d), 2.90–3.1 (2H, m), 3.25 (2H, t), 6.2 (2H, b, disappeared by D$_2$O treatment), 6.6 (2H, b, disappeared by D$_2$O treatment), 7.1–7.5 (3H, m).

EXAMPLE 22

According to reaction formula diagram (K) above, 5-[(2-aminoethyl)thio]-2-dimethylaminomethylbenzoxazole was obtained by use of the necessary reaction reagents.

IR (liq. cm$^{-1}$): 2960, 1610, 1570.

NMR (CD$_3$OD, ppm): 2.35 (6H, s), 2.70–3.20 (4H, m), 3.77 (2H, s), 7.34 (2H, s), 7.63 (1H, s).

According to the method described in Example 1(B), N-cyano-N'-methyl-N''-[2-<5-(2-dimethylaminomethylbenzoxazolyl)thio>ethyl]guanidine was obtained by use of above compound and the necessary reaction reagents.

mp: 38°–44° C.

IR (KBr, cm$^{-1}$): 2160.

NMR (CDCl$_3$, ppm): 2.37 (6H, s), 2.77 (3H, d), 2.93–3.57 (4H, m), 3.73 (2H, s), 5.75–6.26 (2H, m, disappeared by D$_2$O treatment), 7.29 (2H, s), 7.61 (1H, s).

EXAMPLE 23

A methanol solution (15 ml) containing sodium sulfide. 9 hydrate (3.60 g) was added to 2-nitro-4-thiocyanophenol (1.96 g), which was prepared according to the method described in U.S. Pat. No. 2,562,948 (1951), in dimethyl sulfoxide (10 ml). Then N-(2-bromoethyl)phthalimide (2.54 g) was added, and the mixture was agitated for 3 hrs at room temperature, and was poured into ice water. The pH of the solution was adjusted to 5 with diluted hydrochloric acid, and the precipitate was collected to obtain N-[2-(4-hydroxy-3-nitrophenylthio)ethyl]phthalimide (2.3 g). The compound (3.5 g) was subjected to reduction under increased pressure at 70 atm in the presence of a 5% palladium carbon catalyst, and was subsequently caused to react with cyanogen bromide to yield 2-amino-5-[2-<2-(1,3-(2H)-dioxo-1H-isoindolyl)>ethylthio]benzoxazole (2 g). The benzoxazole derivative (2 g) was heated with hydrazine hydrate to yield 2-amino-5-(2-aminoethylthio)benzoxazole (1.1 g).

IR (KBr, cm$^{-1}$): 3375, 3300, 1690, 1570.

NMR (CD$_3$OD, ppm): 2.7–3.1 (4H, m), 7.05 (2H, s), 7.23 (1H, s).

According to the method described in Example 1(B), N-cyano-N'-methyl-N''-[2-<5-(2-aminobenzoxazolyl)-thio>ethyl]guanidine was obtained by use of the above compound and the necessary reaction reagents.

mp: 148°–175° C.

IR (KBr, cm$^{-1}$): 2160, 1690.

NMR (CDCl$_3$-DMSO-d$_6$, ppm): 2.71 (3H, d), 2.85–3.52 (4H, m), 6.55–7.30 (7H, m).

EXAMPLE 24

According to reaction formula diagram (O) above, 5-[2-<2-(1,3-(2H)-dioxo-1H-isoindolyl)>ethylthio]-2-guanidinobenzoxazole was obtained by use of the necessary reaction reagents.

IR (KBr, cm$^{-1}$): 3450, 3130, 1770, 1710, 1645.

NMR (CDCl$_3$-DMSO-d$_6$, ppm): 3.12 (2H, t), 3.80 (2H, t), 6.8–7.1 (7H, m, 4H disappeared by D$_2$O treatment), 7.58 (4H, s).

According to the method described in Example 1(B), N-cyano-N'-methyl-N''-[2-<5-(2-guanidinobenzoxazolyl)thio>ethyl]guanidine was obtained by use of an unprotective derivative of the above compound and the necessary reaction reagents.

mp: 89°–101° C.

IR (KBr, cm$^{-1}$): 2160.

NMR (CDCl$_3$-DMSO-d$_6$, ppm): 2.70 (3H, d), 2.85–3.55 (4H, m), 6.46–7.34 (9H, m).

EXAMPLE 25

(A) According to the method described in Example 1(A), 5-[(2-aminoethyl)oxy]-2-(1-pyrrolidinomethyl)-benzimidazole was obtained by use of the necessary reaction reagents.

IR (liq. cm$^{-1}$): 3210, 2920, 1440, 1060.

(B) According to the method described in Example 1(B), 1-nitro-2-methylamino-2-[2-<5-(2-(1-pyrrolidinomethyl)benzimidazolyl)oxy>ethylamino]ethylene was obtained by use of 1,1-bis(methylthio)-2-nitroethylene prepared according to the method described in Chem. Ber. vol. 100, pp 591 (1967) and Acta. Chem. Scad., vol. 21, pp 2797 (1967) in place of dimethyldithiocyanoimidocarbonate, and 5-[(2-aminoethyl)oxy]-2-(1-pyrrolidinomethyl)benzimidazole prepared in item (A) above in place of 5-(3-aminopropoxy)-2-dimethylaminomethylbenzimidazole.

Oily product.

IR (liq. cm$^{-1}$): 1610, 1580, 1440.

NMR (CDCl$_3$-DMSO-d$_6$, ppm): 1.5–1.9 (4H, m), 2.4–2.7 (4H, m), 2.80 (3H, s), 3.4–3.6 (2H, m), 3.80 (2H, s), 3.9–4.1 (2H, m), 6.55 (1H, s), 6.55–7.4 (3H, m).

EXAMPLES 26–31

According to the method described in Example 25(B), the following compounds were obtained by use of 5-[(2-aminoethyl)oxy]-2-dimethylaminomethylbenzimidazole prepared by use of the necessary reaction reagents according to the method described in Example 1(A), 5-[(3-aminopropyl)oxy]2-dimethylaminomethylbenzimidazole obtained in Example 1(A), 5-(3-aminopropoxy)-2-(1-pyrrolidinomethyl)benzimidazole obtained in Example 3(A), 5-(3-aminopropoxy)-2-(1-piperidinomethyl)benzimidazole obtained in Example 5(A), 5-[(4-aminobutyl)oxy]-2-(1-piperidinomethyl)benzimidazole obtained in Example 6(A), and 5-[(3-aminopropyl)thio]-2-guanidinobenzimidazole obtained in Examine 17(A), respectively, and the necessary reaction reagents.

(Example 26)

1-nitro-2-methylamino-2-[2-<5-(2-dimethylaminomethylbenzimidazolyl)oxy>ethylamino]ethylene.

IR (KBr, cm$^{-1}$): 1620, 1580, 1420.

NMR (CDCl$_3$-DMSO-d$_6$, ppm): 2.25 (6H, s), 2.80 (3H, d), 3.4–3.6 (2H, m), 3.65 (2H, s), 3.9–4.15 (2H, m), 6.5 (1H, s), 6.6–7.4 (3H, m).

(Example 27)

1-nitro-2-methylamino-2-[3-<5-(2-dimethylaminomethylbenzimidazolyl)oxy>-propylamino]ethylene.

Oily product.

IR (liq. cm$^{-1}$): 1610, 1580, 1440.

NMR (CDCl$_3$, ppm): 1.9–2.1 (2H, m), 2.30 (6H, s), 2.75 (3H, d), 3.3–3.5 (2H, m), 3.70 (2H, s), 3.8–4.05 (2H, m), 6.20 (2H, b, disappeared by D$_2$O treatment), 6.50 (1H, s), 6.6–7.4 (3H, m).

(Example 28)

1-nitro-2-methylamino-2-[3-<5-(2-(1-pyrrolidinomethyl)benzimidazolyl)oxy>propylamino]ethylene.

Oily product.

IR (liq. cm$^{-1}$): 1610, 1580, 1440.

NMR (CDCl$_3$-CD$_3$OD, ppm): 1.7–1.9 (4H, m), 1.95–2.15 (2H, m), 2.5–2.7 (4H, m), 2.8 (3H, s), 3.2–3.5 (2H, m), 3.80 (2H, s), 3.9–4.1 (2H, m), 6.50 (1H, s), 6.6–7.4 (3H, m).

(Example 29)

1-nitro-2-methylamino-2-{3-[5-<2-(1-piperidinomethyl)benzimidazolyl>oxy]propylamino)ethylene.

Oily product.

IR (liq. cm$^{-1}$): 1630, 1580.

NMR (CDCl$_3$-DMSO-d$_6$, ppm): 1.35–1.7 (6H, m), 1.9–2.1 (2H, m), 2.3–2.55 (4H, m), 2.75 (3H, d), 3.2–3.45 (2H, m), 3.65 (2H, s), 3.8–4.0 (2H, m), 6.5 (1H, s), 6.6–7.4 (3H, m), 9.0 (3H, b, disappeared by D$_2$O treatment).

(Example 30)

1-nitro-2-methylamino-2-{4-[5-<2-(1-piperidinomethyl)benzimidazolyl>oxy]butylamino}ethylene.

mp: 73°–77° C.

IR (KBr, cm$^{-1}$): 3200, 2920, 1575, 1380.

NMR (DMSO-d$_6$, ppm): 1.3–2.0 (10H, m), 2.2–2.7 (4H, m), 2.79 (3H, d), 3.1–3.4 (2H, m), 3.8–4.1 (2H, m), 6.42 (1H, s), 6.5–7.4 (3H, m).

(Example 31)

1-nitro-2-methylamino-2-[3-<5-(2-guanidinobenzimidazolyl)thio>propylamino]ethylene.

Oily product.

IR (liq. cm$^{-1}$): 1510, 1450.

NMR (CDCl$_3$-DMSO-d$_6$, ppm): 1.65–1.9 (2H, m), 2.7 (3H, d), 2.6–2.8 (2H, m), 3.1–3.3 (2H, m), 6.40 (1H, s), 6.70 (2H, b, disappeared by D$_2$O treatment), 6.9–7.3 (3H, m).

EXAMPLE 32

According to a method similar to that described in Zhur. Obschei Khim., vol. 32, pp 835–41 (1953), 3,4-diaminobenzoic acid was prepared. A formic acid solution (200 ml) of 3,4-diaminobenzoic acid (8 g) thus prepared was refluxed for 4 hrs to yield 5-carboxybenzimidazole.hydrochloride (8.9 g). The carboxylic acid (8.9 g) was refluxed with heating for 3.5 hrs in a mixture of sulfuric acid (4 ml) and absolute ethanol (140 ml) to yield 5-ethoxycarbonylbenzimidazole (mp. 93°–94° C., 7.8 g). An anhydrous tetrahydrofuran solution (20 ml) of the ester (7.5 g) was added to an anhydrous tetrahydrofuran suspension (50 ml) of lithium aluminium hydride (6.5 g) while cooling. The mixture was stirred for 3 hrs at room temperature to yield 5-hydroxymethylbenzimidazole (mp. 128.4° C., 3.62 g). A 47% aqueous hydrobromic acid solution (33 ml) containing the benzimidazole derivative (2.2 g) and cysteamine hydrochloride (1.9 g) was refluxed with heating for 7 hrs to yield 5-[(2-aminoethyl)thiomethyl]benzimidazole.2 hydrobromide (mp. 224°–225° C., 4.2 g).

IR (KBr, cm$^{-1}$): 3100, 3000, 1620, 1600.

NMR (DMSO-d$_6$, ppm): 2.6–3.2 (4H, m), 4.0 (2H, s), 7.4–7.85 (3H, m), 7.7–8.2 (3H, b, disappeared by D$_2$O treatment), 9.55 (1H, s).

(B) A methanol solution (50 ml) containing 5-[(2-aminoethyl)thiomethyl]benzimidazole.dihydrobromide (4.2 g) prepared in item (A) above, dimethyl dithiocyanoimidocarbonate (1.75 g) and potassium carbonate (1.65 g) was agitated for 16 hrs at room temperature. After removal of the solid component, the solvent was distilled off. Then, a 20% methylamine in methanol (45 ml) was added to the residue, and the mixture was agitated for 16 hrs at room temperature. The solvent was distilled off under reduced pressure, and the oily residue was subjected to column chromatography using silica gel as a filler and an ethyl acetate/methanol (7:1) mixture as a developer. Then, N-cyano-N'-methyl-N''-[2-(5-benzimidazolylmethylthio)ethyl]guanidine (mp. 191.4° C., 2.46 g, 75%) was obtained.

IR (KBr, cm$^{-1}$): 3290, 2190, 1595.

NMR (DMSO-d$_6$, ppm): 2.4–2.7 (2H, m), 2.7 (3H, d), 3.25 (2H, t), 3.8 (2H, s), 6.6–7.95 (7H, m, 3H disappeared by D$_2$O treatment).

EXAMPLE 33

2-amino-5-hydroxymethylbenzimidazole (2.5 g) prepared according to the method described in Ger. offen. 2,528,846 (1976) and an aqueous 47% hydrobromic acid solution (25 ml) of cysteamine hydrochloride (1.3 g) were subjected to refluxing with heating for five hrs thereby to yield 2-amino-5-[(2-aminoethyl)thiomethyl]-benzimidazole.3hydrobromate (melting point: 262°–265° C. (decomposition), 3 g).

IR (KBr, cm$^{-1}$): 3300, 3100, 1680, 1585, 1500.

NMR (DMSO-d$_6$, ppm): 2.5–3.0 (4H, m), 3.82 (2H, s), 6.9–7.35 (4H, m, 1H disappeared by D$_2$O treatment), 7.55–8.05 (2H, b, disappeared by D$_2$O treatment), 8.15–8.35 (2H, b, disappeared by D$_2$O treatment).

According to the method described in Example 32(B), N-cyano-N'-methyl-N''-[2-<5-(2-aminobenzimidazolyl)methylthio>ethyl]guanidine was obtained by use of the above product and the necessary reaction reagents.

mp: 47.3° C., IR (KBr, cm$^{-1}$): 3300, 2160, 1580.

NMR (DMSO-d$_6$, ppm): 2.3–2.6 (2H, m), 2.65 (3H, d), 3.2–3.4 (2H, m), 3.7 (2H, s), 6.0–6.3 (4H, b, disappeared by D$_2$O treatment), 6.7–7.1 (4H, m, 1H disappeared by D$_2$O treatment).

EXAMPLES 34–48

The following new compounds were obtained by use of the method described in J. Indian. Chem. Soc., vol. 15, pp. 152–159 (1938):

5-ethoxycarbonyl-2-dimethylaminomethylbenzimidazole 5-ethoxycarbonyl-2-(1-piperidinomethyl)benzimidazole 5-ethoxycarbonyl-2-(4-morpholinomethyl)benzimidazole The following intermediate products A–E were obtained by providing treatment to these compounds according to Example 1(A):

Intermediate Product A

5-[(2-aminoethyl)thiomethyl]-2-dimethylaminomethylbenzimidazole.3hydrobromide mp: 238.3° C., IR (KBr, cm$^{-1}$): 2750–2450, 1620.

NMR (DMSO-d$_6$, ppm): 2.64–3.1 (4H, m), 2.96 (6H, s), 3.96 (2H, s), 4.80 (2H, s), 7.35–7.8 (3H, m), 8.0–8.50 (3H, b, disappeared by D$_2$O treatment).

Intermediate Product B

5-[(2-aminoethyl)thiomethyl]-2-(1-piperidinylmethyl)-benzimidazole.3hydrobromide mp: 225.1° C., IR (KBr, cm$^{-1}$): 3000, 2800–2500, 1620, 1600.

NMR (DMSO-d$_6$, ppm): 1.65–2.0 (6H, m), 2.55–3.23 (4H, m), 3.97 (4H, m), 4.0 (2H, s), 4.72 (2H, s), 7.25–8.2 (6H, m, 3H disappeared by D$_2$O treatment).

Intermediate Product C

5-[(2-aminoethyl)thiomethyl]-2-(4-morpholinomethyl)-benzimidazole.3hydrobromide mp: 235.5° C., IR (KBr, cm$^{-1}$): 3060, 2990, 2850, 2560, 1620.

NMR (DMSO-d$_6$, ppm): 2.6–3.1 (4H, m), 3.2–3.5 (4H, M), 3.7–4.05 (6H, m), 4.7 (2H, s), 7.3–8.1 (6H, m, 3H disappeared by D$_2$O treatment).

Intermediate Product D

5-[(3-aminopropyl)thiomethyl]-2-dimethylaminomethylbenzimidazole

Oily product,

IR (liq, cm$^{-1}$): 3400–3100, 2950, 1620.

Intermediate Product E

5-[(3-aminopropyl)thiomethyl]-2-(1-piperidinomethyl)-benzimidazole

Oily product,

IR (liq, cm$^{-1}$): 3400–3200, 2950, 1625.

According to the method described in Example 32(B), the following various compounds were obtained using any one of the aforementioned intermediate products A–E and the necessary reaction reagents. Figures in parentheses following the name of each compound indicates the starting material.

(Example 34)

N-cyano-N'-[2-<5-(2-dimethylaminomethylbenzimidazolyl)methylthio>ethyl]guanidine (Intermediate product A).

Oily product,

IR (liq, cm$^{-1}$): 2180, 1630, 1560.

NMR (CDCl$_3$-DMSO-d$_6$, ppm): 2.30 (6H, s), 2.55 (2H, t), 3.35 (2H, t), 3.70 (2H, s), 3.80 (2H, s), 6.30 (2H, b, disappeared by D$_2$O treatment), 6.8–7.55 (3H, m), 7.9 (1H, b, disappeared by D$_2$O treatment).

(Example 35)

N-cyano-N'-methyl-N''-[2-<5-(2-dimethylaminomethylbenzimidazolyl)methylthio>ethyl]guanidine (Intermediate product A).

mp: 45.8° C.,

IR (KBr, cm$^{-1}$): 3300, 3150, 2950, 2170, 1580.

NMR (DMSO-d$_6$, ppm): 2.2 (6H, s), 2.4–2.6 (2H, m), 2.65 (3H, d), 3.15–3.45 (2H, m), 3.6 (2H, s), 3.84 (2H, s), 6.75–8.05 (2H, b, disappeared by D$_2$O treatment), 7.1–7.5 (3H, m), 11.9–12.1 (1H, b, disappeared by D$_2$O treatment).

(Example 36)

N-cyano-N',N'-dimethyl-N''-[2-<5-(2-dimethylaminomethylbenzimidazolyl)methylthio>ethyl]-guanidine (Intermediate product A).

Oily product,

IR (liq. cm$^{-1}$): 2160, 1590.

NMR (CDCl$_3$, ppm): 2.30 (6H, s), 2.60 (2H, t), 2.95 (6H, s), 3.4–3.6 (2H, m), 3.70 (2H, s), 6.0 (2H, b, disappeared by D$_2$O treatment), 6.95–7.6 (3H, m), 9.6 (1H, b, disappeared by D$_2$O treatment).

(Example 37)

N-cyano-N'-methyl-N''-[3-<5-(2-dimethylaminomethylbenzimidazolyl)methylthio>propyl]guanidine (Intermediate D).

IR (liq, cm$^{-1}$): 2160.

NMR (DMSO-d$_6$, ppm): 1.5–2.1 (2H, m), 2.2–2.8 (2H, m), 2.25 (6H, s), 2.68 (3H, d), 3.0–3.4 (2H, m), 3.62 (2H, s), 3.76 (2H, s), 6.7 (2H, b, disappeared by D$_2$O treatment), 6.8–7.4 (3H, m).

(Example 38)

N-cyano-N'-methyl-N''-[2-<5-(2-(1-piperidinomethyl)benzimidazolyl)methylthio<ethyl]guanidine (Intermediate product B).

mp: 82.7° C.,

IR (KBr, cm$^{-1}$): 3300, 2170, 1590

NMR (DMSO-d$_6$, ppm): 1.38–1.63 (6H, m), 2.35–2.65 (6H, m), 2.7 (3H, d), 3.2–3.4 (2H, m), 3.60 (2H, s), 3.80 (2H, s), 6.7–6.9 (2H, b, disappeared by D$_2$O treatment), 7.0–7.5 (3H, m).

(Example 39)

N-cyano-N'-methyl-N''-{3-[5-<2-(1-piperidinomethyl)benzimidazolyl>methylthio]propyl}guanidine (Intermediate product E).

mp: 62°–4° C.,

IR (KBr, cm$^{-1}$): 2170.

NMR (DMSO-d$_6$, ppm): 1.2–1.7 (6H, m), 2.1–2.6 (4H, m), 2.66 (3H, d), 3.62 (2H, s), 3.76 (2H, s), 6.7 (2H, b, disappeared by D$_2$O treatment), 6.8–7.4 (3H, m).

(Example 40)

N-cyano-N-methyl-N''-{2-[5-<2-(4-morpholinomethyl)benzimidazolyl>methylthio]ethyl}guanidine (Intermediate product C).

mp: 63.1° C., KR (KBr, cm$^{-1}$): 3300, 2170, 1590.

NMR (DMSO-d$_6$, ppm): 2.3–2.6 (6H, m), 2.68 (3H, d), 3.25–3.7 (6H, m), 3.68 (2H, s), 3.80 (2H, s), 6.7–6.9 (2H, b, disappeared by D$_2$O treatment), 6.95–7.45 (3H, m).

(Example 41)

N-cyano-N'-propargyl-N''-[2-<5-(2-dimethylaminomethylbenzimidazolyl)methylthio>ethyl]-guanidine (Intermediate product A).

Oily product,

IR (liq, cm$^{-1}$): 2160, 1670, 1610.

NMR (CDCl$_3$-CD$_3$OD, ppm): 2.35 (6H, s), 2.90–3.1 (2H, m), 3.3–3.5 (2H, m), 3.35 (2H, s), 3.80 (2H, s), 4.50 (2H, s), 5.78 (2H, s, disappeared by D$_2$O treatment), 7.0–7.7 (3H, m).

(Example 42)

1-nitro-2-methylamino-2-[2-<5-(2-dimethylaminomethylbenzimidazolyl)methylthio>ethylamino]ethylene (Intermediate product A).

Oily product,

IR (liq, cm$^{-1}$): 1560.

NMR (CDCl$_3$, ppm): 2.30 (6H, s), 2.65 (2H, t), 2.75 (2H, d), 3.7 (2H, s), 3.75 (2H, s), 6.40 (1H, s), 6.9–7.5 (3H, m), 8.1 (1H, b).

(Example 43)

1-nitro-2-methylamino-2-{3-[5-<2-(1-piperidinomethyl)benzimidazolyl>methylthio]propylamino}ethylene (Intermediate product E).

mp: 60°–62° C.,

IR (KBr, cm$^{-1}$): 3200, 1580.

NMR (DMSO-d$_6$, ppm): 1.3–1.7 (6H, m), 2.2–2.7 (4H, m), 2.64 (3H, d), 3.57 (2H, s), 3.80 (2H, s), 6.43 (1H, s), 6.8–7.4 (3H, m), 8.1 (1H, b).

(Example 44)

1-nitro-2-propargylamino-2-[2-<5-(2-dimethylaminomethylbenzimidazolyl)methylthio>ethylamino]ethylene (Intermediate product A).

Oily product.

IR (liq, cm$^{-1}$): 2120, 1610.

NMR (CDCl$_3$-CD$_3$OD, ppm): 2.3 (6H, s), 2.45 (1H, t), 2.60 (2H, t), 3.30 (2H, t), 3.70 (2H, s), 3.78 (2H, s), 3.90 (2H, s), 6.60 (2H, s), 7.0–7.6 (3H, m).

(Example 45)

1-nitro-2-dimethylamino-2-[2-<5-(2-dimethylaminomethylbenzimidazolyl)methylthio>ethylamino]ethylene (Intermediate product A).

Oily product.

IR (liq, cm$^{-1}$); 1670.

NMR (CDCl$_3$, ppm): 2.28 (6H, s), 2.50–2.70 (2H, m), 2.78 (2H, s), 3.1–3.3 (2H, m), 3.70 (2H, s), 3.78 (2H, s), 6.38 (1H, s), 6.40 (1H, b, disappeared by D$_2$O treatment), 6.9–7.6 (3H, m), 9.2 (1H, b, disappeared by D$_2$O treatment).

(Example 46)

N-benzenesulfonyl-N'-[2-<5-(2-dimethylaminomethylbenzimidazolyl)methylthio>ethyl]guanidine (Intermediate product A).

Oily product.

IR (liq. cm$^{-1}$): 3350, 1620, 1550.

NMR (CDCl$_3$-DMSO-d$_6$, ppm): 2.2 (6H, s), 2.3–2.6 (2H, m), 3.2–3.4 (2H, m), 3.65 (4H, s), 6.70 (2H, b, disappeared by D$_2$O treatment), 6.8–7.85 (8H, m), 8.3 (1H, b, disappeared by D$_2$O treatment).

(Example 47)

N-benzensulfonyl-N'-methyl-N''-[2-<5-(2-dimethylaminomethylbenzimidazolyl)methylthio>ethyl]guanidine (Intermediate product A).

Oily product.

IR (liq. cm$^{-1}$): 1580.

NMR (CDCl$_3$, ppm): 2.28 (6H, s), 2.3–2.6 (2H, m), 2.65 (3H, d), 3.2–3.4 (2H, m), 3.65 (4H, s), 6.0 (1H, b, disappeared by D$_2$O treatment), 6.9–7.8 (8H, m), 8.4 (2H, b, disappeared by D$_2$O treatment).

(Example 48)

N-benzenesulfonyl-N',N'-dimethyl-N''-[2-<5-(2-dimethylaminomethylbenzimidazolyl)methylthio>ethyl]guanidine (Intermediate product A).

Oily product.

IR (liq. cm$^{-1}$): 3350, 1590.

NMR (CDCl$_3$, ppm): 2.28 (6H, s), 2.25–2.5 (2H, m), 2.8 (6H, s), 3.15 (2H, q), 3.7 (4H, s), 6.50 (1H, b, disappeared by D$_2$O treatment), 6.9–7.9 (8H, m).

EXAMPLES 49–51

To an aqueous methanol (25 ml) solution of elhyl 4-chloro-3-nitrobenzoate (11.71 g) was added an aqueous 70% sodium hydrosulfide solution (8.6 g) and sulfur (0.8 g). 4,4'-dithiobis-(ethyl-3-nitrobenzoate) (9.55 g) was obtained by collecting the yellow precipitate. The bis compound was subjected to Bechamp reduction to obtain 4,4'-dithiobis(ethyl-3-aminobenzoate) (8.5 g). Then, the amino compound (4.6 g) was caused to react with chloroacetyl chloride (3.4 g) in benzene (25 ml) to yield 4,4'-dithiobis(ethyl-3-chloroacetoamidobenzoate) (5.8 g). Next, triphenyl phosphine (7.6 g) in dioxane (79 ml) was added to the chloroacetoamido compound (7.9 g). The mixture was stirred for 30 minutes at 40°–50° C. then subjected to cooling with iced water. The mixture was further subjected to stirring for 30 minutes with addition of an aqueous 50% dimethylamine solution (20 ml) to yield 5-ethoxycarbonyl-2-dimethylaminomethylbenzothiazole (5.6 g).

The benzothiazole derivative (1 g) was subjected to reduction with lithium aluminum hydride (0.6 g) in anhydrous tetrahydrofuran (15 ml). Then, the product was refluxed by heating for 6 hrs in an aqueous solution (7.2 ml) of cystheamine hydrochloride (0.43 g) and 47% hydrobromide to yield 5-[(2-aminoethyl)thiomethyl]-2-dimethylaminomethylbenzothiazole.2hydrobromide (1.52 g).

IR (KBr, cm$^{-1}$): 3470, 2550, 1443, 1060.

NMR (DMSO-d$_6$, ppm): 2.6–3.3 (4H, m), 3.04 (6H, s), 3.98 (2H, s), 5.06 (2H, s), 6.4–6.8 (4H, b, disappeared by D$_2$O treatment), 7.3–8.3 (3H, m).

The following two kinds of compounds were obtained in a similar manner:

5-[(2-aminoethyl)thiomethyl]-2-(1-piperidinomethyl)-benzothiazol.2hydrobramide

IR (KBr, cm$^{-1}$): 3450, 1604, 1440, 1065.

NMR (DMSO-d$_6$, ppm): 1.5–2.1 (6H, m), 2.7–3.7 (8H, m), 3.98 (2H, s), 4.92 (2H, s), 7.3–8.2 (3H, m), 7.7–8.5 (4H, b, disappeared by D$_2$O treatment).

5-[(2-aminoethyl)thiomethyl]-2-(4-morpholinomethyl)-benzothiazole.2hydrobromide

IR (KBr, cm$^{-1}$): 2850, 1604, 1460.

NMR (DMSO-d$_6$, ppm): 2.7–3.4 (4H, b), 2.7–3.7 (4H, m), 3.3–3.8 (4H, b), 3.96 (2H, s), 4.9 (2H, s), 7.3–8.2 (3H, m), 7.6–8.7 (4H, b, disappeared by D$_2$O treatment).

According to the method described in Example 32(B), the following compounds were obtained respectively by use of one kind of compound obtained above and the necessary reaction compounds.

N-cyano-N'-methyl-N''-[2-<5-(2-dimethylaminomethylbenzothiazolyl)methylthio>ethyl]guanidine IR (liq. cm$^{-1}$): 3300, 2150.

NMR (DMSO-d$_6$, ppm): 1.87 (6H, s), 2.5–3.0 (2H, m), 2.67 (3H, d), 3.1–3.6 (2H, m), 5.58 (1H, t, disappeared by D$_2$O treatment), 5.9 (1H, q, disappeared by D$_2$O treatment), 7.1–7.8 (3H, m).

N-cyano-N'-methyl-N''-{2-[5-<2-(1-piperidinomethyl)benzothiazolyl>methylthio]ethyl}quanidine IR (liq. cm$^{-1}$): 3470, 3250, 2180.

NMR (CDCl$_3$, ppm): 1.3–1.9 (6H, m), 2.2–3.0 (2H, m), 2.3–2.8 (4H, m), 2.76 (3H, d), 3.1–3.6 (2H, q), 3.82 (4H, s), 5.6–6.2 (2H, b, disappeared by D$_2$O treatment), 7.1–7.8 (3H, m).

N-cyano-N'-methyl-N''-{2-[5-<2-(4-morpholinomethyl)benzothiazolyl>methylthio]ethyl}guanidine mp: 135°–137° C.

IR (KBr, cm$^{-1}$): 3450, 2180.

NMR (CD$_3$OD, ppm): 2.4–3.0 (6H, m), 2.78 (3H, s), 3.38 (2H, t), 3.6–4.0 (4H, m), 3.83 (2H, s), 3.90 (2H, s), 7.2–7.9 (3H, m).

EXAMPLE 52

6-ethoxycarbonyl-2-methylbenzothiazole (2.09 g) prepared according to the method described in J. Gen. Chem. vol. 5, pp. 260–266 (1945) was subjected to bromination with NBS (1.78 g) in carbon tetrachloride (30 mg). Then, the product was caused to react with dimethylamine to yield a new compound of 6-ethoxycarbonyl-2-dimethylaminomethylbenzothiazole (0.8 g). Then, the compound was provided with the same treatment as that described in Examples 49–51 to yield 6-[(2-aminoethyl)thiomethyl]-2-(dimethylaminomethyl)benzothiazole.2hydrobromide (1.2 g).

IR (KBr, cm$^{-1}$): 1595, 1400.

NMR (DMSO-d$_6$, ppm): 2.4–3.2 (4H, m), 3.0 (6H, s), 3.94 (2H, s), 5.02 (2H-s), 7.3–8.2 (3H, m), 7.6–8.4 (4H, b, disappeared by D$_2$O treatment).

According to the method described in Example 32(B), N-cyano-N'-methyl-N''-[2-<6-(2-dimethylaminomethylbenzothiazolyl)methylthio>ethyl]guanidine was obtained using the compound obtained above and the necessary reaction reagents.

mp: 116°–118° C.

IR (KBr, cm$^{-1}$): 2170.

NMR (CDCl$_3$, ppm): 2.2–2.8 (2H, m), 2.31 (6H, s), 2.69 (3H, d), 3.0–3.6 (2H, m), 3.80 (2H, s), 3.81 (2H, s), 7.2–7.9 (3H, m), 6.6–7.1 (2H, b, disappeared by D$_2$O treatment).

EXAMPLE 53

4-chloro-3-nitrobenzoic acid was subjected to borane reduction to yield 4-chloro-3-nitrobenzyl alcohol. The benzyl alcohol compound was treated with sodium sulfide, and 4,4'-dithiobis(3-aminobenzyl alcohol) thus obtained was caused to react with triphenylphosphine in dioxane, and further with 1-cyanoguanidine to yield 5-hydroxymethyl-2-guanidinobenzothiazole. Then, the hydroxymethyl compound (0.5 g) was refluxed with heating for 15 minutes in an aqueous 47% hydrobromic acid solution (5 ml) to yield 5-bromomethyl-2-guanidinobenzothiazole.hydrobromide (0.63 g).

Cysteamine.hydrochloride (0.4 g) was caused to react with sodium ethoxide in ethanol to yield a sodium salt. Then, 5-bromomethyl-2-guanidinobenzothiazole.hydrobromide (0.63 g) was added to the sodium salt at an internal temperature of 0° C. After agitating the mixture over one night at room temperature, the solvent was removed, and the residue was made acidic with addition of dilute hydrochloric acid. The crystalline precipitate was collected to obtain 5-[(2-aminoethyl)thiomethyl]-2-guanidinobenzothiazole.2hydrochloride (0.5 g).

NMR (DMSO-d$_6$, ppm): 2.58–3.0 (4H, m), 3.87 (2H, s), 7.1–8.0. (3H, m), 8.0–8.3 (2H, b, disappeared by D$_2$O treatment), 8.45 (4H, b, disappeared by D$_2$O treatment).

According to the method described in Example 32(B), N-cyano-N'-methyl-N''-[2-<5-(2-guanidinobenzothiazolyl)methylthio>ethyl]guanidine was obtained using the necessary reaction reagents.

mp: 68°–71° C.

IR (KBr, cm$^{-1}$): 2160.

NMR (CD$_3$OD, ppm): 2.4–3.0 (2H, m), 2.74 (3H, s), 3.1–3.6 (2H, m), 3.73 (2H, s), 6.9–7.8 (3H, m).

EXAMPLES 54–56

Ethyl 4-hydroxy-3-nitrobenzoate (32 g) prepared according to the method described in J. Org. Chem., vol. 26, p. 2223 (1961) was subjected to reduction under increased pressure at 70 atm in the presence of a Raney Nickel catalyst in absolute ethanol (200 ml). The product was then caused to react with chloroacetyl chloride, and was subsequently subjected to ring closure with phosphorous oxychloride to yield 2-chloromethyl-5-ethoxycarbonylbenzoxazole (27.3 g). The chloromethyl compound (10 g) was caused to react with dimethylamine to yield 2-dimethylaminomethyl-5-ethoxycarbonylbenzoxazole (6 g), which was subsequently subjected to reduction with lithium aluminium hydride in anhydrous tetrahydrofuran (60 ml) thereby to obtain 2-dimethylaminomethyl-5-hydroxymethylbenzoxazole (2 g).

The hydroxymethyl compound (1.7 g) was agitated in anhydrous chloroform (30 mg) for two hrs at room temperature with addition of thionyl chloride (0.9 g) to yield 5-chloromethyl-2-dimethylaminomethylbenzoxazole (1.8 g).

Cysteamine.hydrochloride (0.93 g) was caused to react with sodium ethoxide in ethanol to yield a sodium salt, which was then caused to react with 5-chloromethyl-2-dimethylaminomethylbenzoxazole (1.8 g) to yield 5-[(2-aminoethyl)thiomethyl]-2-dimethylaminomethylbenzoxazole (1.9 g).

In a similar manner, 5-[(2-aminoethyl)thiomethyl]-2-(1-piperidinolmethyl)benzoxazole and 5-[(2-aminoethyl)thiomethyl]-2-(4-morpholinomethyl)benzoxazole were also obtained.

According to the method described in Example 32(B), the following compounds were obtained by use of one kind of compound obtained above and the necessary reaction reagents:

N-cyano-N'-methyl-N''-[2-<5-(2-dimethylaminomethylbenzoxazolyl)methylthio>ethyl]guanidine mp: 139.3° C.

IR (KBr, cm$^{-1}$): 3330, 2950, 2150, 1580.

NMR (CDCl$_3$, ppm): 2.5 (6H, s), 2.5–3.1 (5H, m), 3.25–3.7 (2H, d), 3.8–4.0 (4H, d), 7.25–7.7 (3H, m).

N-cyano-N'-methyl-N''-{2-[5-<2-(1-piperidinomethyl)benzoxazolyl>methylthio]ethyl}guanidine mp: 37°–42° C.

IR (KBr, cm$^{-1}$): 3300, 2950, 2170, 1580.

NMR (CDCl$_3$, ppm): 1.3–2.7 (12H, m), 2.5–2.9 (3H, d), 3.1–3.6 (2H, m), 3.75 (2H, s), 5.3–5.9 (2H, m), 7.05–7.6 (3H, m).

N-cyano-N'-methyl-N''-{2-[5-<2-(4-morpholinomethyl)benzoxazolyl>methylthio]ethyl}guanidine IR (KBr, cm$^{-1}$): 3280, 2940, 2880, 2160, 1580.

NMR (CDCl$_3$, ppm): 2.4–2.95 (10H, m), 3.5–3.95 (9H, m), 5.8–6.4 (2H, b), 7.1–(3H, m).

EXAMPLE 57

4-hydroxy-3-nitrobenzyl alcohol (13 g) prepared in a method similar to that described in U.S. Pat. No. 2,717,196 (1955) as well as an aqueous 47% hydrobromide solution (100 ml) of cysteamine.hydrochloride (10.5 g) were refluxed by heating for 3 hrs to yield 3-(2-aminoethylthiomethyl)-2-nitrophenol.hydrobromide (9 g). The phenol derivative (9 g) in benzene (50 ml) was refluxed by heating for 4 hrs with triethylamine (2.8 g) and phthalic anhydride (3.8 g) to obtain N-[2-(4-hydroxy-3-nitrophenylmethylthio)ethyl]phthalimide (9.56 g). After the phthalimide compound (3.6 g) was reduced under increased pressure at 70 atm in tetrahydrofuran (50 ml) in the presence of a 5% palladium carbon catalyst, the product was caused to react with cyanogen bromide to yield 2-amino-5-[2-<2-(1,3(2H)- dioxo-1H-isoindolyl>ethylthiomethyl]benzoxazole (2.9 g).

IR (KBr, cm$^{-1}$): 3450, 1775, 1720, 1680.

NMR (CDCl$_3$, ppm): 2.55-2.85 (2H, t), 3.6-4.0 (4H, m), 4.3 (2H, s), 6.9-7.2 (3H, m), 7.5-7.9 (4H, m).

The benzoxazole derivative was heated with hydrazine hydrate to yield 2-amino-5-[(2-aminoethyl)thiomethyl]benzoxazole.

According to the method described in Example 32(B), N-cyano-N'-methyl-N''-[2-5-(2-aminobenzoxazolyl)methylthioethyl]guanidine was obtained using the above product as it was without purifying it and using the necessary reaction reagents.

mp: 156.2° C.

IR (KBr, cm$^{-1}$): 3300, 2950, 2150, 1670, 1580.

NMR (DMSO-d$_6$, ppm): 2.4-2.6 (2H, m), 2.65 (3H, d), 3.1-3.4 (2H, m), 3.75 (2H, s), 6.7-7.3 (7H, m, 4H disappeared by D$_2$O treatment).

EXAMPLE 58

5-(3-aminopropoxy)-2-dimethylaminomethylbenzimidazole (0.5 g) prepared in Example 1(A) as well as 2-methylthio-4-pyrimidone (0.29 g) were heated on an oil bath at 150° C. for 1 hr. The oily product obtained was subjected to column chromatography using a silica gel/ethyl acetate:methanol (9:1) thereby to obtain 2-[3-<5-(2-dimethylaminomethylbenzimidazolyl)oxy>-propylamino]-4-pyrimidone (melting point 84.6° C., 0.484 g, 70%).

IR (KBr, cm$^{-1}$): 3200-3000, 2950, 1680, 1620.

NMR (DMSO-d$_6$, ppm): 1.78-2.0 (2H, m), 2.12 (6H, s), 3.27-3.58 (2H, m), 3.6 (2H, s), 3.88-4.13 (2H, m), 5.48 (1H, d), 6.41-7.62 (7H, m, 3H disappeared by D$_2$O treatment).

EXAMPLES 59-78

According to the method described in Example 58, the following compounds were obtained using various intermediate products prepared in the above-described examples as well as the necessary reaction reagents. Figures in brackets following the name of each compound indicates the number of the Example in which the starting material was prepared.

(Example 59)

2-[3-<5-(2-(1-piperidinomethyl)benzimidazolyl)oxy>-propylamino]-4-pyrimidone [5(A)]

mp: 134.7° C.

IR(KBr, cm$^{-1}$): 3200-3000, 2950, 1680, 1620.

NMR (DMSO-d$_6$, ppm): 1.36-1.68 (6H, m), 1.82-2.1 (2H, m), 2.26-2.65 (4H, m), 3.2-4.2 (6H, m), 5.45 (1H, d), 6.4-7.6 (7H, m, 3H disappeared by D$_2$O treatment).

(Example 60)

5-dimethylaminomethyl-[3-<5-(2-dimethylaminomethylbenzimidazolyl)oxy>propylamino]-4-pyrimidone [1(A)]

mp: 108.9° C.

IR (KBr, cm$^{-1}$): 3250, 2950, 1660, 1610.

NMR (DMSO-d$_6$, ppm): 1.8-2.1 (2H, m), 2.15 (6H, s), 2.25 (6H, s), 3.13 (2H, s), 3.3-3.55 (2H, m), 3.6 (2H, s), 3.85-4.1 (2H, m), 5.4-6.0 (3H, b, disappeared by D$_2$O treatment), 6.55-7.4 (4H, m).

(Example 61)

5-dimethylaminomethyl-2-[3-<5-(2-(1-piperidinomethyl)benzimidazolyl)oxy>propylamino]-4-pyrimidone [5(A)]

mp: 51.5° C.

IR (KBr, cm$^{-1}$): 3200, 2950, 1660, 1610.

NMR (CDCl$_3$, ppm): 1.38-1.70 (6H, m), 2.3 (6H, s), 2.4-2.65 (6H, m), 3.25-3.6 (4H, m), 3.65 (2H, s), 3.75-4.0 (2H, m), 6.4-7.4 (4H, m), 8.35-8.9 (3H, b, disappeared by D$_2$O treatment).

(Example 62)

5-[5-(1,3-benzodioxolyl)methyl]-2-[3-<5-(2-dimethylaminomethylbenzimidazolyl)oxy>propylamino]-4-pyrimidone [1(A)]

mp: 143.8° C.

IR (KBr, cm$^{-1}$): 3200, 3100, 1660, 1610.

NMR (DMSO-d$_6$, ppm): 1.85-2.15 (2H, m), 2.28 (6H, s), 3.2-3.4 (2H, m), 3.4 (2H, s), 3.65 (2H, s), 3.8-4.10 (2H, m), 5.2-5.6 (2H, b, disappeared by D$_2$O treatment), 5.72 (2H, s), 6.5-7.35 (8H, m, 1H disappeared by D$_2$O treatment).

(Example 63)

5-[5-(1,3-benzodioxolyl)methyl]-2-[3-<5-(2-(1-pyrrolidinomethyl)benzimidazolyl)oxy>propylamino]-4-pyrimidone [3(A)]

mp: 85° C.

IR (KBr, cm$^{-1}$): 3250, 2950, 1660, 1610.

NMR (DMSO-d$_6$, ppm): 1.63-1.88 (4H, m), 1.9-2.1 (2H, m), 2.35-2.65 (4H, m), 3.3-3.5 (4H, m), 3.69 (2H, s), 3.78-4.03 (2H, m), 5.72 (2H, s), 6.05-6.35 (1H, b, disappeared by D$_2$O treatment), 6.5-7.22 (8H, m, 1H disappeared by D$_2$O treatment).

(Example 64)

5-[5-(1,3-benzodioxolyl)methyl]-2-[3-<5-(2-(1-piperidinomethyl)benzimidazolyl)oxy>propylamino]-4-pyrimidone [5(A)]

mp: 126° C.

IR (KBr, cm$^{-1}$): 3250, 2950, 1660, 1610.

NMR (DMSO-d$_6$, ppm): 1.25-1.65 (6H, m), 1.8-2.05 (2H, m), 2.2-2.6 (4H, m), 3.3-3.5 (2H, m), 3.4 (2H, s), 3.6 (2H, s), 3.76-4.16 (2H, m), 5.83 (2H, s), 6.5-7.4 (9H, m, 2H disappeared by D$_2$O treatment).

(Example 65)

5-[5-(1,3-benzodioxolyl)methyl]-2-[3-<5-(2-guanidonobenzimidazolyl)oxy>propylamino]-4-pyrimidone [8(A)]

mp: 163.8° C.

IR (KBr, cm$^{-1}$): 3300-3000, 1650.

NMR (DMSO-d$_6$, ppm): 1.85-2.2 (2H, m), 2.9-3.1 (2H, m), 3.5 (2H, s), 3.9-4.1 (2H, m), 5.85 (2H, s), 6.1-7.6 (14H, m, 7H disappeared by D$_2$O treatment).

(Example 66)

2-[3-<5-(2-dimethylaminomethylbenzimidazolyl)oxy>propylamino]-5-(3-pyridylmethyl)-4-pyrimidone [1(A)]

Melting point: 149.9° C.

IR (KBr, cm$^{-1}$): 3200, 3100, 1660, 1610.

NMR (MeOH-d₄, ppm): 1.95–2.15 (2H, m), 2.35 (6H, s), 3.5–3.75 (2H, m), 3.76 (2H, s), 3.72 (2H, s) 3.9–4.1 (2H, m).

(Example 67)

2-{3-[5-<2-(1-pyrrolidinomethyl)benzimidazolyl>oxy]propylamino}-5-(3-pyridylmethyl)-4-pyrimidone [3(A)]

Melting point: 118° C.
IR (KBr, cm⁻¹): 3250, 3050, 2950, 1670, 1610.
NMR (DMSO-d₆, ppm): 1.5–1.85 (4H, m), 1.85–2.15 (2H, m), 2.4–2.75 (4H, m), 3.3–3.65 (4H, m), 3.75 (2H, s), 3.8–4.1 (2H, m), 6.3–6.5 (1H, b, disappeared by D₂O treatment), 6.55–8.4 (9H, m, aromatic).

(Example 68)

2-{3-[5-<2-(1-piperidinomethyl)benzimidazolyl>oxy]propylamino}-5-(3-pyridylmethyl)-4-pyrimidone [5(A)]

Melting point: 78.8° C.
IR (KBr, cm⁻¹): 3050, 2950, 1670, 1610.
NMR (DMSO-d₆, ppm): 1.3–1.6 (6H, m), 1.9–2.1 (2H, m), 2.25–2.55 (4H, m), 3.2–3.5 (4H, m), 3.6 (2H, s), 3.8–4.1 (2H, m), 6.3–6.5 (1H, b, disappeared by D₂O treatment), 6.55–8.4 (8H, m, aromatic+1H, disappeared by D₂O treatment).

(Example 69)

2-[3-<5-(2-guanidinobenzimidazolyl)oxy>propylamino]-5-(3-pyridylmethyl)-4-pyrimidone [8(A)]

Melting point: 179.1° C.
IR (KBr, cm⁻¹): 3250–3000, 1660.
NMR (DMSO-d₆, ppm): 1.95–2.15 (2H, m), 2.9–3.1 (2H, m), 3.62 (2H, s), 3.9–4.1 (2H, m), 5.3–5.7 (6H, b, disappeared by D₂O treatment).

(Example 70)

2-[3-<5-(2-dimethylaminomethylbenzimidazolyl)oxy>propylamino]-5-(3-dimethylaminomethylbenzyl)-4-pyrimidone [1(A)]

Melting point: 103.6° C.
IR (KBr, cm⁻¹): 3100, 2950, 1660, 1610.
NMR (DMSO-d₆, ppm): 1.8–2.08 (2H, m), 2.1 (6H, s), 2.2 (6H, s), 3.2–3.65 (8H, m), 3.8–4.1 (2H, m), 6.4–7.4 (8H, m, aromatic+2H, disappeared by D₂O treatment).

(Example 71)

2-{3-[5-<2-(1-piperidinomethyl)benzimidazolyl>oxy]propylamino}5-(3-dimethylaminomethylbenzyl)-4-pyrimidone [5(A)]

Melting point: 40.8° C.
IR (KBr, cm⁻¹): 3050, 2950, 1670, 1610.
NMR (DMSO-d₆, ppm): 1.3–1.6 (6H, m), 1.8–2.0 (2H, m), 2.07 (6H, s), 2.2–2.4 (4H, m), 3.2–4.2 (10H, m), 6.3–7.4 (10H, m).

(Example 72)

2-[2-<5-(2-dimethyaminomethylbenzimidazolyl)methylthio>ethylamino]-4-pyrimidone [Examples 34–48, Intermediate product A]

Melting point: 60° C.
IR (KBr, cm⁻¹): 3200, 3050, 2950, 1660, 1600.
NMR (DMSO-d₆, ppm): 2.34 (6H, s), 2.45–2.78 (2H, m), 3.22–3.58 (2H, m), 3.67 (2H, s), 3.8 (2H, s), 5.54 (2H, d), 5.9–6.9 (3H, b, disappeared by D₂O treatment), 6.9–7.8 (4H, m, aromatic).

(Example 73)

2-[2-<5-(2-dimethylaminomethylbenzimidazolyl)methylthio>ethylamino]-5-dimethylaminomethyl-4-pyrimidone [Examples 34–48, Intermediate product A]

Melting point: 61.9° C.
IR (KBr, cm⁻¹): 3200, 2950, 1660, 1600.
NMR (CDCl₃, ppm): 2.25 (6H, s), 2.3 (6H, s), 2.5–2.8 (2H, m), 3.1–3.4 (2H, m), 3.4–3.8 (6H, m), 6.85–7.63 (4H, m, aromatic), 7.63–8.1 (3H, b, disappeared by D₂O treatment).

(Example 74)

2-[2-<5-(2-dimethylaminomethylbenziimidazolyl)methylthio>ethylamino]-5-[5-(1,3-benzodioxolyl)methyl]-4-pyrimidone [Examples 34–48, Intermediate product A]

Melting point: 107.8° C.
IR (KBr, cm⁻¹): 3100, 2930, 1660, 1610.
NMR (DMSO-d₆, ppm): 2.31 (6H, s), 2.35–2.6 (2H, m), 3.2–3.5 (2H, m), 3.40 (2H, s), 3.78 (2H, s), 3.80 (2H, s), 5.85 (2H, s), 6.35–6.6 (1H, b, disappeared by D₂O treatment).

(Example 75)

2-{2-[5-<2-(1-piperidinomethyl)benzimidazolyl>methylthio]ethylamino}-5-[5-(1,3-benzodioxolyl)methyl]-4-pyrimidone [Examples 34–48, Intermediate product B]

Melting point: 123.5° C.
IR (KBr, cm⁻¹): 3250, 3100, 2950, 1660, 1610.
NMR (DMSO-d₆, ppm): 1.35–1.65 (6H, m), 2.35–2.6 (6H, m), 3.15–3.45 (2H, m), 3.41 (2H, s), 3.63 (2H, s), 3.78 (2H, s), 5.80 (2H, s), 6.2–6.4 (1H, b, disappeared by D₂O treatment), 6.56–7.35 (7H, m, aromatic+2H, disappeared by D₂O treatment).

(Example 76)

2-[2-<5-(2-dimethylaminomethylbenzimidazolyl)methylthio>ethylamino]-5-(3-pyridylmethyl)-4-pyrimidone [Examples 34–48, Intermediate product A]

Melting point: 104.8° C.
IR (KBr, cm⁻¹): 3200, 3050, 1660, 1600.
NMR (DMSO-d₆, ppm): 2.24 (6H, s), 2.42–2.67 (2H, m), 3.25–3.5 (2H, m), 3.5 (2H, s), 3.82 (2H, s), 6.35–6.55 (1H, b, disappeared by D₂O treatment), 6.9–7.45 (6H, m, aromatic+1H dissappered by D₂O treatment), 8.5–8.38 (2H, m, aromatic).

(Example 77)

2-{2-[5-<2-(1-piperidinomethyl)benzimidazolyl>methylthio]ethylamino}-5-(3-pyridylmethyl)-4-pyrimidone [Examples 34–48, Intermediate product B]

IR (KBr, cm⁻¹): 3200, 2950, 1670, 1605.
NMR (CDCl₃, ppm): 1.3–1.6 (6H, m), 2.3–2.55 (6H, m), 3.3–3.55 (2H, m), 3.6 (2H, s), 3.67 (2H, s), 3.73 (2H, s), 6.3–6.6 (2H, b, disappeared by D₂O treatment), 6.9–7.43 (8H, m, aromatic).

(Example 78)

2-[2-<5-(2-dimethylaminomethylbenzimidazolyl)methylthio>ethylamino]-5-(3-dimethylaminomethylbenzyl)-4-pyrimidone [Examples 34–48, Intermediate product A]

IR (KBr, cm⁻¹): 3200–3000, 1660, 1610.

NMR (MeOH-d$_4$, ppm): 2.2 (6H, s), 2.25 (6H, s), 2.4–2.75 (2H, m), 3.2–3.78 (10H, m), 6.9–7.5 (8H, m, aromatic).

(Example 79)

2-[5-(2-dimethylaminomethylbenzimidazolyl)oxy]ethylamine (0.60 g) prepared according to the method described in Example 1(A) using the necessary reaction reagents as well as 3-methylthio-6-(3-methoxybenzyl)-1,2,4-triazine-5-one (0.68 g) were heated on a oil bath for 1 hour at 160°–170° C.

An extraction by heating was conducted with addition of methanol to the reacted mixture, and the crystal obtained was subjected to recrystallization from DMF thereby to obtain a colorless crystal of 3-[2-<5-(2-dimethylaminomethylbenzimidazolyl)oxy>ethylamino]-6-(3-methoxybenzyl)1,2,4-triazine-5-one (0.3 g, 25.8%).

Melting point: 222°–225° C.
IR (KBr, cm$^{-1}$): 3240, 1640, 1575.
NMR (DMSO-d$_6$+CDCL$_3$, ppm): 2.62 (6H, s), 3.43–4.20 (11H, m), 6.23–7.37 (8H, m, aromatic).

EXAMPLES 80–87

According to the method described in Example 79, the following compounds were obtained using various intermediate products prepared in various examples described above as well as the necessary reaction reagents. Figures in brackets following the name of each compound indicate the number of the Examples in which the starting material was prepared.

(Example 80)

3-{3-[5-<2-(1-pyrrolidinomethyl)benzimidazolyl>oxy]propylamino}-6-(3-methoxybenzyl)-1,2,4-triazine-5-one [3(A)]

Melting point: 202°–207° C.
IR (KBr, cm$^{-1}$): 3250, 1635, 1575.
NMR (DMSO-d$_6$, ppm): 1.35–2.15 (6H, m), 2.15–2.73 (4H, m), 3.05–4.23 (11H, m), 6.25–7.44 (8H, m, aromatic).

(Example 81)

3-{3-[5-<2-(1-piperidinomethyl)benzimidazolyl>oxy]propylamino}-6-(3-methoxy-benzyl)-1,2,4-triazine-5-one [5(A)]

Melting point: 216°–223° C.
IR (KBr, cm$^{-1}$): 3260, 2950, 1630, 1575.
NMR (DMSO-d$_6$, ppm): 1.23–1.70 (6H, m), 1.70–2.13 (2H, m), 2.13–2.60 (4H, m), 3.00–4.25 (11H, m), 6.40–7.40 (8H, m, aromatic).

(Example 82)

3-[2-<5-(2-dimethylaminomethylbenzimidazolyl)oxy>ethylamino]-6-(3-pyridylmethyl)-1,2,4-triazine-5-one [1(A)]

Melting point: 223°–226° C.
IR (KBr, cm$^{-1}$): 3230, 1630, 1575.
NMR (DMSO-d$_6$, ppm): 2.23 (6H, s), 3.33–4.30(4H, m), 3.58 (2H, s), 3.78 (2H, s), 6.45–7.72 (6H, m), 8.13–8.50 (2H, m).

(Example 83)

3-[3-<5-(2-dimethylaminomethylbenzimidazolyl)oxy>propylamino]-6-(3-pyridylmethyl)-1,2,4-triazine-5-one [1(A)]

Melting point: 218°–224° C.
IR (KBr, cm$^{-1}$): 3070, 2940, 1655, 1580.
NMR (DMSO-d$_6$, ppm): 1.70–2.40 (8H, m), 3.03–4.20 (8H, m), 6.44–7.70 (6H, m), 8.04–8.50 (2H, m, aromatic).

(Example 84)

3-{3-[5-<]-(1-pyrrolidinomethyl)benzimidazolyl>oxy]propylamino}-6-(3-pyridylmethyl)-1,2,4-triazine-5-one [3(A)]

Melting point: 219°–225° C.
IR (KBr, cm$^{-1}$): 3260, 1635, 1575.
NMR (DMSO-d$_6$, ppm): 1.45–2.20 (6H, m), 2.25–2.75 (4H, m), 3.05–4.23 (11H, m), 6.25–7.44 (8H, m, aromatic).

(Example 85)

3-{3-[5-<2-(1-piperidinomethyl)benzimidazolyl>oxy]propylamino}-6-(3-pyridylmethyl)-1,2,4-triazine-5-one [5(A)]

Melting point: 217°–223° C.
IR (KBr, cm$^{-1}$): 3260, 2950, 1630, 1570.
NMR (DMSO-d$_6$, ppm): 1.23–1.67 (6H, m), 1.73–2.18 (2H, m), 2.20–2.64 (4H, m), 3.00–3.56 (2H, m), 3.56 (2H, s), 3.74 (2H, s), 3.94 (2H, t), 6.50–7.70 (6H, m, aromatic), 8.15–8.51 (2H, m, aromatic).

(Example 86)

3-[2-<5-(2-dimethylaminomethylbenzimidazolyl)methylthio>ethylamino]-6-(3-methoxybenzyl)-1,2,4-triazine-5-one [Intermediate product A of Examples 34–48]

Melting point: 212°–220° C.
IR (KBr, cm$^{-1}$): 3250, 1645, 1575.
NMR (DMSO-d$_6$, ppm): 2.60 (6H, s), 3.57 (2H, s), 3.65 (3H, s), 3.69 (2H, s), 3.79 (2H, s), 6.50–7.47 (8H, m, aromatic)

(Example 87)

3-[2-<5-(2-dimethylaminomethylbenzimidazolyl)methylthio>ethylamino]-6-(3-pyridylmethyl)-1,2,4-triazine-5-one [Intermediate product A of Examples 34–38]

Melting point: 224°–232° C.
IR (KBr, cm$^{-1}$): 3250 1650, 1600, 1570.
NMR (DMSO-d$_6$, ppm): 2.18 (6H, s), 3.56 (2H, s), 3.74 (2H, s), 3.77 (2H, s), 6.82–7.67 (6H, m, aromatic), 8.18–8.47 (2H, m, aromatic).

EXAMPLE 88

To a methanol (20 ml) solution of 5-[(3-aminopropyl)oxy]-2-dimethylaminomethylbenzimidazole (1.0 g) prepared in Example 1(A), was added (CH$_3$S)$_2$C=N—CN (0.61 g). After agitating the mixture for 20 hrs at room temperature, the solvent was removed under reduced pressure. The residue was subjected to column chromatography using a silica gel-/ethyl acetate:methanol (4:1), and N-cyano-N'-3-[5-(2-dimethylaminomethylbenzimidazolyl)oxy]propylcarbazimidothio-acid-methyl-ester (0.9 g) was obtained as a light yellow, oily product. To an ethanol (10 mg) solution of this intermediate crystal. (0.4 g) was added 100% hydrazine hydrate (0.4 g). After agitating the mixture for 22 hrs at room temperature, the solvent was removed under reduced pressure. The residue was subjected to column chromatography using a silica gel-/ethyl acetate:methanol (4:1), and 5-N-[3-<5-(2-dimethylaminomethylbenzimidazolyl)oxy>propyl]-1H-1,2,4-triazole-3,5-diamine (0.2 g, 34% yield) was obtained.

Melting point: 89°–92° C.
IR (KBr, cm$^{-1}$): 3250, 1620, 1550.
NMR (DMSO-d$_6$+CDCl$_3$, ppm): 2.25 (6H, s), 3.4–4.0 (8H, m), 6.8–7.4 (3H, m).

EXAMPLES 89–100

According to the method described in Example 88, the following compounds were obtained using the various intermediate products prepared in the aforementioned examples as well as the necessary reaction reagents. Figures in brackets following the name of each compound indicate the number of example in which an intermediate product of the starting material was prepared.

(Example 89)

5-{3-[5-<2-(1-pyrrolidinomethyl)benzimidazolyl>oxy]-propyl}-1H-1,2,4-triazole-3,5-diamine Melting point: 102°–106° C.
IR (KBr, cm$^{-1}$): 3200, 1630, 1570, 1160.
NMR (DMSO-d$_6$+CDCl$_3$, ppm): 1.5–2.6 (8H, m), 3.3 (2H, s), 6.6–7.5 (3H, m, aromatic).

(Example 90)

5-{3-[5-<2-(1-piperidinomethyl)benzimidazolyl>oxy]-propyl-1H-}1,2,4-triazole-3,5-diamine [5(A)]

Melting point: 125°–127° C.
IR (KBr, cm$^{-1}$): 3350, 3200, 3100, 1640, 1575.
NMR (DMSO-d$_6$+CDCl$_3$, ppm): 0.9–1.8 (6H, b), 2.1–2.5 (4H, b), 2.9–4.1 (8H, m), 1.7–2.3 (3H, b), 6.4–7.4 (3H, m, aromatic).

(Example 91)

1-methyl-5-[3-<5-(2-dimethylaminomethylbenzimidazolyl)oxy>propyl]-1H-1,2,4-triazole-3,5-diamine [1(A)]

Melting point: 49°–53° C.
IR (KBr, cm$^{-1}$): 3250, 1620, 1555, 1160.
NMR (DMSO-d$_6$+CDCl$_3$, ppm): 2.3 (6H, s), 3.3 (3H, s), 3.35–4.2 (8H, m), 1.8–2.6 (4H, m), 6.5–7.5 (3H, m, aromatic).

(Example 92)

1-methyl-5-[4-<5-(2-dimethylaminomethylbenzimidazolyl)oxy>butyl]-1H-1,2,4-triazole-3,5-diamine [2(A)]

Melting point: 85°–87° C.
IR (KBr, cm$^{-1}$): 3250, 1620, 1560.
NMR (DMSO-d$_6$+CDCl$_3$, ppm): 2.2 (6H, s), 1.45–1.95 (4H, b), 3.25 (3H, s), 3.45–4.05 (6H, m), 6.5–7.35 (3H, m, aromatic).

(Example 93)

1-methyl-5-{3-[5-<2-(1-pyrrolidinomethyl)benzimidazolyl>oxy]propyl}-1H-1,2,4-triazole-3,5-diamine [3(A)]

Melting point: 115°–118° C.
IR (KBr, cm$^{-1}$): 3250, 1615, 1550, 1165.
NMR (DMSO-d$_6$+CDCl$_3$, ppm): 1.4–2.7 (8H, m), 3.2 (3H, s), 3.5–4.2 (8H, m), 6.5–7.5 (3H, m, aromatic).

(Example 94)

1-methyl-5-{3-[5-<2-(1-piperidinomethyl)benzimidazolyl>oxy]propyl}-1H-1,2,4-triazole-3,5-diamine [5(A)]

Melting point: 56°–59° C.
IR (KBr, cm$^{-1}$): 3200, 1605, 1550, 1160.
NMR (DMSO-d$_6$+CDCl$_3$, ppm): 1.25–1.7 (6H, b), 1.7–2.2 (3H, m), 2.15–2.7 (4H, b), 3.3 (3H, s), 3.4–4.2 (8H, m), 6.4–7.4 (3H, m, aromatic).

(Example 95)

1-methyl-5-[3-<5-(2-guanidinobenzimidazolyl)oxy>-propyl]-1H-1,2,4-triazole-3,5-diamine [8(A)]

Melting point: 135°–138° C.
IR (KBr, cm$^{-1}$): 3350, 3200, 1615, 1555, 1165.
NMR (DMSO-d$_6$+CDCl$_3$, ppm): 1.95–2.05 (4H, m), 3.25 (3H, s), 3.6–4.3 (4H, m), 6.3–7.2 (3H, m, aromatic).

(Example 96)

5-[2-<5-(2-dimethylaminomethylbenzimidazolyl)methylthio>ethyl]-1H-1,2,4-triazole-3,5-diamine [Intermediate product A of 34–48]

Melting point: 78°–83° C.
IR (KBr, cm$^{-1}$): 3200–3100, 2950, 1600, 1570.
NMR (CDCl$_3$+DC$_3$OD, ppm): 1.8–2.15 (2H, m), 2.35 (6H, s), 2.4–2.8 (2H, m), 3.05–3.5 (3H, m), 3.7–3.8 (4H, b), 7.0–7.5 (3H, m, aromatic).

(Example 97)

1-methyl-5-[2-<5-(2-dimethylaminomethylbenzimidazolyl)-methylthio>ethyl]-1H-1,2,4-triazole-3,5-diamine [Intermediate product A of 34–48]

Melting point: 87°–91° C.
IR (KBr, cm$^{-1}$): 3200, 1605, 1550.
NMR (DMSO-d$_6$+CDCl$_3$, ppm): 2.3 (6H, s), 2.4–2.8 (2H, m), 3.3 (3H, s), 3.35 (2H, s), 3.67 (2H, s), 3.8 (2H, s), 6.9–7.5 (8H, m).

(Example 98)

1-methyl-3-ethyl amino-5-[2-<5-(2-dimethylaminomethylbenzimidazolyl)methylthio>ethyl]-1H-1,2,4-triazole-5-amine [Intermediate product A of 34–48]

Melting point: 83°–86° C.
IR (KBr, cm$^{-1}$): 3250, 2950, 1620, 1550.
NMR (CDCl$_3$+CD$_3$OD, ppm): 1.17 (3H, t), 2.3 (6H, s), 2.4–3.6 (12H, m), 3.7 (2H, s), 3.8 (2H, s), 7.0–3H, m)

(Example 99)

1-methyl-3-dimethylamino-5-[2-<5-(2-dimethylaminomethylbenzimidazolyl)methylthio>ethyl]-1H-1,2,4-triazole-5-amine [Intermediate product A of Examples 34–48]

Melting point: 45°–48° C.
IR(KBr, cm$^{-1}$): 3200, 2950, 1620, 1560.
NMR (CDCl$_3$, ppm): 2.3(6H, s), 2.4–2.9 (2H, m), 2.9 (6H, s), 3.3 (3H, s), 3.6–4.0 (6H, m), 6.9–7.5 (3H, m, aromatic)

(Example 100)

1-methyl-3-pyridylideneimino-5-[2-<5-(2-dimethylaminomethylbenzimidazolyl)methylthio>ethyl]-1H-1,2,4-triazole-5-amine [Intermediate product of Example Nos. 34–48]

Melting point: 107°–114° C.,
IR (KBr, cm$^{-1}$): 3240, 2950, 1600.
NMR (CDCl$_3$ ppm): 2.25 (6H, s), 2.55–2.95 (2H, m), 3.45 (3H, s), 3.6–3.9 (6H, m), 7.1–7.5 (7H, m), 8.1–9.1 (4H, m, aromatic)

(Example 101)

Absolute methanol solution (81 ml) of 3,4-dimethoxy-1,2,5-thiadiazole-1-oxide (1.62 g) prepared by a method disclosed in Comy et al, J. Org. Chem. 1975, Vol. 40. p 2749 was held at 5° C. Then, the absolute methanol solution (12 ml) of 5-(3-aminopropoxy)-2-(1-piperidinomethyl)benzimidazole (2.68 g) prepared in Example 5 was made to drip into the Example first-mentioned absolute methanol solution while stirring the same for 10 minutes. The mixture was stirred for 30 minutes at the room temperature. Then, the solvent was removed by evaporation under reduced pressure. Then, the oily residue was subjected to a column chromatography by means of silica gel/ethyl acetate:methanol (4:1). Consequently, 3-{3-5-<2-(1-piperidinomethyl)benzimidazolyl>oxy]propyl}amino-4-amino-1,2,5-thiadiazole-1-oxide (3.38 g, 83.9%) was obtained in the form of a light yellow oily substance.

IR (KBr, cm$^{-1}$): 3050–3400, 2950, 1660, 1580, 1440, 1050, 620.
NMR (DMSO-d$_6$+CDCl$_3$, ppm): 1.2–1.8 (6H, b), 1.8–2.3 (2H, t), 1.8–2.6 (4H, b), 3.30–3.65 (2H, t), 3.6 (2H, s), 3.8–4.2 (2H, t), 6.5–7.4 (3H, m, aromatic). 7.4–8.2 (2H, b, disappeared by D$_2$O treatment)

EXAMPLES 102-113

The following compounds were obtained in accordance with the method described in Example 101, using various intermediate products obtained through the foregoing Examples, as well as suitable reaction reagents. The numerals appearing in the pareanthesis attached to the end of the name of each compound shows the number of the Example in which the starting material was produced.

(Example 102)

3-[3-<5-(2-dimethylaminomethylbensimidazolyl)oxi>-propyl]amino-4-ethylamino-1,2,5-thiadiazol-1-oxide [1(A)]

IR (KBr, cm$^{-1}$): 3300, 1610, 1450, 1260, 1160, 1040
NMR (DMSO-d$_6$+CDCl$_3$, ppm): 1.05–1.35 (3H, t), 1.8–2.2 (2H, m), 2.24 (6H, s), 3.1–3.6 (2H, m), 3.56 (2H, s), 3.8–4.2 (2H, t), 6.6–7.3 (3H, m, aromatic)

(Example 103)

3-[2-<5-(2-dimethylaminomethylbenzimidazolyl)methylthio>ethyl]amino-4-amino-1,2,5-thiadiazol-1-oxide [Intermediate product A of Example Nos. 34–48]

IR (KBr, cm$^{-1}$): 3200, 1660, 1580, 1440, 1040, 805, 620
NMR (DMSO-d$_6$+CDCl$_3$, ppm): 2.3 (6H, s), 2.4–2.7 (2H, m), 3.3–3.7 (2H, m), 3.7 (2H, s), 3.8 (2H, s), 7.1–7.5 (3H, m, aromatic), 7.6–8.4 (3H, b, disappeared by D$_2$O treatment)

(Example 104)

3-[2-<5-(2-dimethylaminomethylbenzimidazolyl)methylthio>ethyl]amino-4-amino-1,2,5-thiadiazole-1.1-dioxide [Intermediate product A of Example Nos. 34–48]

NMR (DMSO-d$_6$+CDCl$_3$, ppm): 2.25 (6H, s), 2.3–2.7 (2H, m), 3.3–3.5 (2H, m), 3.6 (2H, s), 3.8 (2H, s), 7.0–7.5 (3H, m, aromatic), 7.7–8.2 (3H, b, disappeared by D$_2$O treatment)

(Example 105)

3-{2-[5-<2-(1-piperidinomethyl)benzimidazolyl>methylthio]ethyl}amino-4-amino-1,2,5-thiadiazole-1-oxide [Intermediate product B of Example Nos. 34–48]

IR (KBr, cm$^{-1}$): 3200, 2800, 1660, 1580, 1440, 1340, 1040
NMR (DMSO-d$_6$+CDCl$_3$, ppm): 2.25 (6H, s), 2.40–2.82 (2H, t), 3.2–3.7 (2H, b), 3.65 (2H, s), 3.8 (2H, s), 6.9–7.5 (3H, m), 7.5–7.8 (1H, b), 8.0–8.4 (1H, b), 8.35–8.8 (1H, b)

(Example 106)

3-[2-<5-(2-dimethylaminomethylbenzimidazolyl)methylthio>ethyl]amino-4-methylamino-1,2,5-thiadiazole-1-oxide [Intermediate product A of Example Nos. 34–48]

IR (KBr, cm$^{-1}$): 3280, 1608, 1418, 1040, 842
NMR (DMSO-d$_6$, ppm): 2.3 (6H, s), 2.6 (3H, d), 2.9 (2H, s), 3.2–3.6 (2H, b), 3.6 (2H, s), 3.8 (2H, s), 7.0–7.5 (3H, b, aromatic)

(Example 107)

3-{2-[5-<2-[1-piperidinomethyl)benzimidazolyl methylthio]ethyl}amino-4-methylamino-1,2,5-thiadiazole-1-oxide [Intermediate product B of Example Nos. 34–48]

IR (KBr, cm$^{-1}$): 3220, 2800, 1640, 1540, 1440
NMR (DMSO-d$_6$+CDCl$_3$, ppm): 1.1–1.7 (6H, b), 2.1–2.6 (4H, b), 2.6–2.9 (3H, b), 3.2–3.5 (2H, b), 3.7 (2H, s), 3.8 (2H, s), 7.0–7.5 (3H, m, aromatic), 8.2–8.7 (1H, b, disappeared by D$_2$O treatment)

(Example 108)

3-[2-<5-(2-dimethylaminomethylbenzimidazolyl)methylthio>ethyl]amino-4-ethylamino-1,2,5-thiadiazole-1-oxide [Intermediate product of Example Nos. 34–48]

NMR (CDCl$_3$, ppm): 1.1–1.4 (3H, t), 2.3 (6H, s), 2.5–2.8 (2H, m), 3.5–3.7 (2H, m), 3.8 (2H, s), 3.5–3.7 (2H, m), 4.0 (2H, s), 4.2–4.6 (2H, m), 7.1–7.6 (3H, m, aromatic)

(Example 109)

3-[2-<5-(2-dimethylaminomethylbenzimidazolyl)methylthio>ethyl]amino-4-(2-propinylamino)-1,2,5-thiadiazole-1-oxide [Intermediate product A of Example Nos. 34–48]

IR (KBr, cm$^{-1}$): 3300, 2100, 1610, 1020, 840
NMR (DMSO-d$_6$, ppm): 2.2 (6H, s), 2.4–2.8 (2H, m), 3.2–3.6 (2H, m), 3.6 (2H, s), 3.9 (2H, s), 4.1 (2H, s), 7.0–7.5 (3H, m, aromatic), 7.9–8.6 (2H, b, disappeared by D$_2$O treatment)

(Example 110)

3-[2-<5-(2-dimethylaminomethylbenzimidazolyl)methylthio>ethyl]amino-4-(2-propynylamino)-1,2,5-thiadoazole-1,1-dioxide [Intermediate product A of Example Nos. 34-48]

IR (KBr, cm$^{-1}$): 3290, 2103, 1625, 1540, 1450, 1305
NMR (DMSO-d$_6$, ppm): 2.2 (6H, s), 2.3-2.8 (2H, t), 3.1-3.6 (2H, m), 3.1 (2H, s), 3.8 (2H, s), 4.1 (2H, d), 6.9-7.5 (3H, m, aromatic)

(Example 111)

3-[3-<5-(2-guanidinobenzimidazolyl)thio>propyl]amino-4-amino-1,2,5-thiadiazol-1-oxide [17(A)]

IR (KBr, cm$^{-1}$): 3100-3350 (Broad), 1610, 1530, 1450, 1370, 1030, 920
NMR (DMSO-d$_6$+CDCl$_3$, ppm): 1.5-2.2 (2H, m), 2.7-3.1 (2H, t), 3.2-3.7 (2H, b), 4.3-5.8 (4H, b, disappeared by D$_2$O treatment), 6.5-6.9 (1H, b, disappeared by D$_2$O treatment), 6.9-7.3 (3H, t, aromatic), 7.6-8.1 (1H, b, disappeared by D$_2$O treatment)

(Example 112)

3-[2-<5-[2-guanidinobenzimidazolyl)thio>ethyl]amino-4-amino-1,2,5-thiadiazole-1-oxide [16(A)]

IR (KBr, cm$^{-1}$): 3300, 1610, 1520, 1450, 1270, 1040, 860
NMR (DMSO-d$_6$+CDCl$_3$, ppm): 1.0-1.8 (3H, t), 2.85-3.7 (6H, m), 3.8-5.0 (4H, b, disappeared by D$_2$O treatment), 6.8-7.3 (3H, d, aromatic), 6.5-7.0 (1H, b, disappeared by D$_2$O treatment)

(Example 113)

3-N-[3-<5-(2-guanidinobenzimidazolyl)thio>propyl]amino-4-ethylamino-1,2,5-thiadiazole-1-oxide [17(A)]

aka: 3300, 1610, 1460, 1270, 1040, 860, 800
NMR (DMSO-d$_6$+CDCl$_3$, ppm): 1.0-1.4 (3H, t), 1.5-2.1 (2H, t), 2.6-3.0 (2H, t), 3.1-3.6 (4H, m), 4.9-6.0 (4H, b, disappeared by D$_2$O tretment), 6.8-7.4 (3H, q, aromatic), 7.5-8.1 (1H, b, disappeared by D$_2$O treatment)

EXAMPLES 114-131

Preparation of Intermediate Product F

Sodium hydride (a 50% oil solution, 20 g) was added to P-nitrophenol (52 g) in N,N-dimethylformamide (375 ml) to prepare a sodium salt of p-nitrophenol.
Then, the product sodium salt was made to react with 4-chlorobutyl nitrile (58 g) for 48 hrs at 50° C. to yield 4-(4-nitrophenoxy)butylnitrile (51 g). This nitro compound (16 g) was reduced under pressure of 70 atm in tetrahydrofuran (140 ml) using 5% palladium carbon as a catalyst. Then, with the addition of triethylamine (9.83 g), the product was made-react with chloroacetylchloride (11 g)-yield 4-(3-cyanopropyl)oxychloroacetanilide (18.5 g). The thus obtained chloroacetanilide compound (9.2 g) was nitrated by nitric acid (specific weight 1.42 3.8 ml) in acetic acid (90 ml) and, after a reaction with dimethylamine, the nitrated product as subjected to a reduction under the pressure of 70 atm, followed by a ring closure with heating in xylene (200 ml) to yield 5-[(3-cyanopropyl)oxy]-2-dimethylaminomethylbenzimidazole (5.9 g) as a light brown oil product.

IR (liq, cm$^{-1}$): 2250, 1460
NMR (DMSO-d$_6$, ppm): 1.7-2.7 (2H, m), 2.22 (6H, s), 2.58 (2H, t), 3.6 (2H, s), 3.96 (2H, t), 6.5-7.4 (3H, m)

Preparation of Intermediate Product G

Using, suitable reaction reagents, 5-[(3-cyanopropyl)oxy]-2-(1-piperidinomethyl)benzimidazole was prepared in accordance with the process for the preparation of the intermediate product F.

Oily product.
IR (liq, cm$^{-1}$): 2250.
NMR (DMSO-d$_6$, ppm): 1.4-1.9 (6H, m), 2.08 (2H, t), 2.3-2.8 (6H, m), 3.87 (2H, s), 3.99 (2H, t), 6.6-7.6 (3H, m), 8.73 (1H, b, disappeared by D$_2$O treatment)

Preparation of Intermediate Product H

5-Chloromethyl-2-dimethylaminomethylbenzimidazole, 2hydrochloride (melting point 248.4° C., 3.64 g) was produced by subjecting 2-dimethylaminomethyl-5-hydroxymethylbenzimidazole (3 g) and thionylchloride (10.5 ml) to a 4-hour refluxing with heat. 2-Mercaptopropionitrile (1.05 g) was changed into sodium salt by sodium ethoxide and, at a temperature of 0° C., methanol solution of the above-mentioned chloromethyl compound was added gradually and the mixture was stirred through one whole night at the room temperature to yield 5-[(2-cyanoethyl)thiomethyl]-2-dimethylaminomethylbenzimidazole (3.2 g).

IR (liq, cm$^{-1}$): 2950, 2260
NMR (DMSO-d$_6$, ppm): 2.21 (6H, s), 2.6-2.8 (4H, m), 3.6 (2H, s), 3.88 (2H, s), 6.9-7.45 (3H, m).

The following intermediate products I, J and K were prepared by using suitable reaction reagents, in accordance with the above-explained process for producing the intermediate product H.

Intermediate Product I

5-[(2-cyanoethyl)thiomethyl]-2-(1-piperidinylmethyl)benzimidazole mp: 127° to 128° C.
IR (KBr, cm$^{-1}$): 2950, 2800, 2270, 1630.
NMR (CDCl$_3$, ppm): 1.51 (6H, m), 2.54 (4H, m), 2.3-2.8 (4H, m), 3.72 (2H, s), 3.85 (2H, s), 6.9-7.6 (3H, m)

Intermediate Product J

5-[(3-cyanopropyl)thiomethyl]-2-dimethylaminomethylbenzimidazole

Oily product.
IR (liq, cm$^{-1}$): 2960, 2270
NMR (CDCl$_3$, ppm): 1.9-2.2 (2H, m), 2.32 (6H, s), 2.5-2.9 (2H, m), 3.0-3.4 (2H, m), 3.44 (2H, s), 3.71 (2H, s), 7.6-7.6 (3H, m).

Intermediate Product K

5-[(3-cyanopropyl)thiomethyl]-2-(1-piperidinylmethyl)benzimidazole

Oily product.
IR (liq, cm$^{-1}$): 2250.
NMR (CDCl$_3$, ppm): 1.3-1.8 (6H, m), 1.8-2.2 (2H, m), 3.1-3.6 (2H, m), 3.72 (2H, s), 3.75 (2H, s), 6.9-7.5 (3H, m).

(Example 114)

The above-mentioned intermediate product F (2.95 g) was dissolved in anhydrous chloroform (22 ml) and ethanol (0.96 ml) and the solution was blown by dry hydrochloride gas for 1 hour at 0° C. The solution was then left still through one whole night at 0° C. The reaction solution was then poured into an ice aqueous solution of potassium carbonate to separate organic layer and, after drying the extract of the aqueous layer, the solvent was removed. Then, ethanol solution (24 ml) containing propargylamine (1.25 g) was added to the residue and the mixture was stirred through one whole night at the room temperature. After the completion of the reaction, the solvent was removed by reducing the pressure, and the residue was subjected to column chromatography by using silica gel/ethyl acetate:-methanol (4:1) to yield N-propagyl-4-[5-(2-dimethylaminomethylbenzimidazole)oxy]butyroamidine (1.5 g, yield 48%) as a light yellow oily product.

IR (liq, cm$^{-1}$): 2150, 1670, 1450, 1165.

NMR (DMSO-d$_6$, ppm): 1.93 (1H, s), 1.7–2.6 (4H, m), 2.25 (6H, s), 3.7–4.2 (2H, s), 3.66 (2H, s), 3.7–4.2 (2H, b), 6.2–8.5 (5H, m).

In accordance with the above-explained process, the following compounds were prepared by using one of the intermediate products F to K and suitable reaction reagents. The product mentioned in the parenthesis at the end of the name of the compound is the starting intermediate product.

(Example 115)

N-cyano-4-[5-(2-dimethylaminomethylbenzimidazolyl)oxy]butyroamidine (Intermediate product F)

IR (KBr, cm$^{-1}$): 3200, 2200, 1660, 1570.

NMR (DMSO-d$_6$, ppm): 1.8–2.8 (4H, m), 2.28 (6H, m), 2.64 (2H, s), 3.97 (2H, t), 6.2 (2H, b), 6.6–7.5 (3H, m), 8.3 (1H, b, disappeared by D$_2$O treatment)

(Example 116)

N-cyano-4-[5-<2-(1-piperidinomethyl)benzimidazolyl->oxy]butyroamidine (Intermediate Product G)

Melting point: 51°–53° C.

IR (KBr, cm$^{-1}$): 2950, 2180, 1660, 1570.

NMR (DMSO-d$_6$, ppm): 1.1–1.8 (6H, m), 1.7–2.8 (4H, m), 2.1–3.0 (4H, m), 3.92 (2H, t), 6.5–7.4 (3H, m), 8.13 (2H, b, disappeared by D$_2$O treatment)

(Example 117)

N-carbamoyl-4-[5-(2-dimethylaminomethylbenzimidazolyl)oxy]butyroamidine.3hydrochloride (Intermediate Product F)

Melting point: 113°–114° C.

IR (KBr, cm$^{-1}$): 3320, 1743, 1560, 1180.

NMR (DMSO-d$_6$, ppm): 2.0–3.0 (4H, m), 2.3 (6H, s), 4.13 (2H, b), 4.88 (2H, s), 6.9–7.3 (3H, m, aromatic).

(Example 118)

N-carbamoyl-4-[5-<2-(1-piperidinomethyl)benzimidazolyl>oxy]butyroamidine.3hydrochloride (Intermediate Product G)

Melting point: 199°–201° C.

IR (KBr, cm$^{-1}$): 3300, 2500, 1735, 1550.

NMR (DMSO-d$_6$, ppm): 1.3–2.1 (6H, m), 2.2–3.2 (4H, m), 4.10 (2H, t), 4.75 (2H, s), 6.9–8.0 (10H, m).

(Example 119)

N-sulfamoyl-4-[5-<2-(1-piperidinomethyl)benzimidazolyl>oxy]butyroamidine (Intermediate Product G)

Melting point: 59°–61° C.

IR (KBr, cm$^{-1}$): 3350, 3250, 2950, 1640.

NMR (DMSO-d$_6$, ppm): 1.1–1.8 (6H, m), 2.1–2.7 (4H, m), 3.60 (2H, s), 3.93 (2H, t), 1.9 (4H, m), 6.2–7.5 (6H, b).

(Example 120)

N-benzoylamino-4-[5-(2-dimethylaminomethylbenzimidazolyl)oxy]butyroamidine (Intermediate Product F)

Melting point: 94°–96° C.

IR (KBr, cm$^{-1}$): 3200, 1740, 1670, 1540.

NMR (DMSO-d$_6$, ppm): 1.8–2.7 (4H, m), 2.3 (6H, s), 3.6 (2H, s), 3.7–4.2 (2H, m), 6.6–7.1 (3H, m), 7.1–8.0 (5H, m), 7.3–7.5 (3H, b)

(Example 121)

N-sulfamoyl-3-[5-(2-dimethylaminomethylbenzimidazolyl)methylthio]propionamidine Intermediate Product H)

Melting point: 74.2° C.

IR (KBr, cm$^{-1}$): 3200, 2950, 1670, 1350, 1150.

NMR (DMSO-d$_6$, ppm): 2.21 (6H, s), 2.4–2.7 (4H, m), 3.6 (2H, s), 3.8 (2H, s), 6.75–6.95 (2H, b, disappeared by D$_2$O treatment), 6.9–7.4 (3H, m, aromatic), 8.0–8.2 (1H, b, disappeared by D$_2$O treatment)

(Example 122)

N-sulfamoyl-4-[5-(2-dimethylaminomethylbenzimidazolyl)methylthio]butyroamidine (Intermediate Product J)

IR (KBr, cm$^{-1}$): 3200–3400, 1640, 1565, 1450

NMR (DMSO-d$_6$, ppm): 1.7–2.7 (6H, m), 2.26 (6H, s), 3.63 (2H, s), 3.76 (2H, s), 6.9–7.4 (3H, m), 6.3–8.0 (1H, b, disappeared by D$_2$O treatment)

(Example 123)

N-sulfamoyl-3-[5-<2-(1-piperidinomethyl)benzimidazolyl>methylthio]propionamidine (Intermediate Product I)

Melting point: 62°–65° C.

IR (KBr, cm$^{-1}$): 3350, 3350, 3250, 1640

NMR (DMSO-d$_6$, ppm): 1.2–1.7 (6H, m), 2.2–2.7 (4H, m), 2.2–2.7 (2H, m), 3.5–3.9 (2H, m), 3.63 (2H, s), 3.81 (2H, s), 6.33 (3H, b), 6.9–7.5 (3H, m), 8.13 (1H, b, disappeared by D$_2$O treatment)

(Example 124)

N-sulfamoyl-4-[5-<2-(1-piperidinomethyl)benzimidazolyl>methylthio]butyroamidine (Intermediate Product K)

Melting point: 60°–65° C.

IR (KBr, cm$^{-1}$): 3350, 3250, 2950, 1640

NMR (CD$_3$OD, ppm): 1.2–1.8 (6H, m), 1.2 (2H, t), 1.0–2.6 (4H, m), 2.1–2.7 (4H, m), 3.73 (2H, s), 3.76 (2H, s), 6.9–7.1 (3H, m).

(Example 125)

N-cyano-3-[5-(2-dimethylaminomethylbenzimidazolyl)-methylthio]propionamidine (Intermediate Product H)

Melting point: 63°–65° C.

IR (KBr, cm$^{-1}$): 2200, 1660, 1565, 1450.

NMR (DMSO-d$_6$, ppm): 2.21 (6H, s), 2.64 (4H, s), 3.58 (2H, s), 3.82 (2H, s), 6.9–7.5 (3H, m, aromatic), 7.8–8.8 (2H, b, disappeared by D$_2$O treatment)

(Example 126)

N-cyano-4-[5-(2-dimethylaminomethylbenzimidazolyl)-methylthio]butyroamidine (Intermediate Product J)

IR (KBr, cm$^{-1}$): 3170, 2170, 1655, 1560, 1450

NMR (CD$_3$OD, ppm): 1.7–2.7 (6H, m), 2.3 (6H, s), 3.7 (2H, s), 3.75 (2H, s), 6.9–7.5 (3H, m, aromatic)

(Example 127)

N-cyano-3-[5-<2-(1-piperidinomethyl)benzimidazolyl>methylthio]propionamidine (Intermediate Product K)

Melting point: 57°–58° C.

IR (KBr, cm$^{-1}$): 2950, 2190, 1660, 1570

NMR (DMSO-d$_6$, ppm): 1.2–1.8 (6H, b), 2.2–2.7 (4H, b), 2.66 (4H, s), 3.62 (2H, s), 3.81 (2H, s), 6.8–7.5 (3H, m), 8.0–8.3 (1H, b, disappeared by D$_2$O treatment)

(Example 128)

N-propargyl-3-<5-(2-dimethylaminomethylbenzimidazolyl>methylthio]propionamide (Intermediate Product H)

IR (KBr, cm$^{-1}$): 3300, 2100, 1650, 1460.

NMR (DMSO-d$_6$, ppm): 2.0–2.7 (4H, m), 2.0–2.7 (1H, s), 2.29 (6H, s), 3.71 (2H, s), 3.80 (2H, s), 3.87 (2H, d), 6.0–7.2 (2H, b, disappeared by D$_2$O treatment), 7.0–7.5 (3H, m, aromatic).

(Example 129)

N-carbamoyl-3-[5-(2-dimethylaminomethylbenzimidazolyl)methylthio]propionamidine (Intermediate Product H)

Melting point: 42°–45° C.

IR (KBr, cm$^{-1}$): 3200, 1620, 1530, 1030.

NMR (DMSO-d$_6$, ppm): 2.23 (6H, s), 2.3–2.9 (4H, m), 3.61 (2H, s), 3.81 (2H, s), 6.1–6.8 (2H, b), 6.9–7.5 (3H, m), 8.15 (1H, s).

(Example 130)

N-carbamoyl-3-[5-<2-(1-piperidinomethyl)benzimidazolyl>methylthio]propionamidine (Intermediate Product I)

Melting point: 49°–52° C.

IR (KBr, cm$^{-1}$): 3150, 2950, 1700, 1620.

NMR (DMSO-d$_6$, ppm): 1.2–1.8 (6H, m), 1.7–2.1 (4H, m), 2.58 (2H, t), 3.5–3.9 (2H, m), 3.62 (2H, s), 3.78 (2H, s), 6.8–7.5 (3H, m, aromatic)

(Example 131)

N-carbamoylamine-3-<5-(2-dimethylaminomethylbenzimidazolyl>methylthio)propionamidine (Intermediate Product H)

Melting point: 78°–80° C.

IR (KBr, cm$^{-1}$): 3300, 1680, 1580, 1450.

NMR (DMSO-d6, ppm): 2.3–2.8 (4H, b), 2.36 (6H, m), 3.28 (4H, s), 5.2–6.5 (5H, b, disappeared by D$_2$O treatment), 6.9–7.5 (3H, m, aromatic).

| Example of film coated tablets | |
| --- | --- |
| Compound of Example 70 | 150 g |
| Avicel (Trademark for microcrystalline cellulose, manufactured by Asahi Chemical Industries, Ltd.) | 40 g |
| Corn starch | 30 g |
| Magnesium stearate | 2 g |

| Example of film coated tablets -continued | |
| --- | --- |
| Hydroxypropylmethylcellulose | 10 g |
| Polyethylene glycolcellulose | 3 g |
| Castor oil | 40 g |
| Methanol | 40 g |

Compound of Example 70, Avicel, corn starch and magnesium stearate were admixed together and ground, and then compressed into tablets with a punch having a diameter of 10 mm. The tablets obtained were coated with a film coating agent consisting of hydroxypropylmethylcellulose, polyethylene glycol-6000, castor oil and methanol, to prepare film coated tablets.

| Example of coated tablets | |
| --- | --- |
| Compound of Example 78 | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dried sodium lauryl sulfate | 3.0 g |
| Dried magnesium stearate | 3.0 g |
| Ethanol | q.s. |

Compound of Example 78, Citric acid, lactose, dicalcium phosphate, Pluronic F-68 and sodium lauryl sulfate were admixed together and the obtained mixture was sieved through a No. 60 sieve then the sieved mixture was wet granulated with an alcoholic solution containing polyvinylpyrrolidone, Carbowax 1500 and 6000. The granulated product was made into paste like lump by adding ethanol if necessary. Corn starch was added thereto and the mixture was well mixed until uniform granules were formed. The granules were sieved through a No. 1 sieve, and the sieved granules were placed in a tray and dried at 100° C. in an oven for 12–14 hours. The dried granules were sieved through a No. 16 sieve, and to the sieved granules were added dried sodium lauryl sulfate and dried magnesium stearate. Then the whole mixture was mixed well and compressed into the desired form by using a tablet machine to obtain tablets to be used for the core portions of coated tablets. The core portions were treated with a varnish, and further the treated surface thereof was coated with talc for preventing the surface from absorbing moisture. The treated surface of the core portions was further coated with a primary coating layer, and further coated with a varnish to make a sufficient number of layers for preparing coated tablets for oral administration. In order to make the coated core portions of the tablets into complete spherical form and to make the treated surface smooth, the coated tablets were further coated with primary coating layers and smoothing coating layers. The coated tablets were color coated until the desired color of the surface was obtained. After the coated tablets were dried, the surface thereof was polished to give the tablets uniform gloss.

| Example of preparation of injection composition | |
| --- | --- |
| Compound of Example 97 | 5.0 g |
| Polyethylene glycol (Molecular weight: (Molecular weight: 4000) | 0.3 g |

| Example of preparation of injection composition | |
|---|---|
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

The above-mentioned Methylparaben, propylparaben, sodium metabisulfite and sodium chloride were dissolved in a half amount of the above-mentioned distilled water at 80° C. with stirring. The solution obtained was cooled to 40° C., and the present compound, polyethylene glycol and polyoxyethylene sorbitan monooleate were dissolved, in this order, in the above-mentioned solution. To the solution thus obtained was added the remaining amount of distilled water for injection to make the volume of the injection composition into the predetermined volume. The solution was then sterilized by sterilizing filtration using a suitable filter paper to prepare an injection preparation.

PHARMACOLOGICAL EFFECT OF THE COMPOUNDS OF THE INVENTION

Hitherto, histamine $H_2$ receptor antagonists have been known to have a function to inhibit animal and human gastric acid secretion, as disclosed in J. Int. Med. Res., 3,86, 1975 (Plybulcomb et al). The histamine $H_2$ receptor antagonists are also effective in curing peptic ulcer as reported by Gray et al in Lancet, 1,8001 (1977). Anti secretory test in pylorus ligated rats negative chronotropic test in guinea pig right atrium are well known as methods of standard animal test for examining the histamine $H_2$ receptor antagonists.

Therefore, in order to evaluate the compounds of the invention, we examined an anti-oxynitic effect in pylorusligated rat, as well as a negative chronotropic effect in guinea pig right atria with these compound. For reference, "cimetidine" which is broadly used clinically as an antipeptic-ulcer agent having histamine $H_2$ receptor antagonistic effect, was examined in the same test.

(A) Anti-secretory Effect in Pylorus-ligated Rat

This test was conducted in accordance with a modified method of Watanabe et al, in "Applied Pharmacology", 1969, Vol. 3(1), pp 7–14.

After 24 hr fasting, male wistar rats weighing about 160 g were anesthetized by intraperitoreal injection of urethans 1.2 g/kg. Then, after ligating the pylorus and the esophagus, the proventriculus was incised and a double polyethylene cannula was inserted. The gastric wall was washed out with 5 ml of physiological saline every 30 minutes and the amount of acid contained in the saline after washing was measured by titration. After measuring the basal acid secretion of the pylorus ligated rats three times, the compounds of the invention, 2 mg/kg, were administered subcutaneously and, 30 minutes thereafter, histamine 3 mg/kg, was administered also subcutaneously. Then, the amounts of acid secretion were measured for 3 hours. Three points exhibiting the highest increment of acid secretion were selected in respective time intervals and the mean value of the increment values was used as the acid secretion increment of each group. Then, an inhibition rate was calculated in accordance with the following formula, in relation to the increment values measured for the control group.

Acid secretion inhibition ratio (%) =

$$\left[1 - \frac{\text{acid secretion increment value in specimen group}}{\text{acid secretion increment value in control group}}\right] \times 100$$

One group included five examples.

(B) Measurement of Histamine $H_2$ Receptor Inhibition Effect by Isolated Guinea Pig Right Atrium Preparation Male Hartley Guinea Pig weighing around 400 g was sacrificed by decapitation, and right atrium was isolated. The right atrium was suspended in an organ bath (50 ml) containing modified Ringer solution. Under application of a tensile load of 1 g, the heart rate was recorded by means of a polygraph. Histamine was applied cumulatively from $1 \times 10^{-7}$ mol to $3 \times 10^{-4}$ mol and a cumulative dosage response curve was drawn. Then, $5 \times 10^{-6}$ mol of the sample was administered 3 minutes prios to histamine application. The negative logarithmic value ($pA_2$) of the specimen molarity required for shifting the curve to the right to double concentration was calculated. The experimental value shows the mean of five examples.

TABLE 1

| | Effects of Compounds of the Invention | |
|---|---|---|
| Example Nos. | (A) inhibitory effect of acid secretion (%) at 2 mg/kg s.c. | (B) inhibitory effect of histamine $H_2$ receptor in atria ($pA_2$ value) |
| 2 | 75** | 5.82 |
| 3 | 54* | 5.93 |
| 5 | 65** | 5.86 |
| 25 | 99** | 6.20 |
| 27 | 73** | 4.79 |
| 28 | 64** | 5.61 |
| 30 | 78** | 5.86 |
| 34 | 52* | 6.08 |
| 35 | 64** | 6.19 |
| 37 | 38 | 5.78 |
| 42 | 93** | 5.84 |
| 44 | 57* | 6.20 |
| 46 | 72** | 5.93 |
| 59 | 74** | 6.05 |
| 60 | 56** | 5.45 |
| 61 | 64** | 5.51 |
| 62 | 84** | 6.20 |
| 63 | 78** | 5.39 |
| 64 | 76** | 5.23 |
| 66 | 100** | 5.71 |
| 67 | 93** | 5.33 |
| 68 | 90** | 5.02 |
| 70 | 102** | 5.61 |
| 72 | 53** | 6.07 |
| 73 | 91** | 6.20 |
| 76 | 102** | 5.91 |
| 78 | 107** | 5.75 |
| 83 | 78** | 5.39 |
| 84 | 75** | 5.66 |
| 85 | 46* | 5.71 |
| 87 | 84** | 6.22 |
| 91 | 81** | 5.19 |
| 92 | 92** | 5.26 |
| 96 | — | 6.03 |
| 97 | 76** | 6.05 |
| 100 | 72** | 5.75 |
| 101 | 97** | 5.53 |
| 102 | 68** | 5.66 |
| 103 | 98** | 6.24 |
| 104 | 96** | 5.71 |
| 105 | 92** | 6.08 |
| 106 | 89** | 6.27 |

TABLE 1-continued

Effects of Compounds of the Invention

| Example Nos. | (A) inhibitory effect of acid secretion (%) at 2 mg/kg s.c. | (B) inhibitory effect of histamine $H_2$ receptor in atria (p$A_2$ value) |
|---|---|---|
| 108 | 77** | 5 84 |
| 109 | 74** | 6.12 |
| 110 | 68** | 5.80 |
| 113 | 63** | 5.07 |
| 121 | 76** | 6.25 |
| 122 | 32** | 5.61 |
| 129 | 72** | 6.12 |
| reference compound (Cimetidine) | 63** | 6.10 |

In comparison with control group by student's t test (Dunnett type comparison):
* = significant difference at critical rate 5%
** = significant difference at critical rate 1%

TABLE 2

Effects of Compound of Example 70 of Invention and Cimetidine on Acid Secretion in Pylorus-ligated Rats

| compound | dosage μmol/kg | acid secretion inhibition % | ED 50 μmol/kg | effective ratio |
|---|---|---|---|---|
| compound of Example 70 | 0.067 | 35 | 0.11 | 25.2 |
|  | 0.204 | 71 | *(0.039– |  |
|  | 0.613 | 93 | 0.321) |  |
| cimetidine | 2.0 | 37 | 2.77 | 1.0 |
|  | 5.9 | 75 | *(0.63– |  |
|  | 17.8 | 83 | 12.48) |  |

The number of rats used in each test was 5.
Mark * shows 95% confidence limit.

As shown in Tables 1 and 2, in the acid secretion inhibition test, most of the compounds of the invention showed higher activity that the "cimetidine" used as the reference compound. On the other hand, in the test for examining the histamine $H_2$ receptor inhibition effect in the right atrium preparation, some of the compounds of the invention showed an activity equal to or higher than that of "cimetidine". Thus, the compounds of the invention are quite promising as a remedy for peptic ulcer.

Pharmacological Test

The test compounds were administered orally to Wistar male rats weighing from 160 to 180 g so as to investigate the effect on gastric mucus secretion. The amount of mucus was determined using alcian blue color specifically bonding with acid mucosaccharides, and was expressed by the amount of color bonding with a unit weight (OD units/g tissue). The test compounds were administered at a dosage of 10 mg/kg twice a day for 7 days, and the rats were sacrificed one hour after the final administration in the morning on the 8th day by cervical dislocation. After laparatomy, the stomach was removed. After removal of the forestomach, an incision was made along the greater curvatura. The stomach was lightly washed with a 0.25M sucrose solution cooled with ice. The weight was determined after absorption of water with a filter paper.

Then, the stomach was exposed for 1.5 hrs in 10 ml of 0.25M sucrose solution containing 0.1% alcian blue 8 GX for staining. Then, the stained stomach was washed with 10 ml of a 0.25M sucrose for 15 min, being dipped in 15 ml of a 0.5M $MgCl_2$ for 2 hrs so as to elute alcian blue combined with the mucus. Finally, 10 ml of ethyl ether was added, and the mixture was shaken vigorously. The floating substances were removed, and the aqueous layer was quantified by measuring the absorption at 605 nm.

The above procedures were carried out at room temperature.

The results obtained are shown in Table 3.

TABLE 3

Effect of $H_2$—antagonist on gastric mucus secretion in rats

| Compounds | Dosage (mg/kg × 2/day) | No. of rats | Alcian blue binding (OD units/g tissue) | % Change |
|---|---|---|---|---|
| Control (0.5% CMC) | 4 ml/kg | 7 | 0.27 ± 0.01 | — |
| Example 103 | 10 | 7 | 0.31 ± 0.02* | +14.8* |
| Control (0.5% CMC) | 4 ml/kg | 7 | 0.36 ± 0.02 | — |
| Example 8 | 10 | 7 | 0.55 ± 0.04** | +52.5** |
| Example 78 | 10 | 7 | 0.45 ± 0.04 | +24.6 |
| Example 97 | 10 | 7 | 0.49 ± 0.02** | +37.4** |

*significant difference at critical rate 5%.
**significant difference at critical rate 1%.

Toxicity Test

Male dd-mice were divided into groups of 5 and fasted for 8 hours. The test compounds were administered orally to the mice weighing from 19.7 g. to 22.0 g. The mice were observed survival or death as well as the general symptoms over 7 days after the administration of the compounds. The value of $LD_{50}$ for each compound was estimated from the mortality observed on the basis of the Litchfield-Wilcoxon method. The results are shown in Table 4.

TABLE 4

| Test compound | $LD_{50}$ (mg/kg) |
|---|---|
| Compound of example 70 | 2800 |
| Compound of example 103 | >4000 |

In a similar test, the test compound of example 27, 35, 66, 84, 97, 104, 118, 125 or 129 was administered orally to the mice at a dose of 1500 mg/kg. The values of $LD_{50}$ for all of the tested compounds were more than 1500 mg/kg.

We claim:
1. A compound of formula:

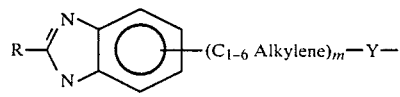

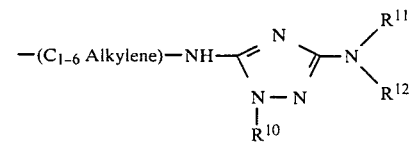

wherein
R is (a) hydrogen; (b) $C_{1-6}$alkyl; (c) an unsubstituted amidino or a $C_{1-6}$ alkyl substituted amidino; (d) an unsubstituted guanidino or a $C_{1-6}$ alkyl substituted guanidino; (e) a

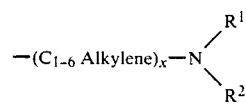

group wherein x is 0 or 1,
R¹ and R² are independently hydrogen or $C_{1-6}$ alkyl,
or

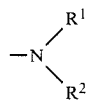

is an unsubstituted heterocyclic radical which is a member selected from the group consisting of (1) morpholino, (2) piperidino, (3) pyrrolidino, (4) piperazino, (5) thiomorpholino, and (6) morpholino, piperidino, pyrrolidino, piperazino, thiomorpholino substituted by $C_{1-6}$ alkyl; Y is independently a —NH—, an —O—, or a —S—;

m is 0 or 1;

$R^{10}$ is hydrogen, an unsubstituted phenyl or a phenyl substituted by $C_{1-4}$ alkylenedioxy, $C_{1-6}$ alkoxy or halogen, or a mono- or di-$C_{1-6}$ alkylamino-$C_{1-6}$ alkyl;

$R^{11}$ and $R^{12}$ are independently hydrogen, $C_{1-6}$ alkyl or

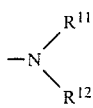

is a heterocyclic radical which is a member selected from the group consisting of (1) morpholino, (2) piperidino, (3) pyrrolidino, (4) piperazino, (5) thiomorpholino, (6) pyridylideneimino and (7) morpholino, piperidino, pyrrolidino, piperazino, thiomorpholino, pyridylideneimino substituted by $C_{1-6}$ alkyl, and pharmaceutically compatible salts thereof, solvates and hydrates thereof.

2. The compound according to claim 1 which is 5-{3-[5-<2-(1-piperidinomethyl)benzimidazolyl>oxy]propyl-1H-}1,2,4-triazole-3,5-diamine.

3. The compound according to claim 1 which is 1-methyl-5-[3-<5-(2-dimethylaminomethylbenzimidazolyl)oxy>propyl]-1H-1,2,4-triazole-3,5-diamine.

4. The compound according to claim 1 which is 1-methyl-5-[4-<5-(2-dimethylaminomethylbenzimidazolyl)oxy>butyl]-1H-1,2,4-triazole-3,5-diamine.

5. The compound according to claim 1 which is 1-methyl-5-{3-[5-<2-(1-pyrrolidinomethyl)benzimidazolyl>oxy]propyl}-1H-1,2,4-triazole-3,5-diamine.

6. The compound according to claim 1 which is 1-methyl-5-{3-[5-<2-(1-piperidinomethyl)benzimidazolyl>oxy]propyl}-1H-1,2,4-triazole-3,5-diamine.

7. The compound according to claim 1 which is 1-methyl-5-[3-<5-(2-guanidinobenzimidazolyl)oxy>-propyl]-1H-1,2,4-triazole-3,5-diamine.

8. The compound according to claim 1 which is 5-[2-<5-(2-dimethylaminomethylbenzimidazolyl)methylthio>ethyl]-1H-1,2,4-triazole-3,5-diamine.

9. The compound according to claim 1 which is 1-methyl-5-[2-<5-(2-dimethylaminomethylbenzimidazolyl)-methylthio>ethyl]-1H-1,2,4-triazole-3,5-diamine.

10. The compound according to claim 1 which is 1-methyl-3-dimethylamino-5-[2-<5-(2-dimethylaminomethylbenzimidazolyl)methylthio>ethyl]1H-1,2,4-triazole-5-amine.

11. The compound according to claim 1 which is 1-methyl-3-pyridylideneimino-5-[2-<5-(2-dimethylaminomethylbenzimidazolyl) methylthio>ethyl]-1H-1,2,4-triazole-5-amine.

12. The compound according to claim 1 which is 5-{3-[5-<2-(1-pyrrolidinomethyl)benzimidazolyl>oxy]-propyl}-1H-1,2,4-triazole-3,5-diamine.

13. The compound according to claim 1 which is 1-methyl-3-ethyl amino-5-[2-<5-(2-dimethylaminomethylbenzimidazolyl)methylthio>ethyl]-1H-1,2,4-triazole-5-amine.

14. The compound according to claim 1 wherein R is

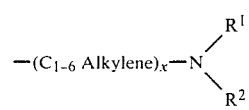

group wherein X is 0 or 1, $R^1$ and $R^2$ are independently hydrogen or $C_{1-6}$ alkyl.

15. The compound according to claim 1 wherein R is hydrogen or $C_{1-6}$ alkyl.

16. The compound according to claim 1 wherein R is unsubstituted amidino, $C_{1-6}$ alkyl-substituted amidino, unsubstituted guanidino or $C_{1-6}$ alkyl-substituted guanidino.

17. The compound according to claim 1, wherein R is

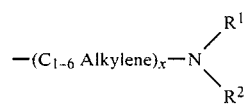

group wherein X is 0 or 1,

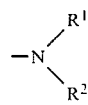

is a heterocyclic radical which is a member selected from the group consisting of (1) morpholino, (2) piperidino, (3) pyrrolidino, (4) piperazino, (5) thiomorpholino and (6) morpholino, piperidino, pyrrolidino, piperazino and thiomorpholino substituted by $C_1$-$C_6$ alkyl.

18. The compound according to claim 14 wherein X is 1.

19. The compound according to claim 14 wherein X is 0.

20. The compound according to claim 18 wherein $R^{10}$ is $C_{1-6}$ alkyl.

21. The compound according to claim 18 wherein $R^{10}$ is hydrogen; an unsubstituted phenyl; a phenyl substituted by $C_{1-4}$ alkylenedioxy, $C_{1-6}$ alkoxy or halogen; or a mono- or di-$C_{1-6}$ alkylamino-$C_{1-6}$ alkyl.

22. The compound according to claim 20 wherein $R^{11}$ and $R^{12}$ are independently hydrogen or $C_{1-6}$ alkyl.

23. The compound according to claim 20 wherein

is a heterocyclic radical which is a member selected from the group consisting of (1) morpholino, (2) piperidino, (3) pyrrolidino, (4) piperazino, (5) thiomorpholino and (6) morpholino, piperidino, pyrrolidino, piperazino and thiomorpholino substituted by $C_{1-6}$ alkyl.

24. The compound according to claim 21 wherein $R^{11}$ and $R^{12}$ are independently hydrogen or $C_{1-6}$ alkyl.

25. The compound according to claim 21 wherein

is a heterocyclic radical which is a member selected from the group consisting of (1) morpholino, (2) piperidino, (3) pyrrolidino, (4) piperazino, (5) thiomorpholino and (6) morpholino, piperidino, pyrrolidino, piperazino, thiomorpholino substituted by $C_{1-6}$ alkyl.

26. The compound according to claim 22 wherein $R^{11}$ and $R^{12}$ are hydrogen.

27. The compound according to claim 26 wherein Y is —S—.

28. The compound according to claim 26 wherein Y is —O— or —NH—.

29. The compound according to claim 27 wherein m is 1.

30. The compound according to claim 28 wherein m is 0.

31. The compound according to claim 14 wherein X is 1.

32. The compound according to claim 14 wherein X is 0.

33. The compound according to claim 31 wherein Y is —O— and m is 0.

34. The compound according to claim 30 wherein Y is —O— and m is 0.

35. A process for the preparation of a compound according to claim 1 wherein $R^{11}$ and $R^{12}$ are hydrogen of formula

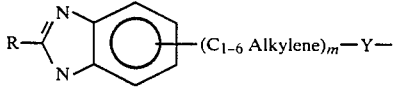

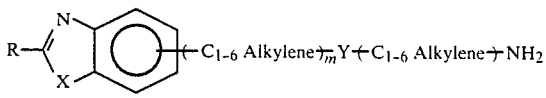

wherein R, m, Y, $R^{10}$ are defined in claim 1, which consists of reacting a compound of formula:

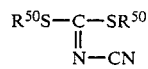

with a compound of formula:

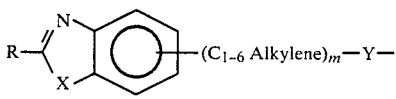

wherein $R^{50}$ is $C_{1-6}$ alkyl to obtain a compound P

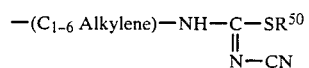

(P)

and then reacting said compound P with an unsubstituted or substituted hydrazine of formula $R^{10}$—NH—NH$_2$ and isolating said compound from the reaction mixture.

36. The method of treating peptic ulcers in a subject affected by peptic ulcers which consists of administering to said subject a compound of formula

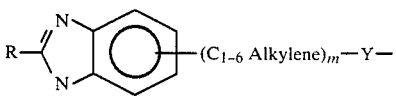

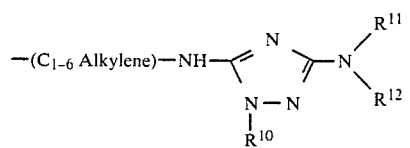

wherein
R is (a) hydrogen; (b) $C_{1-6}$alkyl; (c) an unsubstituted amidino or a $C_{1-6}$ alkyl substituted amidino; (d) an unsubstituted guanidino or a $C_{-16}$ alkyl substituted guanidino; (e) a

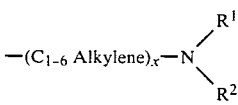

group wherein x is 0 or 1,
$R^1$ and $R^2$ are independently hydrogen or $C_{1-6}$ alkyl, or

is an unsubstituted heterocyclic radical which is a member selected from the group consisting of (1) morpholino, (2) piperidino, (3) pyrrolidino, (4) piperazino, (5) thiomorpholino, and (6) morpholino, piperidino, pyrrolidino, piperazino, thiomorpholino substituted by $C_{1-6}$ alkyl; Y is independently a —NH—, an —O—, or a —S—;
m is 0 or 1;
$R^{10}$ is hydrogen, an unsubstituted phenyl or a phenyl substituted by $C_{1-4}$ alkylenedioxy, $C_{1-6}$ alkoxy or halogen, or a mono- or di-$C_{1-6}$ alkylamino-$C_{1-6}$ alkyl;

$R^{11}$ and $R^{12}$ are independently hydrogen, $C_{1-6}$ alkyl or

is a heterocyclic radical which is a member selected from the group consisting of (1) morpholino, (2) piperidino, (3) pyrrolidino, (4) piperazino, (5) thiomorpholino, (6) pyridylideneimino and (7) morpholino, piperidino, pyrrolidino, piperazino, thiomorpholino, pyridylideneimino substituted by $C_{1-6}$ alkyl, and pharmaceutically compatible salts thereof, solvates and hydrates thereof in unit dosage form containing between 0.2 and 16 mg/kg of said compound with respect to the body weight of said subject.

37. The method according to claim 36 wherein said compound is 1-methyl-5-[2-<5-(2-dimethylaminomethylbenzimidazolyl)methylthio>ethyl]-1H-1,2,4-triazole-3,5-diamine.

* * * * *